(12) United States Patent
Marto et al.

(10) Patent No.: US 11,789,025 B2
(45) Date of Patent: *Oct. 17, 2023

(54) REAGENTS AND METHODS FOR ANALYSIS OF PROTEINS AND METABOLITES TARGETED BY COVALENT PROBES

(71) Applicant: Dana-Farber Cancer Institute, Inc., Boston, MA (US)

(72) Inventors: Jarrod A Marto, Wayland, MA (US); Scott B Ficarro, Melrose, MA (US); Guillaume Adelmant, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 188 days.

This patent is subject to a terminal disclaimer.

(21) Appl. No.: 17/080,373

(22) Filed: Oct. 26, 2020

(65) Prior Publication Data

US 2021/0072254 A1 Mar. 11, 2021

Related U.S. Application Data

(63) Continuation of application No. 16/461,486, filed as application No. PCT/US2017/063443 on Nov. 28, 2017, now Pat. No. 10,969,394.

(60) Provisional application No. 62/427,042, filed on Nov. 28, 2016.

(51) Int. Cl.
| | |
|---|---|
| *G01N 33/68* | (2006.01) |
| *C07C 225/14* | (2006.01) |
| *C07C 233/33* | (2006.01) |
| *C07C 255/60* | (2006.01) |
| *C07C 321/04* | (2006.01) |
| *C07C 321/14* | (2006.01) |
| *C07D 209/34* | (2006.01) |
| *C07D 211/70* | (2006.01) |
| *C07D 219/04* | (2006.01) |
| *C07D 233/88* | (2006.01) |
| *C07D 241/04* | (2006.01) |
| *C07D 249/12* | (2006.01) |
| *C07D 265/30* | (2006.01) |
| *C07D 265/34* | (2006.01) |
| *C07D 265/36* | (2006.01) |
| *C07D 295/185* | (2006.01) |
| *C07D 307/54* | (2006.01) |
| *C07D 401/04* | (2006.01) |
| *C07D 401/12* | (2006.01) |
| *C07D 401/14* | (2006.01) |
| *C07D 403/04* | (2006.01) |
| *C07D 403/12* | (2006.01) |
| *C07D 471/04* | (2006.01) |
| *C07D 487/04* | (2006.01) |
| *C07D 498/06* | (2006.01) |

(52) U.S. Cl.
CPC ....... *G01N 33/6848* (2013.01); *C07C 225/14* (2013.01); *C07C 233/33* (2013.01); *C07C 255/60* (2013.01); *C07C 321/04* (2013.01); *C07C 321/14* (2013.01); *C07D 209/34* (2013.01); *C07D 211/70* (2013.01); *C07D 219/04* (2013.01); *C07D 233/88* (2013.01); *C07D 241/04* (2013.01); *C07D 249/12* (2013.01); *C07D 265/30* (2013.01); *C07D 265/34* (2013.01); *C07D 265/36* (2013.01); *C07D 295/185* (2013.01); *C07D 307/54* (2013.01); *C07D 401/04* (2013.01); *C07D 401/12* (2013.01); *C07D 401/14* (2013.01); *C07D 403/04* (2013.01); *C07D 403/12* (2013.01); *C07D 471/04* (2013.01); *C07D 487/04* (2013.01); *C07D 498/06* (2013.01); *G01N 2560/00* (2013.01)

(58) Field of Classification Search
CPC .......... G01N 33/6848; G01N 2560/00; G01N 2333/912; C07C 225/14; C07C 233/33; C07C 255/60; C07C 321/04; C07C 321/14; C07D 209/34; C07D 211/70; C07D 219/04; C07D 233/88; C07D 241/04; C07D 249/12; C07D 265/30; C07D 265/34; C07D 265/36; C07D 295/185; C07D 307/54; C07D 401/04; C07D 401/12; C07D 401/14; C07D 403/04; C07D 403/12; C07D 471/04; C07D 487/04; C07D 498/06

See application file for complete search history.

(56) References Cited

U.S. PATENT DOCUMENTS

| | | |
|---|---|---|
| 4,642,306 A | 2/1987 | Rosa |
| 7,786,213 B2 * | 8/2010 | Maynard .............. A61K 47/665 527/202 |
| 10,969,394 B2 | 4/2021 | Marto et al. |
| 2003/0143569 A1 | 7/2003 | Abrams et al. |
| 2004/0014140 A1 | 1/2004 | Erlanson et al. |
| 2007/0027310 A1 | 2/2007 | Lee |
| 2007/0054407 A1 | 3/2007 | Chen et al. |

(Continued)

OTHER PUBLICATIONS

Dixon et al. Stress-Induced Protein S-Glutathionylation in Arabidopsis. Plant Physiology, Aug. 2005, vol. 138, pp. 2233-2244. (Year: 2005).*

(Continued)

*Primary Examiner* — Marcela M Cordero Garcia

(74) *Attorney, Agent, or Firm* — Dana-Farber Cancer Institute, Inc.

(57) ABSTRACT

The present application relates to mass spectrometry methods for use in identifying proteins or other biomolecules which are bound irreversibly by test compounds.

19 Claims, 28 Drawing Sheets

Specification includes a Sequence Listing.

(56) References Cited

U.S. PATENT DOCUMENTS

| | | |
|---|---|---|
| 2008/0280316 A1 | 11/2008 | Imai |
| 2013/0144541 A1* | 6/2013 | Rychnovsky ........ C07D 207/46 435/23 |
| 2013/0261013 A1 | 10/2013 | Baltzer et al. |
| 2019/0346454 A1 | 11/2019 | Marto et al. |

OTHER PUBLICATIONS

Person et al., "Alkylation of Cytochrome c by (Glutathion-S-yl)-1,4-benzoguinone and Iodoacetannide Demonstrates Compound-Dependent Site Specificity," Chem. Res. Toxicol., 2005, 18(1):41-50.

Campuzano et al., "High-Throughput Mass Spectrometric Analysis of Covalent Protein-Inhibitor Adducts for the Discovery of Irreversible Inhibitors: A Complete Workflow," Journal of Biomolecular Screening, Dec. 16, 2015, 21(2):136-144.

Cui et al., "BCR-ABL tyrosine kinase inhibitor pharmacophore model derived from a series of phenyl aminopyrimidine-based (PAP) derivatives," Bioorganic & Medical Chemistry Letters, Feb. 9, 2013, 23(8):2442-2450.

EP Search Report, in European Appln. No. 17874785.3, dated Jun. 4, 2020, 17 pages.

EP Search Report in European Appln. No. 17874785.3, dated Sep. 7, 2020, 13 pages.

Ficarro et al, "Online Nanoflow Multidimensional Fractionation for High Efficiency Phosphopetide Analysis," Mol. Cell Proteomics, 2011, 10(11):O111.011064, 19 pages.

Ficarro et al., "Leveraging Gas-Phase Fragmentation Pathways for Improved Identification and Selective Detection of Targets Modified by Covalent Probes," Analytical Chemistry, Nov. 30, 2016, 88(24):12248-12254.

Fontan et al," MALT1 Small Molecule Inhibitors Specifically Supress ABC-DLBCL In Vitro and In Vivo," Cancer Cell, 2012, 22:812-824, 13 pages.

Kwiatkowski et al, "Development of Selective Covalent JAK3 Inhibitors," Nature, 2014, 511:616-620; Tan et al, J. Med. Chem. 2015, 58:6589-6606, 49 pages.

Kwiatkowski et al., "Targeting transcription regulation in cancer with a covalent CDK7 inhibitor: Supplementary Information." Nature, Jun. 22, 2014, 511(7511):1-34.

Kwiatokski et al., "Targeting 1-15 transcription regulation in cancer with a covalent CDK7 inhibitor," Nature, Jun. 22, 2014, 511(7511):616-620.

Masterorganicchemistry.com, [online], "Ace Your Next Organic Chemistry Exam." Jan. 22, 2020, retrieved on Mar. 19, 2020. retrieved from URL<https://www.masterorganicchennistry.conn/2015/07/05/thiols-and-thioethers/>, 23 pages.

PCT International Preliminary Report on Patentability in Appln. No. PCT/US2017/063443, dated May 28, 2019, 13 pages.

PCT International Search Report in International Appln. No. PCT/US2017/063443, dated Apr. 25, 2018, 4 pages.

Perkins et al, "Probability-based Protein Identification by Search Sequence Databases Using Mass Spectrometry Data," Electrophoresis, 1999, 20:3551-3567, 17 pages.

Reverdy et al, "Discovery of Specific Inhibitors of Human USP&/HAUSP Deubiquitinating Enzyme," Chem. Biol., 2012, 19:467-477, 11 pages.

Zhang et al, "Discovery of Potent and Selective Covalent Inhibitors of JNK." Chem. Biol., 2012, 19:140-154, 15 pages.

Office Action in European Appln. No. 17874785.3, dated Apr. 4, 2022, 6 pages.

Burstein et al., "Neratinib, an Irreversible ErbB Receptor Tyrosine Kinase Inhibitor, in Patients with Advanced ErbB2-Positive Breast Cancer", J. Clin. Oncol., 2010, 28:1301-1307.

Pan et al., "Discovery of Selective Irreversible Inhibitors for Bruton's Tyrosine Kinase," ChemMedChem, 2007, 2:58-61.

Tan et al., "Development of Selective Covalent JAK3 Inhibitors," J. Med. Chem, 2015, 58:6589-6606.

Wu et al., "Discovery of a Potent, Covalent BTK Inhibitor for B-Cell Lymphoma", ACS Chem. Biol. 2014, 9:1086-1091.

* cited by examiner

REAGENTS AND METHODS FOR ANALYSIS OF PROTEINS AND METABOLITES TARGETED BY COVALENT PROBES

CROSS-REFERENCE TO RELATED APPLICATIONS

This application is a continuation of U.S. application Ser. No. 16/461,486, filed on May 16, 2019, which is a national phase filing under 35 U.S.C. § 371 of International application number PCT/US2017/063443, filed Nov. 28, 2017, which claims the benefit of U.S. Provisional Application Ser. No. 62/427,042, filed Nov. 28, 2016. The disclosures of the prior applications are incorporated herein by reference in their entirety.

SEQUENCE LISTING

This application contains an Amended Sequence Listing that has been submitted electronically in computer readable form named 2211C01US_Amended_Seq_Listing_28APR2023. The ASCII file, created on Apr. 24, 2023, is 3750 bytes in size. The material in the ASCII file is hereby incorporated by reference in its entirety.

TECHNICAL FIELD

This disclosure relates to mass spectrometry-based identification of proteins or other biomolecules which are bound irreversibly by test compounds.

BACKGROUND

The thiol side-chain of cysteine is subject to numerous endogenous (e.g., enzymatic or metabolic) and environmentally-mediated chemical modifications. In addition, there is renewed interest in developing small molecules which exert therapeutic effect via covalent modification of cysteine residues in target proteins. In cases involving endogenous (e.g., cellular) target discovery, the specific cysteine residue, or often the protein itself, which is modified by the covalent probe is not known. Even when the target is known, the landscape of off-target molecules remains difficult to identify and may represent a confounding variable in determining (poly)pharmacology, therapeutic window, potential side effects, etc. Similarly, for any established covalent probe-target combination, it is difficult to quantify the fraction of endogenous target molecule that is bound by the covalent probe. Given the biochemical complexity and dynamic range of mammalian proteomes, high-throughput characterization of small molecule covalent probes remains enormously challenging.

Several approaches have been developed as surrogates for the identification of proteins or other biomolecules covalently modified by small molecule probes. In one method, a small molecule of interest is synthesized with an affinity tag (e.g., biotin) or a biorthogonal reactive group (e.g., alkyne) which is subsequently used as a "handle" to enrich covalently-bound protein targets from complex biological mixtures. The addition of these moieties can disrupt the binding kinetics and/or activity of the native probe and may also negate cell plasma membrane permeability, requiring incubation of the probe in protein lysate instead of directly in live cells. A second approach uses broad-activity probes, built around iodoacetamide, for example, which are used in a 'competition format' with the small molecule inhibitor of interest. In this case, the readout is "indirect," meaning that proteins not detected, or detected with significantly reduced abundance, are assumed to be modified by the experimental inhibitor, and hence less-available for labeling by the broad-activity probes. The indirect assay may not include an enrichment step, and therefore may be further limited by the stochastic and abundance-biased sequencing inherent to mass spectrometry-based identification. A more recent method relies on the ability of small molecule probes to impart increased thermal stability to their targets. This paradigm utilizes native probes in live cells with subsequent thermal cycling of lysates. The assumption is that non-bound protein targets will precipitate from solution, while modified proteins will remain solubilized and available for processing and identification by mass spectrometry-based techniques. The variables for probe-mediated thermal stability are not completely understood. As a result, this assay format is subject to high or indeterminate false-positive/-negative rates.

SUMMARY

The present application provides, inter alia, an analytical method, comprising:
i) contacting a test compound with a polypeptide to form a test compound-polypeptide conjugate;
ii) analyzing the test compound-polypeptide conjugate using a mass spectrometry assay;
iii) detecting one or more thiolated ions, or derivative ions thereof, produced in the mass spectrometry assay; and
iv) identifying that the test compound irreversibly bonds to the polypeptide based on the detection of the one or more thiolated ions, or derivative ions thereof, in the mass spectrometry assay.

In some embodiments, the method comprises:
i) contacting a test compound with a polypeptide to form a test compound-polypeptide conjugate;
ii) analyzing the test compound-polypeptide conjugate using a mass spectrometry assay;
iii) detecting one or more thiolated ions, or derivative ions thereof, produced in the mass spectrometry assay; and
iv) identifying that the test compound irreversibly bonds to the polypeptide based on the detection of the one or more thiolated ions, or derivative ions thereof, in the mass spectrometry assay.

In some embodiments, the compound-polypeptide conjugate comprises one or more thioether bonds between the test compound and the polypeptide. In some embodiments, the irreversible bond is an irreversible covalent bond.

In some embodiments, step i) comprises contacting the test compound and the polypeptide in the presence of a first solvent component. In some embodiments, the first solvent component is DMSO. In some embodiments, step i) further comprises contacting the compound and the polypeptide in the presence of a buffer agent. In some embodiments, the buffer agent is triethylammonium bicarbonate. In some embodiments, step i) is performed at a temperature of about 4° C. to about 65° C. In some embodiments, step i) is performed for about 1 second to about 16 hours. In some embodiments, step i) is performed using a molar excess of the test compound compared to the polypeptide. In some embodiments, the molar ratio of the test compound to the polypeptide is from about 1:1 to about 100:1.

In some embodiments, the method further comprises contacting the test compound-polypeptide conjugate with an acid in the presence of a second solvent component prior to performing the mass spectrometry assay of step ii). In some embodiments, the acid is an organic acid. In some embodiments, the acid is acetic acid. In some embodiments, the second solvent component comprises acetonitrile. In some embodiments, the second solvent component further comprises water.

In some embodiments, the method further comprises digesting the test compound-polypeptide conjugate prior to the performing the mass spectrometry assay of step ii). In some embodiments, the digesting comprises reacting the test compound-polypeptide conjugate with trypsin in the presence of a third solvent component. In some embodiments, the third solvent component comprises aqueous ammonium bicarbonate.

In some embodiments, the polypeptide comprises one or more amino acids residues comprising at least one sulfur atom. In some embodiments, the polypeptide comprises one or more cysteine residues. In some embodiments, the test compound is identified as irreversibly bonding to one or more cysteine residues of the polypeptide. In some embodiments, the test compound comprises one or more acrylamide groups. In some embodiments, the test compound comprises one or more acrylamide groups, dimethylamino acrylamide groups, iodoacetamide groups, chloroacetamide groups, maleimide groups, or reactive C—X bonds, wherein X is a halogen. In some embodiments, the test compound is isotopically labeled with heavy isotopes of carbon, oxygen, nitrogen, sulfur, phosphorous, chlorine, bromine, or hydrogen.

In some embodiments, the test compound is identified as a kinase inhibitor or a deubiquitinase inhibitor. In some embodiments, the test compound is identified as a kinase inhibitor. In some embodiments, the test compound is selected from the group consisting of JNK-IN-7, HBX-19818, MI-2, TL10-201, THZ531, THZ1, QL-47, ibrutinib, and neratinib. In some embodiments, the test compound is selected from the group consisting of JNK-IN-7, HBX-19818, MI-2, TL10-201, THZ531, THZ1, QL-47, TL11-113, ibrutinib, and neratinib.

In some embodiments, the test compound is chemically modified to facilitate affinity-based enrichment of test compound polypeptide conjugates. In some embodiments, chemical-modification of the test compound comprises addition of an affinity tag such as a peptide-epitope, biotin, or desthiobiotin. In some embodiments, the chemical-modification of the test compound comprises addition of a bio-orthogonal moiety such as an alkyne or azide.

In some embodiments, a reagent having broad thiol reactivity and high yield of thiolated ions, or derivative ions thereof, is used to measure the binding stoichiometry of the test compound to its target. In some embodiments, the reagent with broad thiol reactivity and high yield of thiolated ions, or derivative ions thereof, is selected from the group consisting of:
2-iodo-1-morpholinoethan-1-one;
1-((2R,6R)-2,6-dimethylmorpholino)-2-iodoethan-1-one;
1-((2R,6S)-2,6-dimethylmorpholino)-2-iodoethan-1-one;
1-(2,2-dimethylmorpholino)-2-iodoethan-1-one;
1-(3,5-dimethylmorpholino)-2-iodoethan-1-one;
1-(hexahydrocyclopenta[b][1,4]oxazin-4(4aH)-yl)-2-iodoethan-1-one;
1-(2,3-dihydro-4H-benzo[b][1,4]oxazin-4-yl)-2-iodoethan-1-one;
N-(4-cyanophenyl)-2-iodoacetamide;
N-(2,5-dimethylphenyl)-2-iodoacetamide;
N-(2,5-dimethoxyphenyl)-2-iodoacetamide;
2-iodo-N-phenylacetamide;
2-iodo-N-(p-tolyl)acetamide;
2-iodo-1-(4-methylpiperazin-1-yl)ethan-1-one 2,2,2-trifluoroacetate;
N-(furan-2-ylmethyl)-2-iodoacetamide;
2-iodo-N-(1-methyl-1H-imidazol-4-yl)acetamide; and
N-ethylmaleimide.

In some embodiments, the reagent having broad thiol reactivity is isotopically labeled with heavy isotopes of carbon, oxygen, nitrogen, sulfur, phosphorous, chlorine, bromine, or hydrogen.

In some embodiments, the polypeptide is a protein or a protein fragment. In some embodiments, the polypeptide is a protein fragment comprising from about 10 to about 30 amino acid residues.

In some embodiments, the polypeptide is a kinase, a kinase fragment, a deubiquitinase, or a deubiquitinase fragment. In some embodiments, the polypeptide is a kinase or deubiquitinase selected from the group consisting of JNK2, JAK3, CDK7, CDK12, TAK1, ITK, USP-7, and EGFR, or a fragment thereof.

In some embodiments, the polypeptide is a kinase or a kinase fragment. In some embodiments, the polypeptide is a kinase selected from the group consisting of JNK2, JAK3, CDK7, CDK12, ITK, USP-7, and EGFR, or a fragment thereof. In some embodiments, the polypeptide is a kinase fragment comprising from about 10 to about 30 amino acid residues.

In some embodiments, the polypeptide comprises an amino acid sequence having at least 90% sequence identity to a sequence selected from the group consisting of:

```
                                           (SEQ ID NO: 1)
L-M-D-A-N-L-C-Q-V-I-Q-M-E;

(SEQ ID NO: 2)
L-V-M-E-Y-L-P-S-G-C-L-R;

(SEQ ID NO: 3)
M-A-P-P-D-L-P-H-W-Q-D-C-H-E-L-W-S-K;

(SEQ ID NO: 4)
H-G-C-L-S-D-Y-L-R-S-Q-R-G-L-F-A-A-E;

(SEQ ID NO: 5)
Y-F-S-N-R-P-G-P-T-P-G-C-Q-L-P-R-P-N-C-P-V-E-T-L-K;

(SEQ ID NO: 6)
G-C-L-L-D-Y-V-R;

(SEQ ID NO: 7)
F-G-L-C-S-G-P-A-D-T-G-R;

(SEQ ID NO: 8; sL = $^{15}$N-1, $^{13}$C-6 leucine)
Y-M-A-N-G-C-L-sL-N-Y-L-R;

(SEQ ID NO: 9)
I-C-D-F-G-T-A-C-D-I-Q-T-H-M-T-N-N-K;
and
                                          (SEQ ID NO: 10)
Y-F-S-N-R-P-G-P-T-P-G-C-Q-L-P-(13C6-15N4)R-P-N-C-

P-V-E-T-L-K.
```

In some embodiments, the polypeptide comprises an amino acid sequence having at least 90% sequence identity to a sequence selected from the group consisting of:

```
                                           (SEQ ID NO: 1)
L-M-D-A-N-L-C-Q-V-I-Q-M-E;

(SEQ ID NO: 2)
L-V-M-E-Y-L-P-S-G-C-L-R;
```

-continued

M-A-P-P-D-L-P-H-W-Q-D-C-H-E-L-W-S-K; (SEQ ID NO: 3)

H-G-C-L-S-D-Y-L-R-S-Q-R-G-L-F-A-A-E; (SEQ ID NO: 4)

Y-F-S-N-R-P-G-P-T-P-G-C-Q-L-P-R-P-N-C-P-V-E-T-L-K; (SEQ ID NO: 5)

G-C-L-L-D-Y-V-R; (SEQ ID NO: 6)

F-G-L-C-S-G-P-A-D-T-G-R; (SEQ ID NO: 7)
and

Y-M-A-N-G-C-L-sL-N-Y-L-R. (SEQ ID NO: 8)

The present application further provides an analytical method, comprising:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) analyzing the third mixture using a mass spectrometry assay;
iii) detecting one or more thiolated ions, or derivative ions thereof, produced in the mass spectrometry assay; and
iv) identifying that one or more of the test compounds binds irreversibly to one or more of the polypeptides based on the detection of the one or more thiolated ions, or derivative ions thereof, in the mass spectrometry assay.

The present application further provides an analytical method, comprising:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) analyzing the third mixture using a mass spectrometry assay;
iii) detecting one or more thiolated ions produced in the mass spectrometry assay; and
iv) identifying that one or more of the test compounds binds irreversibly to one or more of the polypeptides based on the detection of the one or more thiolated ions in the mass spectrometry assay.

In some embodiments, the method further comprises digesting the test compound-polypeptide conjugate prior to performing the mass spectrometry assay of step ii). In some embodiments, the digesting comprises reacting the test compound-polypeptide conjugate with trypsin in the presence of a third solvent component. In some embodiments, the third solvent component comprises aqueous ammonium bicarbonate.

In some embodiments, each of the one or more test compound-polypeptide conjugates comprises one or more thioether bonds between the test compound and the polypeptide. In some embodiments, each of the polypeptides comprises one or more cysteine residues. In some embodiments, each of the test compounds is identified as irreversibly bonding to one or more cysteine residues of at least one of the one or more polypeptides. In some embodiments, each of the test compounds comprises one or more thiol-reactive groups including, but not limited to, acrylamide groups, dimethylamino acrylamide groups, iodoacetamide groups, chloroacetamide groups, maleimide groups, or reactive C—X groups, wherein X is a halogen. In some embodiments, each of the test compounds are isotopically labeled with heavy isotopes of carbon, oxygen, nitrogen, sulfur, phosphorous, chlorine, bromine, or hydrogen. In some embodiments, each of the test compounds comprises one or more independently selected acrylamide groups. In some embodiments, the test compound is chemically modified to facilitate affinity-based enrichment of test compound polypeptide conjugates. In some embodiments chemical-modification of the test compound comprises addition of an affinity tag such as a peptide-epitope, biotin, or desthiobiotin. In some embodiments the chemical-modification of the test compound comprises addition of a bio-orthogonal moiety such as an alkyne or azide.

In some embodiments, one or more of the test compounds is identified as a kinase inhibitor or a deubiquitinase inhibitor. In some embodiments, one or more of the test compounds is identified as a kinase inhibitor. In some embodiments, at least one of the test compounds is selected from the group consisting of JNK-IN-7, TL10-201, THZ531, THZ1, QL-47, ibrutinib, neratinib and TL11-113. In some embodiments, at least one of the test compounds is selected from the group consisting of JNK-IN-7, TL10-201, THZ531, THZ1, QL-47, ibrutinib, and neratinib. In some embodiments, each of the one or more polypeptides is a protein or a protein fragment. In some embodiments, the polypeptide is a protein fragment comprising from about 10 to about 30 amino acid residues. In some embodiments, each of the one or more polypeptides is a kinase, a kinase fragment, a deubiquitinase or a deubiquitinase fragment. In some embodiments, each of the one or more polypeptides is a kinase or a kinase fragment.

In some embodiments, at least one of the polypeptides is a kinase or deubiquitinase selected from the group consisting of JNK2, JAK3, CDK7, CDK12, ITK, USP-7, TAK1, and EGFR, or a fragment thereof.

In some embodiments, at least one of the polypeptides is a kinase selected from the group consisting of JNK2, JAK3, CDK7, CDK12, ITK, USP-7, and EGFR, or a fragment thereof.

In some embodiments, the polypeptide is a kinase fragment comprising from about 10 to about 30 amino acid residues. In some embodiments, at least one of the polypeptides comprises an amino acid sequence having at least 90% sequence identity to a sequence selected from the group consisting of:

L-M-D-A-N-L-C-Q-V-I-Q-M-E; (SEQ ID NO: 1)

L-V-M-E-Y-L-P-S-G-C-L-R; (SEQ ID NO: 2)

M-A-P-P-D-L-P-H-W-Q-D-C-H-E-L-W-S-K; (SEQ ID NO: 3)

H-G-C-L-S-D-Y-L-R-S-Q-R-G-L-F-A-A-E; (SEQ ID NO: 4)

Y-F-S-N-R-P-G-P-T-P-G-C-Q-L-P-R-P-N-C-P-V-E-T-L-K; (SEQ ID NO: 5)

G-C-L-L-D-Y-V-R; (SEQ ID NO: 6)

-continued

F-G-L-C-S-G-P-A-D-T-G-R; (SEQ ID NO: 7)

Y-M-A-N-G-C-L-sL-N-Y-L-R; (SEQ ID NO: 8)

I-C-D-F-G-T-A-C-D-I-Q-T-H-M-T-N-N-K; (SEQ ID NO: 9)
and

Y-F-S-N-R-P-G-P-T-P-G-C-Q-L-P-(13C6-15N4)R-P-N-C-P-V-E-T-L-K. (SEQ ID NO: 10)

In some embodiments, the polypeptide is a kinase fragment comprising from about 10 to about 30 amino acid residues. In some embodiments, at least one of the polypeptides comprises an amino acid sequence having at least 90% sequence identity to a sequence selected from the group consisting of:

L-M-D-A-N-L-C-Q-V-I-Q-M-E; (SEQ ID NO: 1)

L-V-M-E-Y-L-P-S-G-C-L-R; (SEQ ID NO: 2)

M-A-P-P-D-L-P-H-W-Q-D-C-H-E-L-W-S-K; (SEQ ID NO: 3)

H-G-C-L-S-D-Y-L-R-S-Q-R-G-L-F-A-A-E; (SEQ ID NO: 4)

Y-F-S-N-R-P-G-P-T-P-G-C-Q-L-P-R-P-N-C-P-V-E-T-L-K; (SEQ ID NO: 5)

G-C-L-L-D-Y-V-R; (SEQ ID NO: 6)

F-G-L-C-S-G-P-A-D-T-G-R; (SEQ ID NO: 7)
and

Y-M-A-N-G-C-L-sL-N-Y-L-R. (SEQ ID NO: 8)

In some embodiments, the method further comprises reacting one or more test compounds, each containing a thiol-reactive moiety, with a second compound containing a nucleophilic thiol group to form one or more test compound thioether conjugates, prior to the contacting of step i). In some embodiments, the second compound is selected from the group consisting of beta-mercaptoethanol, glutathione, 2-mercaptobenzoic acid, and hydrogen sulfide.

In some embodiments, the method further comprises reacting one or more acrylamide compounds with a thiolated compound to form one or more acrylamide thiolated derivatives, prior to the contacting of step i).

In some embodiments, the method further comprises analyzing the one or more test compound thioether conjugates in a mass spectrometry assay prior to the contacting step i). In some embodiments, analyzing the test compound thioether conjugates comprises generating a database of fragment ion spectra comprising the mass spectra of each of the one or more test compound thioether conjugates. In some embodiments, the method further comprises gas-phase isolation and fragmentation (e.g., MS/MS/MS or MS3) of the one or more of the thiolated ions, or derivative ions thereof, formed during MS/MS of the one or more test compound thioether conjugates.

In some embodiments, the method further comprises analyzing the one or more acrylamide thiolated derivatives in a mass spectrometry assay. In some embodiments, analyzing the one or more acrylamide thiolated derivatives comprises generating a database of fragment ion spectra comprising the mass spectra of each of the one or more acrylamide thiolated derivatives.

In some embodiments, the method further comprises isolating the one or more thiolated ions after the detecting of step iii). In some embodiments, the method further comprises gas-phase isolation and fragmentation (e.g., MS/MS/MS or MS3) of the one or more thiolated ions, or derivative ions thereof, detected in step iii).

In some embodiments, the method further comprises performing a mass spectrometry assay on the one or more isolated thiolated ions prior to the identifying of step iv).

In some embodiments, the identifying of step iv) further comprises identifying a mass spectrum in the database of fragment ion spectra (e.g., MS/MS/MS or MS3 fragment ion spectra) from the one or more test compound thioether conjugates that is substantially identical to the fragment ion spectrum derived from the gas-phase isolation and fragmentation analysis (e.g., MS/MS/MS or MS3) performed on the thiolated ion detected in step iii).

In some embodiments, the identifying of step iv) further comprises identifying a mass spectrum in the database of fragment ion spectra that is substantially identical to the mass spectrum of the isolated thiolated ion. In some embodiments, the thiolated compound is β-mercaptoethanol.

In some embodiments, the first mixture comprises more than one test compound. In some embodiments the first mixture comprises a combination of one or more test compounds and one or more chemically-modified test compounds (e.g., a test compound comprising a peptide-epitope, biotin, desthiobiotin, or a bio-orthogonal moiety such as an alkyne or azide). In some embodiments, the second mixture comprises more than one polypeptide. In some embodiments, the first mixture comprises more than one test compound and the second mixture comprises more than one polypeptide. In some embodiments the first mixture comprises a combination of one or more test compounds and one or more chemically-modified test compounds (e.g., a test compound comprising a peptide-epitope, biotin, desthiobiotin, or a bio-orthogonal moiety such as an alkyne or azide), and the second mixture comprises more than one polypeptide.

The present application further provides an analytical method, comprising:
  i) reacting one or more test compounds each containing a thiol-reactive moiety with a second compound containing a thiol group to form one or more test compound thioether conjugates;
  ii) analyzing the one or more test compound thioether conjugates in a mass spectrometry assay;
  iii) generating a database of fragment ion spectra comprising the mass spectra derived from the mass spectrometry assay (e.g., MS/MS/MS or MS3) performed on each of the one or more test compound thioether conjugates;
  iv) contacting a first mixture comprising more than one test compound with a second mixture comprising more than one polypeptide to form a third mixture comprising more than one test compound-polypeptide conjugate, wherein each of the test compound-polypeptide conjugates comprise one or more thioether bonds;
  v) analyzing the third mixture using a mass spectrometry assay;
  vi) detecting one or more thiolated ions, or derivative ions thereof, produced in the mass spectrometry assay;

vii) performing gas phase isolation and MS/MS/MS or MS3 analysis on the one or more thiolated ions, or derivative ions thereof, to generate fragment ion spectra;

viii) comparing the fragment ion spectra generated in step vii) with the database of fragment ion spectra generated in step iii); and ix) identifying that one or more of the test compounds binds irreversibly to one or more of the polypeptides based on the detection of one or more thiolated ions, or derivative ions thereof, in the mass spectrometry assay of step v) and the identification of a mass spectrum in the database of fragment ion spectra that is substantially identical to the mass spectrum of the thiolated ion, or derivative ion thereof, generated in step iii).

In some embodiments, the fragment ion spectra generated in step vii) are diagnostic of the one or more test compounds.

The present application further provides an analytical method, comprising:

i) reacting one or more acrylamide compounds with a thiol-containing compound to form one or more acrylamide thiolated derivatives;

ii) analyzing the one or more acrylamide thiolated derivatives in a mass spectrometry assay;

iii) generating a database of fragment ion spectra comprising the mass spectra of each of the one or more acrylamide thiolated derivatives;

iv) contacting a first mixture comprising more than one test compound with a second mixture comprising more than one polypeptide to form a third mixture comprising more than one compound-polypeptide conjugate, wherein each of the compound-polypeptide conjugates comprise one or more thioether bonds;

v) analyzing the third mixture using a mass spectrometry assay;

vi) detecting one or more thiolated ions produced in the mass spectrometry assay;

vii) isolating the one or more thiolated ions;

viii) performing a mass spectrometry assay on the one or more isolated thiolated ions;

ix) comparing the mass spectra of the one or more thiolated ions to the database of fragment ion spectra; and x) identifying that one or more of the test compounds binds irreversibly to one or more of the polypeptides based on the detection of one or more thiolated ions in the mass spectrometry assay of step v) and the identification a mass spectrum in the database of fragment ion spectra that is substantially identical to the mass spectrum of the isolated thiolated ion of step viii).

Unless otherwise defined, all technical and scientific terms used herein have the same meaning as commonly understood by one of ordinary skill in the art to which this invention belongs. Methods and materials are described herein and in Appendix A of U.S. Provisional Patent Application No. 62/427,042 (the disclosure of which is incorporated herein by reference in its entirety) for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

(FIG. 1B) Ibrutinib labeled ITK peptide; and (FIG. 1C) Neratinib labeled EGFR peptide. Fragment ions containing the peptide N- (b-type) or C- (y-type) termini are indicated with glyphs above and below the peptide sequence. Modified cysteine residues are shown in bold, italic font. Thiolated ions are denoted with '*'. Structures for thiolated ions are shown adjacent to each mass spectrum.

(FIG. 2A) The deisotoped MS/MS spectrum for a THZ531 labeled CDK12 peptide yields a relatively low-confidence MASCOT score, largely due to an abundance of inhibitor related fragment ions (FIG. 2B, #1-#9; see Table 3 for proposed structures). Additional steps, comprising normalization of all fragment ions to z=1, including neutral loss of inhibitor as part of MASCOT variable-mod definition, and subtraction of peaks corresponding to internal fragmentation of the inhibitor yields a high-confidence MASCOT peptide score (FIG. 2C). Ions of type b and y are indicated with glyphs above and below the peptide sequence. Neutral loss ions are indicated with open circles. ++ indicates a doubly charged ion. (FIG. 2D) Scatter plots of MASCOT scores for BSA peptides modified by (left) THZ531 or (right) THZ1 for MS/MS data subject to deisotoping (y-axis) or full spectral preprocessing (x-axis). Dotted lines represent MASCOT score cutoffs for a 1% FDR.

(FIG. 3B) Neratinib; and (FIG. 3C) QL47. For comparison, each plot includes profiles for b-/y-type ions produced by MS/MS of the unlabeled triply charged peptide.

(FIG. 4A) Base-peak chromatogram (BPC) and (FIG. 4B) extracted ion chromatogram (XIC) from Q3MS scans and (FIG. 4C) individual Q3 full-scan mass spectrum recorded during analysis of a synthetic cysteine-containing peptide (FGLCSGPADTGR (SEQ ID NO: 7); indicated by "CYS") labeled with Ibrutinib and spiked into a mix of tryptic peptides derived from human myeloid K562 cells. Arrow indicates the elution time (FIGS. 4A and 4B) or m/z (FIG. 4C) for the labeled peptide. (FIG. 4D) Base-peak chromatogram, and (FIG. 4E) extracted ion chromatogram from precursor ion spectra (precursors of 475.19, corresponding to the thiolated ion of Ibrutinib; abbreviated as "Prec"), and (FIG. 4F) individual precursor ion mass spectrum recorded during the same LC-MS/MS analysis. Arrow indicates the elution time (FIGS. 4D and 4E) or precursor ion signal (FIG. 4F) for the Ibrutinib labeled peptide. (FIGS. 4C and 4F) The % values in each panel represent the gas phase enrichment, calculated as the relative contribution of each ion (arrow) as compared to the total ion current in that spectrum. (FIG. 4G) MS/MS spectrum of Ibrutinib labeled peptide triggered by precursor scans for m/z=475.19, corresponding to the thiolated ion of Ibrutinib. Fragment ions containing the peptide N- (b-type) or C- (y-type) termini are indicated with glyphs above and below the peptide sequence. Inhibitor-specific ions are labeled with numbers (see Table 3 for proposed structures of ions labeled #1-5).

(FIG. 8B) TL10-201 labeled JAK3 peptide; (FIG. 8C) THZ1 labeled CDK7 peptide; (FIG. 8D) HBX-19818 labeled USP7 peptide. MS/MS spectra of the synthetic cysteine-containing peptide FGLCSGPADTGR (SEQ ID NO: 7) conjugated to (FIG. 8E) QL-47; (FIGS. 8F, 8G) HBX-19818; and (FIG. 8H) MI-2. Fragment ions containing the peptide N- (b-type) or C- (y-type) termini are indicated with glyphs above and below the peptide sequence. Modified cysteine residues are shown in bold, italic print. Thiolated ions are denoted with '*'. (FIG. 8F) At a CE of 20 eV HBX-19818 modified peptide eliminates the inhibitor/thiol to produce an intense thiolated ion (marked '*') and a series of dehydroalanine containing b-/y-type ions (marked with open circles) along with b-/y-type ions (marked by filled circles). (FIG. 8G) At higher CE (65 eV) the HBX-19818 modified synthetic peptide produces an $ib_1$ ion (1) and other structure-specific ions (2, 3). Imm(F) indicates the immonium ion of phenylalanine. (FIG. 8H) MI-2 modified peptide also shows a peak corresponding to amide bond cleavage ("1").

(FIG. 10B) THZ1; (FIG. 10C) THZ531. For comparison, each plot includes profiles for b-/y-type ions produced by MS/MS of the unlabeled triply charged peptide. (FIG. 10D) Signal intensity as a function of collision energy for inhibitor-specific fragments recorded during MS/MS analysis of triply charged BTK peptide conjugated to JNK-IN-2 (JNK1 inhibitor). (FIGS. 10E and 10F) Signal intensity as a function of collision energy for thiolated ions recorded during MS/MS analysis of doubly- or triply-charged FGLCSGPADTGR (SEQ ID NO: 7) or BTK peptides conjugated to (FIG. 10E) TL10-201 (JAK3 inhibitor) or (FIG. 10F) JNK-IN-2 (JNK inhibitor).

(FIG. 11A) Base-peak chromatogram (BPC) and (FIG. 11B) extracted ion chromatogram (XIC) from Q3MS scans and (FIG. 11C) individual Q3 full-scan mass spectrum recorded during analysis of a synthetic cysteine-containing peptide labeled with Ibrutinib (FGLCSGPADTGR (SEQ ID NO: 7); indicated by CYS) and spiked into a mix of tryptic peptides derived from human myeloid K562 cells. Arrow indicates the elution time (FIGS. 11A and 11B) or m/z (FIG. 11C) for the labeled peptide. These data were generated from the same LC-MS/MS analysis as in FIGS. 4A-4G. Base-peak chromatogram and (FIG. 11E) extracted ion chromatogram from precursor ion spectra (precursors of 304.12, corresponding to alkylated amine cleavage; abbreviated as "Prec"), and individual precursor ion mass spectrum (FIG. 11F) recorded during the same LC-MS/MS analysis. Arrow indicates the elution time (FIGS. 11D and 11E) or precursor ion signal (FIG. 11F) for the Ibrutinib labeled peptide. (FIGS. 11C and 11F) The % values in each panel represent the gas phase enrichment, calculated as the relative contribution of each ion (arrow) as compared to the total ion current in that spectrum.

(FIG. 12A) Base-peak chromatogram (BPC) and (FIG. 12B) extracted ion chromatogram (XIC) from Q3MS scans and (FIG. 12C) individual Q3 full-scan mass spectrum recorded during analysis of a synthetic cysteine-containing peptide labeled with QL47 (FGLCSGPADTGR (SEQ ID NO: 7); indicated by CYS) and spiked into a mix of tryptic peptides derived from human myeloid K562 cells. Arrow indicates the elution time (FIGS. 12A-12B) or m/z (FIG. 12C) for the labeled peptide. (FIGS. 12D and 12G) Base-peak chromatograms; (FIGS. 12E and 12H) extracted ion chromatograms from precursor ion spectra; and (FIGS. 12F and 12I) individual precursor ion mass spectra recorded during the same LC-MS/MS analysis (FIGS. 12D-12F, precursors of 482.16, corresponding to the thiolated ion of QL47; FIGS. 12G-12I, precursors of 394.16, corresponding to the $iy_1$ ion of QL47; abbreviated as "Prec"). Arrow indicates the elution time (FIGS. 12D, 12E, 12G, and 12H) or precursor ion signal (FIGS. 12F and 12I) for the labeled peptide. (FIGS. 12C, 12F, and 12I) The % values in each panel represent the gas phase enrichment, calculated as the relative contribution of each ion (arrow) as compared to the total ion current in that spectrum. (FIG. 12J) Proposed structures and calculated masses of the QL47 thiolated (left) and $iy_1$ (right) ions.

In FIG. 13A, each test compound is reacted with β-mercaptoethanol or other nucleophilic thiol reagent (e.g., glutathione, 2-mercaptobenzoic acid, hydrogen sulfide, etc.) to form an inactivated test compound. In some embodiments, chemically-modified test compounds are treated with desthiobiotin (DTB)-PEG3-azide in the presence of copper, TCEP, and ligand (for example TBTA) to promote copper catalyzed azide-alkyne cycloaddition (CuCAAC) resulting in the attachment of a desthiobiotin affinity tag. MS/MS of the inactivated test compound will generate test compound-specific thiolated ions in the gas phase. MS/MS/MS performed on these thiolated ions generates reference spectra for thiolated ions derived from each test compound. Reference spectra are then assembled into a spectral library database using standard software tools such as those available from the National Institute of Standards and Technology (NIST) (chemical structures are provided for illustrative purposes). In FIG. 13B, each chemically-modified test compound is reacted with β-mercaptoethanol or other nucleophilic thiol reagent (e.g., glutathione, 2-mercaptobenzoic acid, hydrogen sulfide, etc.) to form an inactivated, chemically-modified test compound. For test compounds which are chemically-modified to contain an alkyne moiety, one of several bio-orthogonal strategies, such as click-chemistry or the Staudinger ligation, may be used to incorporate an affinity tag (e.g., a desthiobiotin affinity tag). MS/MS of the chemically-modified, inactivated test compound will generate test compound-specific thiolated ions in the gas phase. MS/MS/MS performed on these thiolated ions generates reference spectra for thiolated ions derived from each chemically-modified test compound. Reference spectra are then assembled into a spectral library database using standard software tools such as those available from the National Institute of Standards and Technology (NIST) (chemical structures are provided for illustrative purposes).

In FIG. 14A, individual cell cultures are first incubated with increasing concentrations of test compound. After removal of excess test compound, cells are lysed and proteins digested with trypsin or other endoprotease. Resulting peptides are labeled with TMT or other multiplexed stable isotope reagents. Mass spectrometry data acquisition is performed as described in FIG. 15 (chemical structures are for illustrative purposes). In FIG. 14B, individual cell cultures are first incubated with increasing concentrations of test compound as shown in FIG. 14A. Next, individual cell cultures are incubated with a fixed concentration of a chemically-modified analog of each of the native (i.e., not chemically-modified) test compounds used in the first incubation step (native and chemically-modified test compounds are represented as different colored shapes). Excess test and chemically-modified test compounds are removed, and cells are lysed. For test compounds which are chemically-modified to contain an alkyne moiety, one of several bio-orthogonal strategies, such as click-chemistry or the Staudinger ligation, may be used to incorporate an affinity tag (e.g., a desthiobiotin affinity tag). In some embodiments, protein lysates are treated with desthiobiotin (DTB)-PEG3-azide in the presence of copper, TCEP, and ligand (for example TBTA) to promote copper catalyzed azide-alkyne cycloaddition (Cu-CAAC) resulting in the attachment of a desthiobiotin affinity tag to every protein irreversibly bound by a chemically-modified test compound. Desthiobiotin-tagged proteins can be enriched by use of avidin or streptavidin beads and the enriched set of proteins is digested with trypsin or other endoprotease. The digestion step may be performed either on bead-bound proteins or after elution of proteins from the avidin or streptavidin beads. The resulting peptides are labeled with TMT or other multiplexed stable isotope reagents. Mass spectrometry data acquisition is performed as described in FIG. 15. Alternatively, after steps 1-5, proteins can be digested and DTB tagged peptides enriched using avidin or streptavidin beads. After elution, peptides are labeled with TMT or other multiplexed stable isotope reagents and mass spectrometry data acquisition is performed as described in FIG. 15.

DETAILED DESCRIPTION

Figure 1A:
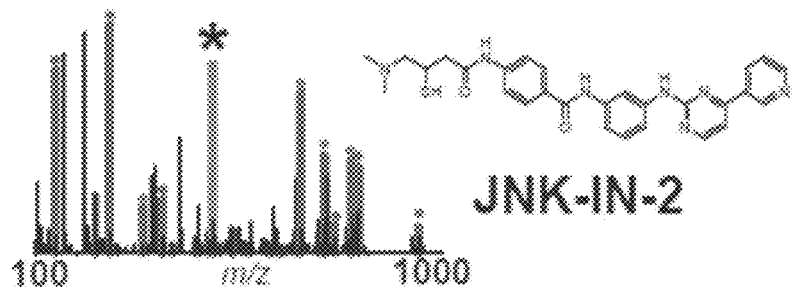
FIGS. 1A-1C show acrylamide kinase inhibitor/target conjugates generate predictable thiolated ions. MS/MS spectra for (FIG. 1A) JNK-IN-2 labeled JNK1 peptide.
Figure 1B:
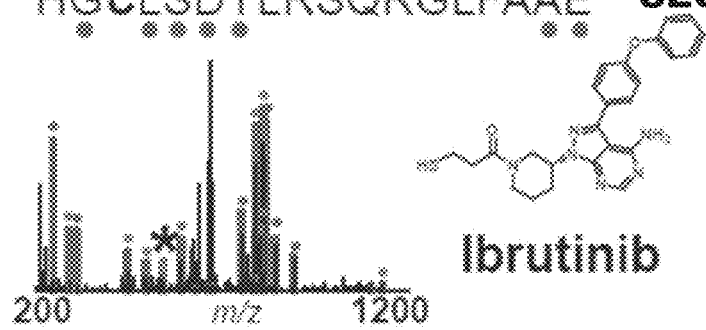
Figure 1C:
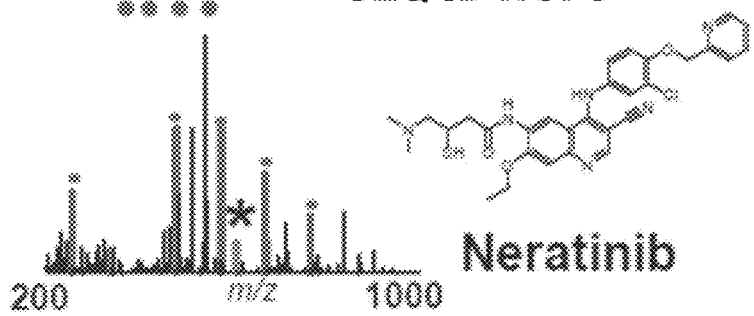

Selective covalent inhibitors which utilize diverse reactive 'warheads' have been developed for numerous enzyme families. A subset of these has been successfully produced to yield clinical-grade probes targeting kinases deubiquitinating enzymes and other catalytically active proteins. Despite these promising results the characterization of on-/off-target molecules for lead compounds, in addition to subsequent medicinal chemistry optimization remains a significant challenge. Mass spectrometry is an integral component of analytical platforms used to characterize covalent probes. Several approaches have been developed that rely on direct detection of targets based on affinity-tagged probes or the use of broad-reactivity reagents in a competition format with native inhibitors to provide an indirect readout of targets. Although informative, these approaches may be limited by (i) the use of tagged analogues which may not faithfully reproduce the physicochemical properties of the native probe or (ii) stochastic properties of shotgun LC-MS/MS whereby low-expression targets or those labeled at low-stoichiometry are not reproducibly detected or quantified.

The present application describes that cysteine side chains covalently modified via a thioether linkage exhibit common gas-phase fragmentation pathways. As described herein, these inhibitor-specific fragment ions have been leveraged to (i) significantly improve identification of modified peptides via commercial search algorithms and, (ii) facilitate selective detection of inhibitor-modified peptides in complex mixtures.

The fragmentation behavior is specific to each probe. As a result, a set or library of probes provides a means to chemically encode target proteins or other biomolecules. The combination of this chemically encoded diversity with isobaric stable isotope labeling provides, for example, a means to achieve multiplexing for discovery experiments whereby mass spectrometry is used to characterize proteins or other biomolecules irreversibly bound by covalent probes.

In addition, the gas phase fragmentation behavior specific to each probe can be used to develop targeted mass spectrometry assays to provide a high-throughput readout of target engagement stoichiometry. These assays have applicability in drug discovery, for example, biochemical characterization of lead compounds, use in pre-clinical models, clinical trials, and as standard clinical assays in point-of-care settings.

Accordingly, the present application provides, inter alia, analytical method for identifying whether a test compound irreversibly bonds to a polypeptide based on the detection of one or more thiolated or other inhibitor-specific fragment ions in a mass spectrometry assay.

In some embodiments, the analytical method comprises:
  i) contacting or reacting a test compound with a polypeptide to form a test compound-polypeptide conjugate;
  ii) analyzing the test compound-polypeptide conjugate using a mass spectrometry assay;
  iii) detecting thiolated or other inhibitor-specific ions (e.g., derivative ions thereof described herein) produced in the mass spectrometry assay; and
  iv) identifying that the test compound irreversibly bonds to the polypeptide based on the detection of the thiolated or other inhibitor-specific ions (e.g., derivative ions thereof described herein) in the mass spectrometry assay.

As used herein, the term "thiolated ions" refers to one or more ions formed in the mass spectrometry assays described herein corresponding to cleavage of a polypeptide-test compound conjugate, wherein the thiolated ion corresponds to a thiol-derivative of the test compound (e.g., a thiol-derivative of the kinase inhibitor or a thiol-derivative of the deubiquitinase inhibitor).

As used herein, the term "derivative ions" refers to fragment ions of the test compound-polypeptide conjugates that are formed during the mass spectrometry assays described in the methods provided herein. Exemplary "derivative ions" may be formed, for example, due to various intramolecular elimination reactions such as the cleavage of amide bonds within a test compound.

As used herein, the term "acrylamide-thiolated derivatives" refers to an acrylamide compound (e.g., an acrylamide test compound) which has been reacted with a thiol containing reagent to form an inactivated thioether conjugate (e.g., a test compound-thioether conjugate).

In some embodiments, the present application provides analytical methods for identifying whether a test compound irreversibly bonds to a polypeptide based on the detection of one or more thiolated ions in a mass spectrometry assay.

In some embodiments, the analytical method comprises:
  i) contacting a test compound with a polypeptide to form a test compound-polypeptide conjugate;
  ii) analyzing the test compound-polypeptide conjugate using a mass spectrometry assay;
  iii) detecting one or more thiolated ions produced in the mass spectrometry assay; and
  iv) identifying that the test compound irreversibly bonds to the polypeptide based on the detection of the one or more thiolated ions in the mass spectrometry assay.

In some embodiments, the compound-polypeptide conjugate comprises one or more thioether bonds between the test compound and the polypeptide. In some embodiments, the compound-polypeptide conjugate comprises one thioether bond between the test compound and the polypeptide. In some embodiments, the compound-polypeptide conjugate comprises more than one (e.g., two, three, or four) thioether bond between the test compound and the polypeptide.

In some embodiments, the irreversible bond is an irreversible covalent bond.

In some embodiments, step i) comprises contacting the test compound and the polypeptide in the presence of a first solvent component. In some embodiments, the first solvent component comprises one or more aprotic solvents. In some embodiments, the first solvent component comprises a single solvent. In some embodiments, the first solvent component comprises a single aprotic solvent. In some embodiments, the first solvent component is DMSO.

In some embodiments, step i) comprises treating cells growing in culture media with the test compound. In some embodiments, the culture media is RPMI-1640. In some embodiments, the culture media is DMEM-F12. In some embodiments, the culture media further comprises FBS.

In some embodiments, step i) comprises treating cell lysates with the test compound. In some embodiments, the lysates are prepared with NP-40. In some embodiments, lysates are prepared with Triton X-100.

In some embodiments, step i) further comprises contacting the compound and the polypeptide in the presence of a buffer agent. Example buffer agents include, but are not limited to, carbonate buffer agents, bicarbonate buffer agents, phosphate buffer agents, citric acid/citrate buffer agents, ammonium formate, 3-[[1,3-dihydroxy-2-(hydroxymethyl)propan-2-yl]amino]propane-1-sulfonic acid (TAPS), bicine, 2-amino-2-hydroxymethyl-propane-1,3-diol (Tris), tricine, 3-[[1,3-dihydroxy-2-(hydroxymethyl)propan-2-yl]amino]-2-hydroxypropane-1-sulfonic acid (TAPSO), 2-[4-(2-hydroxyethyl)piperazin-1-yl]ethanesulfonic acid (HEPES), 2-[[1,3-dihydroxy-2-(hydroxymethyl)propan-2-yl]amino]ethanesulfonic acid (TES), 3-Morpholinopropane-1-sulfonic acid (MOPS), 1,4-Piperazinediethanesulfonic acid (PIPES), and 2-morpholin-4-ylethanesulfonic acid (2-morpholin-4-ylethanesulfonic acid). In some embodiments, the buffer agent is triethylammonium bicarbonate. In some embodiments, the buffer agent comprises TRIS and ammonium format.

In some embodiments, step i) is performed at a temperature of about 4° C. to about 100° C., for example, about 4° C. to about 100° C., about 4° C. to about 80° C., about 4° C. to about 40° C., about 4° C. to about 30° C., about 4° C. to about 20° C., about 20° C. to about 100° C., about 20° C. to about 80° C., about 20° C. to about 60° C., about 20° C. to about 40° C., about 20° C. to about 30° C., about 30° C. to about 100° C., about 30° C. to about 80° C., about 30° C. to about 60° C., about 30° C. to about 40° C., about 40° C. to about 100° C., about 40° C. to about 80° C., about 40° C. to about 60° C., about 60° C. to about 100° C., about 60° C. to about 80° C., or about 80° C. to about 100° C. In some embodiments, step i) is performed at a temperature of about 30° C. to about 65° C. In some embodiments, step i) is performed at a temperature of about room temperature. In some embodiments, step i) is performed at a temperature below room temperature.

In some embodiments, step i) is performed for about 1 minute to about 48 hours, for example, from about 1 minute to about 48 hours, about 10 minute to about 24 hours, about 1 minute to about 18 hours, about 1 minute to about 16 hours, about 1 minute to about 12 hours, about 1 minute to about 8 hours, about 1 minute to about 1 hours, about 1 hour to about 18 hours, about 1 hour to about 16 hours, about 1 hour to about 12 hours, about 1 hour to about 8 hours, about 8 hours to about 24 hours, about 8 hours to about 18 hours, about 8 hours to about 16 hours, about 8 hours to about 12 hours, about 12 hours to about 24 hours, about 12 hours to about 18 hours, about 12 hours to about 16 hours, about 16 hours to about 24 hours, about 16 hours to about 18 hours, or about 18 hours to about 24 hours. In some embodiments, step i) is performed for about 8 hours to about 16 hours.

In some embodiments, step i) is performed using a molar excess of the test compound compared to the polypeptide. In some embodiments, the molar ratio of the test compound to the polypeptide is from about 0.1:1 to about 100:1, for example, from about 0.1:1 to about 100:1, from about 0.1:1 to about 50:1, from about 0.1:1 to about 25:1, from about 0.1:1 to about 20:1, from about 0.1:1 to about 15:1, from about 0.1:1 to about 10:1, from about 0.1:1 to about 2:1, from about 0.1:1 to about 1:1, from about 1:1 to about 100:1, from about 1:1 to about 50:1, from about 1:1 to about 25:1, from about 1:1 to about 20:1, from about 1:1 to about 15:1, from about 1:1 to about 10:1, from about 1:1 to about 2:1, from about 2:1 to about 100:1, from about 2:1 to about 50:1, from about 2:1 to about 25:1, from about 2:1 to about 20:1, from about 2:1 to about 15:1, from about 2:1 to about 10:1, from about 10:1 to about 100:1, from about 10:1 to about 50:1, from about 10:1 to about 25:1, from about 10:1 to about 20:1, from about 10:1 to about 15:1, from about 15:1 to about 100:1, from about 15:1 to about 50:1, from about 15:1 to about 25:1, from about 15:1 to about 20:1, from about 20:1 to about 100:1, from about 20:1 to about 50:1, from 20:1 to about 25:1, from about 25:1 to about 100:1, from about 25:1 to about 50:1, or from about 50:1 to about 100:1. In some embodiments, the molar ratio of the test compound to the polypeptide is from about 5:1 to about 15:1.

In some embodiments, the methods provided herein further comprise preparing the test compound-polypeptide conjugate for mass spectrometry analysis. For example, this preparation may involve one or more steps of chromatography (e.g., ion exchange, reversed phase) and exchange into a suitable solvent. In some embodiments, the reaction mixture may be diluted in a suitable solvent (e.g., 30% acetonitrile with 0.1% acetic acid) and injected directly into the mass spectrometer.

In some embodiments, the method provided herein further comprises contacting the test compound-polypeptide conjugate with an acid in the presence of a second solvent component prior to performing the mass spectrometry assay of step ii). Example acids can be inorganic or organic acids and include, but are not limited to, strong and weak acids. Some strong acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. In some embodiments, the acid is an organic acid. In some embodiments, the acid is acetic acid.

In some embodiments, the second solvent component comprises one or more aprotic solvents. In some embodiments, the second solvent component comprises a single solvent. In some embodiments, the second solvent component comprises a single aprotic solvent. In some embodiments, the second solvent component comprises acetonitrile. In some embodiments, the second solvent component further comprises one or more protic solvents. In some embodiments, the second solvent component further comprises water.

In some embodiments, the method provided herein further comprises digesting the test compound-polypeptide conjugate prior to the performing the mass spectrometry assay of step ii). In some embodiments, the resulting compound-peptide conjugates are useful for traditional shotgun and/or targeted mass spectrometry assays (e.g., MRM, SRM, precursor ion, and the like).

In some embodiments, the digesting is performed in the presence of a digestive enzyme. In some embodiments, the digesting comprises reacting the test compound-polypeptide conjugate with trypsin or another proteolytic enzyme in the presence of a third solvent component.

In some embodiments, the third solvent component comprises ammonium bicarbonate. In some embodiments, the third solvent component comprises aqueous ammonium bicarbonate. In some embodiments, the third solvent component comprises 100 mM ammonium bicarbonate in water.

In some embodiments, proteins from cells and/or lysates are prepared for mass spectrometry analysis as described herein. For example, detergents are removed before or after digestion and proteins are reduced and alkylated. In some embodiments, proteins and/or lysates may be treated with one or more chaotropic agents (e.g., Urea/GuHCl). In some embodiments, the proteins and/or lysates may be digested with a proteolytic enzyme (e.g., trypsin, GluC, AspN, pepsin, trypN, elastase, ArgC, and chymotrypsin). In some embodiments, the proteins and/or lysates may be chemically digested (e.g., with cyanogen bromide or hydroxylamine). In some embodiments, the proteins and/or lysates may be desalted (e.g., by reversed phase). In some embodiments, the detergent may be removed by acetone precipitation, trizol extraction, ion exchange chromatography, or other solid phase extraction techniques commonly used in the field.

In some embodiments, the polypeptide comprises one or more amino acids residues comprising at least one sulfur atom. In some embodiments, the polypeptide comprises one or more cysteine residues. In some embodiments, the polypeptide comprises one cysteine residue. In some embodiments, the polypeptide comprises more than one cysteine residue.

In some embodiments, the test compound comprises one or more functional groups comprising at least one sulfur atom. In some embodiments, the test compound comprises one or more cysteine groups. In some embodiments, the test compound comprises one cysteine group. In some embodiments, the test compound comprises more than one cysteine group. In some embodiments the test compound may contain one or more amino acids or linked amino acids in addition to one or more functional groups containing at least one sulfur atom.

In some embodiments, the test compound is capable of irreversibly bonding to at least one of the one or more amino acids residues comprising at least one sulfur atom in the polypeptide. In some embodiments, the test compound is capable of irreversibly bonding to one or more cysteine residues of the polypeptide. In some embodiments, the test compound is capable of irreversibly bonding to one of the cysteine residues of the polypeptide. In some embodiments, the test compound is capable of irreversibly bonding to more than one of the cysteine residues of the polypeptide.

In some embodiments, the test compound comprises one or more groups capable of forming thioether bonds with the polypeptide (e.g., with one or more cysteine residues in the polypeptide). In some embodiments, the test compound comprises one or more acrylamide groups (e.g., a substituted or unsubstituted acrylamide group). In some embodiments, the test compound comprises one or more acrylamide groups, dimethylamino acrylamide groups, iodoacetamide groups, chloroacetamide groups, maleimide groups, or reactive C—X groups, wherein X is a halogen. In some embodiments, the test compound is isotopically labeled with heavy isotopes of carbon, oxygen, nitrogen, sulfur, phosphorous, chlorine, bromine, or hydrogen. In some embodiments, the test compound comprises one or more groups selected from the group consisting of an acrylate group, a cyanoacrylamide group, a cyanoacrylate group, and a haloacetamide group. In some embodiments, the test compound comprises one or more chloroacetamide groups (e.g., a substituted or unsubstituted chloroacetamide). As used here, the term "acrylamide" refers to a group of Formula I or Formula II:

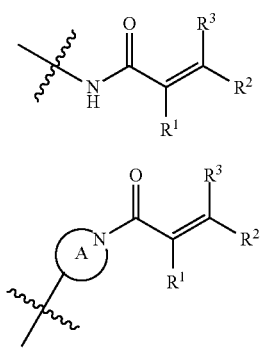

wherein $R^1$, $R^2$, and $R^3$ are each independently selected from the group consisting of H, $C_{1-6}$ alkyl, $C_{2-6}$ alkenyl, $C_{2-6}$ alkynyl, amino, $C_{1-6}$ alkylamino, and di($C_{1-6}$ alkyl)amino; and wherein ring A of Formula II represented a 4-20 membered heterocycloalkyl or a 5-20 membered heteroaryl group, each of which may be optionally substituted.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency. Suitable substituents include, but are not limited to, $C_{1-6}$ alkyl, $C_{2-6}$ alkenyl, $C_{2-6}$ alkynyl, amino, $C_{1-6}$ alkylamino, and di($C_{1-6}$ alkyl)amino.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "Cn-m" indicates a range which includes the endpoints, wherein n and m are integers and indicate the number of carbons. Examples include $C_{1-4}$, $C_{1-6}$, and the like.

As used herein, the term "Cn-m alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "Cn-m alkenyl" refers to an alkyl group having one or more carbon-carbon double bonds and having n to m carbons. Example alkenyl groups include, but are not limited to, ethenyl, allyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "Cn-m alkynyl" refers to an alkyl group having one or more carbon-carbon triple bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "amino" refers to a group of formula —$NH_2$.

As used herein, the term "Cn-m alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di(Cn-m-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "non-selective thiol-reactive compound" or "compound having broad thiol reactivity" refers to a compound comprising one or more moieties that are non-selectively reactive towards a thiol group (e.g., —SH). Exemplary moieties having reactivity towards a thiol group include, but are not limited to, acrylamide, dimethylamino acrylamide, iodoacetamide, chloroacetamide, maleimide, and C—X groups, wherein X is a halogen. In some embodiments, the non-selective thiol-reactive compound is labeled (e.g., radiolabeled) with heavy isotopes of carbon, oxygen, nitrogen, sulfur, phosphorous, chlorine, bromine, or hydrogen. In some embodiments, the non-selective thiol-reactive compound or compound having broad thiol reactivity comprises one or more acrylamide groups, dimethylamino acrylamide groups, iodoacetamide groups, chloroacetamide groups, maleimide groups, C—X groups, or any combination thereof, wherein X is a halogen.

In some embodiments, the test compound comprises one acrylamide group. In some embodiments, the test compound comprises more than one acrylamide group. In some embodiments, the test compound comprises one or more terminal acrylamide groups.

In some embodiments, the test compound comprises one haloacetamide group. In some embodiments, the test compound comprises more than one haloacetamide group. In some embodiments, the test compound comprises one or more terminal haloacetamide groups.

In some embodiments, the test compound comprises one electrophilic group. In some embodiments, the test compound comprises more than one electrophilic group. In some embodiments, the test compound comprises one or more terminal electrophilic groups.

In some embodiments, the test compound is chemically modified to facilitate affinity-based enrichment of test compound polypeptide conjugates. In some embodiments chemical-modification of the test compound comprises an affinity tag such as a peptide-epitope, biotin, or desthiobiotin. In some embodiments the chemical-modification of the test compound comprises a bio-orthogonal moiety such as an alkyne or azide.

In some embodiments, the polypeptide comprises one or more groups capable of forming thioether bonds with the test compound (e.g., with one or more sulfur atoms in the test compound). In some embodiments, the polypeptide comprises one or more groups capable of forming covalent thioether bonds with the test compound. In some embodiments, the polypeptide comprises one or more acrylamide groups. In some embodiments, the polypeptide comprises one acrylamide group. In some embodiments, the polypeptide comprises more than one acrylamide group. In some embodiments, the polypeptide comprises one or more terminal acrylamide groups.

In some embodiments, the test compound is identified as a kinase inhibitor or a deubiquitinase inhibitor (e.g., TL11-113). In some embodiments, the test compound is identified as a kinase inhibitor. Example kinase inhibitors include, but are not limited to, JNK-IN-7, HBX-19818, MI-2, TL10-201, THZ531, THZ1, QL-47, ibrutinib, neratinib, afatinib, axitinib, bosutinib, cobimetinib, crizotinib, entrectinib, erlotinib, and the like. In some embodiments, the test compound is selected from the group consisting of JNK-IN-7, HBX-19818, MI-2, TL10-201, THZ531, THZ1, QL-47, ibrutinib, and neratinib. In some embodiments, the test compound is selected from the group consisting of JNK-IN-7, HBX-19818, MI-2, TL10-201, THZ531, THZ1, QL-47, TL11-113, ibrutinib, and neratinib.

In some embodiments, a reagent having broad thiol reactivity and high yield of thiolated ions, or derivative ions thereof, is used to measure the binding stoichiometry of the test compound to its target. In some embodiments, the reagent with broad thiol reactivity and high yield of thiolated ions, or derivative ions thereof, is selected from the group consisting of:

2-iodo-1-morpholinoethan-1-one;
1-((2R,6R)-2,6-dimethylmorpholino)-2-iodoethan-1-one;
1-((2R,6S)-2,6-dimethylmorpholino)-2-iodoethan-1-one;
1-(2,2-dimethylmorpholino)-2-iodoethan-1-one;
1-(3,5-dimethylmorpholino)-2-iodoethan-1-one;
1-(hexahydrocyclopenta[b][1,4]oxazin-4(4aH)-yl)-2-iodoethan-1-one;
1-(2,3-dihydro-4H-benzo[b][1,4]oxazin-4-yl)-2-iodoethan-1-one;
N-(4-cyanophenyl)-2-iodoacetamide;
N-(2,5-dimethylphenyl)-2-iodoacetamide;
N-(2,5-dimethoxyphenyl)-2-iodoacetamide;
2-iodo-N-phenylacetamide;
2-iodo-N-(p-tolyl)acetamide;
2-iodo-1-(4-methylpiperazin-1-yl)ethan-1-one 2,2,2-trifluoroacetate;
N-(furan-2-ylmethyl)-2-iodoacetamide;
2-iodo-N-(1-methyl-1H-imidazol-4-yl)acetamide; and
N-ethylmaleimide.

In some embodiments, the reagent having broad thiol reactivity is isotopically labeled with heavy isotopes of carbon, oxygen, nitrogen, sulfur, phosphorous, chlorine, bromine, or hydrogen.

In some embodiments, the polypeptide is a protein or a protein fragment. In some embodiments, the polypeptide is a protein. In some embodiments, the polypeptide is a protein fragment.

In some embodiments, the polypeptide is a protein or protein fragment comprising from about 4 to about 100 amino acid residues, for example, from about 4 to about 100, about 4 to about 80, about 4 to about 60, about 4 to about 40, about 4 to about 20, about 4 to about 10, about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 amino acid residues. In some embodiments, the polypeptide is a protein or protein fragment comprising from about 10 to about 30 amino acid residues. In some embodiments, the polypeptide is a protein comprising from about 10 to about 30 amino acid residues. In some embodiments, the polypeptide is a protein fragment comprising from about 10 to about 30 amino acid residues. In some embodiments, the polypeptide is a kinase or a kinase fragment. In some embodiments, the polypeptide is a kinase. In some embodiments, the polypeptide is a kinase fragment.

In some embodiments, the polypeptide is a kinase, a kinase fragment, a deubiquitinase, or a deubiquitinase fragment. In some embodiments, the polypeptide is a kinase or deubiquitinase selected from the group consisting of JNK2, JAK3, CDK7, CDK12, TAK1, ITK, USP-7, and EGFR, or a fragment thereof.

In some embodiments, the polypeptide is a kinase selected from the group consisting of JNK2, JAK3, CDK7, CDK12, ITK, USP-7, and EGFR, or a fragment thereof. In some embodiments, the polypeptide is a kinase or a kinase fragment comprising from about 10 to about 100 amino acid residues, for example, from about 10 to about 100, about 10 to about 80, about 10 to about 60, about 10 to about 40, about 10 to about 20, about 20 to about 100, about 20 to about 80, about 20 to about 60, about 20 to about 40, about 40 to about 100, about 40 to about 80, about 40 to about 60, about 60 to about 100, about 60 to about 80, or about 80 to about 100 amino acid residues. In some embodiments, the polypeptide is a kinase or a kinase fragment comprising from about 10 to about 30 amino acid residues.

In some embodiments, the polypeptide comprises an amino acid sequence having at least 90% sequence identity to a sequence selected from the group consisting of:

(SEQ ID NO: 1)
L-M-D-A-N-L-C-Q-V-I-Q-M-E;

(SEQ ID NO: 2)
L-V-M-E-Y-L-P-S-G-C-L-R;

(SEQ ID NO: 3)
M-A-P-P-D-L-P-H-W-Q-D-C-H-E-L-W-S-K;

(SEQ ID NO: 4)
H-G-C-L-S-D-Y-L-R-S-Q-R-G-L-F-A-A-E;

(SEQ ID NO: 5)
Y-F-S-N-R-P-G-P-T-P-G-C-Q-L-P-R-P-N-C-P-V-E-T-L-K;

(SEQ ID NO: 6)
G-C-L-L-D-Y-V-R;

(SEQ ID NO: 7)
F-G-L-C-S-G-P-A-D-T-G-R;

(SEQ ID NO: 8)
Y-M-A-N-G-C-L-sL-N-Y-L-R;

(SEQ ID NO: 9)
I-C-D-F-G-T-A-C-D-I-Q-T-H-M-T-N-N-K;
and (SEQ ID NO: 10)
Y-F-S-N-R-P-G-P-T-P-G-C-Q-L-P-(13C6-15N4)R-P-N-C-P-V-E-T-L-K.

In some embodiments, the polypeptide comprises an amino acid sequence having at least 90% sequence identity to a sequence selected from the group consisting of:

L-M-D-A-N-L-C-Q-V-I-Q-M-E; (SEQ ID NO: 1)

L-V-M-E-Y-L-P-S-G-C-L-R; (SEQ ID NO: 2)

M-A-P-P-D-L-P-H-W-Q-D-C-H-E-L-W-S-K; (SEQ ID NO: 3)

H-G-C-L-S-D-Y-L-R-S-Q-R-G-L-F-A-A-E; (SEQ ID NO: 4)

Y-F-S-N-R-P-G-P-T-P-G-C-Q-L-P-R-P-N-C-P-V-E-T-L-K; (SEQ ID NO: 5)

G-C-L-L-D-Y-V-R; (SEQ ID NO: 6)

F-G-L-C-S-G-P-A-D-T-G-R; (SEQ ID NO: 7)
and

Y-M-A-N-G-C-L-sL-N-Y-L-R. (SEQ ID NO: 8)

In some embodiments, the polypeptide comprises an amino acid sequence having at least 60% (e.g., at least 70%, at least 75%, at least 80%, at least 85%, at least 90%, at least 95%, at least 99%, or 100%) sequence identity to a sequence selected from the group consisting of SEQ ID NOs:1-8.

The present application further provides an analytical method (e.g., a high throughput method), comprising:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) analyzing the third mixture using a mass spectrometry assay;
iii) detecting one or more thiolated or other compound-specific fragment ions (e.g., derivative ions as described herein) produced in the mass spectrometry assay; and
iv) identifying that one or more of the test compounds binds irreversibly to one or more of the polypeptides based on the detection of a thiolated or other inhibitor-specific fragment ion (e.g., derivative ions as described herein) in the mass spectrometry assay.
v) quantifying compound selectivity for polypeptide by varying the concentration of compound and using stable isotope labels to quantify extent of compound-polypeptide formation at each concentration.

In some embodiments, the analytical method (e.g., a high throughput method), comprises:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) analyzing the third mixture using a mass spectrometry assay;
iii) detecting one or more thiolated ions produced in the mass spectrometry assay; and
iv) identifying that one or more of the test compounds binds irreversibly to one or more of the polypeptides based on the detection of the one or more thiolated ions in the mass spectrometry assay.

In some embodiments, the analytical method (e.g., a high throughput method), comprises:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) contacting the third mixture with a fourth mixture comprising one or more chemically-modified analogs of the one or more test compounds contained in the first mixture to form a fifth mixture comprising one or more test compound-polypeptide conjugates and one or more chemically-modified test compound-polypeptide conjugates; wherein each of the test compound-polypeptide conjugates and chemically-modified test compound polypeptide conjugates comprise one or more thioether bonds;
iii) preparing a sixth mixture from the fifth mixture by application of standard click chemistry or other biorthogonal chemistry schemes to attach an affinity handle, followed by biochemical purification methods to enrich the chemically-modified, tagged test compound-polypeptide conjugates;
iv) analyzing the sixth mixture using a mass spectrometry assay;
v) detecting one or more thiolated ions produced in the mass spectrometry assay; and
vi) identifying that one or more of the chemically-modified test compounds binds irreversibly to one or more of the polypeptides based on the detection of the one or more thiolated ions in the mass spectrometry assay.

The present application further provides an analytical method (e.g., a high throughput method), comprising:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) contacting the third mixture with a fourth mixture comprising one or more chemically-modified analogs of the one or more test compounds contained in the first mixture to form a fifth mixture comprising one or more test compound-polypeptide conjugates and one or more chemically-modified test compound-polypeptide conjugates; wherein each of the test compound-polypeptide conjugates and chemically-modified test compound polypeptide conjugates comprise one or more thioether bonds;
iii) preparing a sixth mixture from the fifth mixture, wherein the sixth mixture comprises one or more chemically-modified test compound-polypeptide conjugates comprising one or more affinity tags;
iv) analyzing the sixth mixture using a mass spectrometry assay;
v) detecting one or more thiolated ions produced in the mass spectrometry assay; and
vi) identifying that one or more of the chemically-modified test compounds binds irreversibly to one or more of the polypeptides based on the detection of the one or more thiolated ions in the mass spectrometry assay.

In some embodiments, the one or more chemically-modified analogs each comprise an alkyne or azide moiety.

In some embodiments, preparation of the sixth mixture comprises reacting the one or more chemically-modified analogs of the fifth mixture under conditions of suitable for performing click chemistry or biorthogonal chemistry to attach an affinity handle to the one or more chemically-modified analogs, thereby producing the chemically-modified test compound-polypeptide conjugates comprising one or more affinity tags.

In some embodiments, the analytical method further comprising biochemically purifying the sixth mixture to enrich the sixth mixture in the chemically-modified, tagged test compound-polypeptide conjugates, prior to the analyzing of step iv).

In some embodiments, the method further comprises quantifying compound selectivity for polypeptide by varying the concentration of compound and using stable isotope labels to quantify extent of compound-polypeptide formation at each concentration.

In some embodiments, the method further comprises the use of chemically-modified analogs of each of the one or more test compounds in a competition-format, wherein the native (i.e., not chemically-modified) test compounds are first added (e.g., at varying concentration), to a mixture of one or more polypeptides. This first addition step is followed by addition of a fixed-concentration of chemically-modified analogs of each of the one or more test compounds. Standard chemical (e.g., click chemistry) and biochemical methods are used to connect affinity handles and purify chemically-modified, affinity-tagged test compound-polypeptide conjugates. In some embodiments, test compound selectivity is established by use of stable isotope labels to quantify the extent of compound-polypeptide formation at each concentration of native (i.e., not chemically-modified) test compound used.

The present application further provides an analytical method, comprising:
i) contacting a first mixture comprising one or more test compounds with a second mixture comprising one or more polypeptides to form a third mixture comprising one or more compound-polypeptide conjugates, wherein each of the compound-polypeptide conjugates comprise one or more thioether bonds;
ii) analyzing the third mixture using a mass spectrometry assay;
iii) detecting one or more thiolated ions produced in the mass spectrometry assay; and
iv) identifying that one or more of the test compounds binds irreversibly to one or more of the polypeptides based on the detection of the one or more thiolated ions in the mass spectrometry assay.

In some embodiments, the method further comprises digesting the test compound-polypeptide conjugate prior to performing the mass spectrometry assay of step ii).

In some embodiments, the digesting comprises reacting the test compound-polypeptide conjugate with trypsin or another proteolytic enzyme in the presence of a third solvent component. In some embodiments, the digesting comprises reacting the test compound-polypeptide conjugate with trypsin in the presence of a third solvent component.

In some embodiments, the third solvent component comprises a pH 7-9 buffer agent (e.g., triethylammonium bicarbonate, PBS, HEPES, and the like). In some embodiments, the third solvent component comprises ammonium bicarbonate. In some embodiments, the third solvent component comprises 100 mM ammonium bicarbonate in water. In some embodiments, the third solvent component further comprises a chaotropic agent (e.g., urea or GuHCl). In some embodiments, the third solvent component further comprises Rapigest or other mass spectrometry-compatible surfactant.

In some embodiments, the test compounds in the first mixture can be the same and/or have the same characteristics of the test compounds described above (e.g., each of the test compounds comprises one or more thiol-reactive groups including, but not limited to, acrylamide groups, dimethylamino acrylamide groups, iodoacetamide groups, chloroacetamide groups, maleimide groups, or reactive C—X groups, wherein X is a halogen). In some embodiments, each of the test compounds are encoded with heavy isotopes of carbon, oxygen, nitrogen, sulfur, phosphorous, chlorine, bromine, or hydrogen. In some embodiments, the polypeptides in the second mixture can be the same and/or have the same characteristics of the polypeptides described above.

In some embodiments, the method further comprises reacting one or more acrylamide compounds with beta-mercaptoethanol or similar Michael donor to form one or more inactivated test compound, prior to the contacting of step i).

In some embodiments, the method further comprises reacting one or more test compounds, each containing a thiol-reactive moiety, with a second compound containing a nucleophilic thiol group to form one or more test compound thioether conjugates, prior to the contacting of step i). In some embodiments, the second compound is selected from the group consisting of beta-mercaptoethanol, glutathione, 2-mercaptobenzoic acid, and hydrogen sulfide.

In some embodiments, the method further comprises reacting one or more acrylamide compounds with a thiolated compound to form one or more acrylamide thiolated derivatives, prior to the contacting of step i).

In some embodiments, the method further comprises analyzing the one or more test compound thioether conjugates in a mass spectrometry assay prior to the contacting step i). In some embodiments, analyzing the test compound thioether conjugates comprises generating a database of fragment ion spectra comprising the mass spectra of each of the one or more test compound thioether conjugates. In some embodiments, the method further comprises gas-phase isolation and fragmentation (e.g., MS/MS/MS or MS3) of the one or more of the thiolated ions, or derivative ions thereof, formed during MS/MS of the one or more test compound thioether conjugates.

In some embodiments, the method further comprises analyzing the one or more inactivated test compounds in a mass spectrometry assay.

In some embodiments, the method further comprises analyzing the one or more acrylamide thiolated derivatives in a mass spectrometry assay.

In some embodiments, analyzing the one or more inactivated test compounds comprises generating a database of mass spectral fragment ions by performing MS/MS/MS on each inactivated test compound.

In some embodiments, analyzing the one or more acrylamide thiolated derivatives comprises generating a database of fragment ion spectra comprising the mass spectra of each of the one or more acrylamide thiolated derivatives.

In some embodiments, the method further comprises gas-phase isolation and fragmentation (e.g., MS/MS/MS or MS3) of the one or more thiolated ions, or derivative ions thereof, detected in step iii).

In some embodiments, the method further comprises performing MS/MS/MS on the one or more thiolated ions detected as a result of MS/MS in step iii).

In some embodiments, the method further comprises isolating the one or more thiolated ions after the detecting of step iii).

In some embodiments, the method further comprises performing a mass spectrometry assay on the one or more isolated thiolated ions prior to the identifying of step iv).

In some embodiments, the identifying of step iv) further comprises identifying a mass spectrum in the database of fragment ion spectra (e.g., MS/MS/MS or MS3 fragment ion spectra) from the one or more test compound thioether conjugates that is substantially identical to the fragment ion spectrum derived from the gas-phase isolation and fragmentation analysis (e.g., MS/MS/MS or MS3) performed on the thiolated ion detected in step iii).

In some embodiments, the identifying of step iv) further comprises identifying a mass spectrum in the database of fragment ions derived from the inactivated test compounds that is substantially identical to the mass spectrum of the isolated thiolated ion.

In some embodiments, the identifying of step iv) further comprises identifying a mass spectrum in the database of fragment ion spectra that is substantially identical to the mass spectrum of the isolated thiolated ion. In some embodiments, the thiolated compound is β-mercaptoethanol.

In some embodiments, the first mixture comprises more than one test compound. In some embodiments, the second mixture comprises more than one polypeptide. In some embodiments, the first mixture comprises more than one test compound and the second mixture comprises more than one polypeptide.

In some embodiments, the first mixture comprises from about 2 to about 100,000 different test compounds, for example, from about 2 to about 100,000, about 2 to about 75,000, about 2 to about 50,000, about 2 to about 10,000, about 2 to about 5000, about 2 to about 1000, about 2 to about 100, about 2 to about 50, about 50 to about 100,000, about 50 to about 75,000, about 50 to about 50,000, about 50 to about 10,000, about 50 to about 5000, about 50 to about 1000, about 50 to about 100, about 100 to about 100,000, about 100 to about 75,000, about 100 to about 50,000, about 100 to about 10,000, about 100 to about 5000, about 100 to about 1000, about 1000 to about 100,000, about 1000 to about 75,000, about 1000 to about 50,000, about 1000 to about 10,000, about 1000 to about 5000, about 5000 to about 100,000, about 5000 to about 75,000, about 5000 to about 50,000, about 5000 to about 10,000, about 10,000 to about 100,000, about 10,000 to about 75,000, about 10,000 to about 50,000, about 50,000 to about 100,000, about 50,000 to about 75,000, or about 75,000 to about 100,000 test compounds.

In some embodiments, the second mixture is a biological sample, for example, a cell, a tissue, a bone, a cell sample, a tissue sample, a bone sample, and the like. In some embodiments, the second mixture is a cell sample.

In some embodiments, the first mixture and the second mixture are useful for performing a high throughput assay. The high throughput assay can be used to identify effective covalent probes for certain proteins (e.g., cysteine-containing proteins) in a cell sample.

The present application further provides an analytical method (e.g., a high throughput method) comprising:
 i) reacting one or more acrylamide compounds with a thiol-containing compound to form one or more inactivated test compounds;
 ii) analyzing the one or more inactivated test compounds in a mass spectrometry assay;
 iii) generating a database of fragment ion spectra comprising the mass spectra of each of the one or more inactivated test compounds;
 iv) contacting a first mixture comprising more than one test compound, wherein each test compound may be introduced at different concentrations, with a second mixture comprising more than one polypeptide to form a third mixture comprising more than one compound-polypeptide conjugate, wherein each of the compound-polypeptide conjugates comprise one or more thioether bonds;
 v) analyzing the third mixture using a mass spectrometry assay;
 vi) detecting one or more thiolated or other compound-specific fragment ions produced in the mass spectrometry assay;
 vii) isolating the one or more thiolated ions in the mass spectrometer;
 viii) performing a mass spectrometry assay on the one or more isolated thiolated ions;
 ix) comparing the mass spectra of the one or more thiolated ions to the database of fragment ion spectra; and
 x) identifying that one or more of the test compounds binds irreversibly to one or more of the polypeptides based on the detection of one or more thiolated ions in the mass spectrometry assay of step v) and determining that the mass spectrum in the database of fragment ion spectra is substantially identical to the mass spectrum of the isolated thiolated ion of step viii).

In some embodiments, the analytical method comprises:
 i) reacting one or more acrylamide compounds with a thiol-containing compound to form one or more acrylamide thiolated derivatives;
 ii) analyzing the one or more acrylamide thiolated derivatives in a mass spectrometry assay;
 iii) generating a database of fragment ion spectra comprising the mass spectra of each of the one or more acrylamide thiolated derivatives;
 iv) contacting a first mixture comprising more than one test compound with a second mixture comprising more than one polypeptide to form a third mixture comprising more than one compound-polypeptide conjugate, wherein each of the compound-polypeptide conjugates comprise one or more thioether bonds;
 v) analyzing the third mixture using a mass spectrometry assay;
 vi) detecting one or more thiolated ions produced in the mass spectrometry assay;
 vii) isolating the one or more thiolated ions;
 viii) performing a mass spectrometry assay on the one or more isolated thiolated ions;
 ix) comparing the mass spectra of the one or more thiolated ions to the database of fragment ion spectra; and
 x) identifying that one or more of the test compounds binds irreversibly to one or more of the polypeptides based on the detection of one or more thiolated ions in the mass spectrometry assay of step v) and the identification a mass spectrum in the database of fragment ion spectra that is substantially identical to the mass spectrum of the isolated thiolated ion of step viii).

The present application further provides an analytical method, comprising:
i) reacting one or more test compounds each containing a thiol-reactive moiety with a second compound containing a thiol group to form one or more test compound thioether conjugates;
ii) analyzing the one or more test compound thioether conjugates in a mass spectrometry assay;
iii) generating a database of fragment ion spectra comprising the mass spectra derived from the mass spectrometry assay (e.g., MS/MS/MS or MS3) performed on each of the one or more test compound thioether conjugates;
iv) contacting a first mixture comprising more than one test compound with a second mixture comprising more than one polypeptide to form a third mixture comprising more than one test compound-polypeptide conjugate, wherein each of the test compound-polypeptide conjugates comprise one or more thioether bonds;
v) analyzing the third mixture using a mass spectrometry assay;
vi) detecting one or more thiolated ions, or derivative ions thereof, produced in the mass spectrometry assay;
vii) performing gas phase isolation and MS/MS/MS or MS3 analysis on the one or more thiolated ions, or derivative ions thereof, to generate fragment ion spectra;
viii) comparing the fragment ion spectra generated in step vii) with the database of fragment ion spectra generated in step iii); and
ix) identifying that one or more of the test compounds binds irreversibly to one or more of the polypeptides based on the detection of one or more thiolated ions, or derivative ions thereof, in the mass spectrometry assay of step v) and the identification of a mass spectrum in the database of fragment ion spectra that is substantially identical to the mass spectrum of the thiolated ion, or derivative ion thereof, generated in step iii).

In some embodiments, the fragment ion spectra generated in step vii) are diagnostic of the one or more test compounds.

The gas phase fragmentation behavior specific to each probe can be used to develop targeted mass spectrometry assays. These assays may be used when the target and compound are known, for example, to validate the stoichiometry of target engagement.

Accordingly, the present application further provides an analytical method, comprising:
i) contacting a test compound with a second mixture comprising one or more polypeptides to form a third mixture comprising one or more compound-polypeptide conjugates, wherein each of the compound-polypeptide conjugates comprise one or more thioether bonds;
ii) treating separate aliquot of the second mixture with a vehicle control such as DMSO;
iii) treating both mixtures with a compound having non-selective, broad thiol reactivity, which forms a thioether linkage; examples of such compounds include acrylamide or maleimide or N-functionalized maleimide; in one embodiment the non-selective thiol reactive compounds are encoded with stable isotope labels such as $^{15}N$, $^{13}C$, or $^{18}O$;
iv) combining both mixtures; in one embodiment the target of interest is further enriched from the combined mixture using immunoaffinity capture reagents;
v) digesting the combined mixture or the enriched mixture resulting from immunoaffinity capture with trypsin or other proteolytic enzyme;
vi) analyzing the digested peptides using a targeted mass spectrometry assay;
vii) detecting one or more thiolated or other specific fragment ions produced by the thioether linkage between the target and the non-selective thiol-reactive compound in the mass spectrometry assay; and
viii) determining target engagement stoichiometry for the compound-polypeptide conjugate based on the ratio of thiolated or other specific fragment ions resulting from the non-selective, thiol-reactive compound detected in mixtures originally reacted with test compound or DMSO (e.g., vehicle control).

In some embodiments, the analytical method comprises:
i) contacting a test compound with a first mixture comprising one or more polypeptides to form a second mixture comprising one or more compound-polypeptide conjugates, wherein each of the compound-polypeptide conjugates comprise one or more thioether bonds;
ii) treating an aliquot of the first mixture with a vehicle control to form a third mixture;
iii) treating both the second and third mixtures with isotopically labeled or unlabeled broad thiol-reactive compounds to form fourth and fifth mixtures comprising one or more thioether bonds between the broad thiol reactive compounds and the one or more polypeptides;
iv) combining the fourth and fifth mixtures to form a combined mixture;
v) digesting the combined polypeptide mixture (e.g., in the presence of trypsin or a digestive enzyme such as a proteolytic enzyme) to form a mixture of (a) one or more test compound-peptide conjugates, (b) one or more broad thiol-reactive compound-peptide conjugates, and (c) one or more isotopically labeled broad thiol-reactive compound-peptide conjugates, whereby each conjugate is formed through one or more thioether bonds;
vi) analyzing the peptides using a mass spectrometry assay (e.g., a targeted mass spectrometry assay);
vii) detecting one or more thiolated ions, or derivative ions thereof, produced in the mass spectrometry assay; and
viii) determining target engagement stoichiometry for the test compound-polypeptide conjugate based on the ratio of thiolated ions, or derivative ions thereof, derived from the isotopically labeled and unlabeled broad thiol reactive compound-peptide conjugates, produced in the targeted mass spectrometry assay.

In some embodiments, the method further comprises:
iv-a) enriching the compound-polypeptide conjugate in the combined mixture using one or more immunoaffinity capture reagents, wherein step iv-a) is performed after step iv) and prior to step v).

The present application further provides an analytical method, comprising:
i) contacting a test compound with a first mixture comprising one or more polypeptides to form a second mixture comprising one or more test compound-polypeptide conjugates, wherein each of the test compound-polypeptide conjugates comprise one or more thioether bonds;
ii) treating an aliquot of the first mixture with a vehicle control to form a third mixture;

iii) treating the third mixture with a broad thiol-reactive compound to form a fourth mixture comprising one or more broad thiol-reactive compound-polypeptide conjugates formed through one or more thioether bonds;
iv) treating the second mixture with a broad thiol-reactive compound labeled with one or more stable isotopes selected from the group consisting of $^{15}N$, $^{13}C$, and $^{18}O$ to form a fifth mixture comprising one or more test compound-polypeptide conjugates and one or more isotopically labeled broad thiol-reactive compound-polypeptide conjugates, whereby each conjugate is formed through one or more thioether bonds;
v) combining the fourth and fifth mixtures to form a combined mixture;
vi) enzymatically digest the combined mixture of polypeptides and polypeptide-conjugates to form a mixture of peptides comprising a combination of (i) one or more test compound-peptide conjugates, (ii) one or more broad thiol-reactive compound-peptide conjugates, and (iii) one or more isotopically labeled broad thiol-reactive compound-peptide conjugates, whereby each conjugate is formed through one or more thioether bonds;
vi) analyzing the combined mixture of peptides using a targeted mass spectrometry assay;
vii) detecting one or more thiolated ions, or derivative ions thereof, produced in the mass spectrometry assay; and
viii) determining target engagement stoichiometry for the test compound-polypeptide conjugate based on the ratio of thiolated ions, or derivative ions thereof, derived from the isotopically labeled and unlabeled broad thiol reactive compound-peptide conjugates, produced in the targeted mass spectrometry assay.

In some embodiments, the method further comprises:
iv-a) enriching the compound-polypeptide conjugate in the combined mixture using one or more immunoaffinity capture reagents, wherein step iv-a) is performed after step iv) and prior to step v).

In some embodiments, the vehicle control is DMSO.

In some embodiments, the compound having non-selective, broad thiol reactivity comprises an acrylamide group, a maleimide group, a N-functionalized maleimide, or any combination thereof. In some embodiments, the compound having non-selective, broad thiol reactivity comprises one or more acrylamide groups, dimethylamino acrylamide groups, iodoacetamide groups, chloroacetamide groups, maleimide groups, or reactive C—X groups, wherein X is a halogen. In some embodiments, each of the test compounds are encoded with heavy isotopes of carbon, oxygen, nitrogen, sulfur, phosphorous, chlorine, bromine, or hydrogen.

In some embodiments, the compound having non-selective, broad thiol reactivity is encoded with stable isotope labels selected from the group consisting of $^{15}N$, $^{13}C$, and $^{18}O$.

The present application further provides a compound or ion described herein. In some embodiments, the compound or ion is prepared according to one or more of the methods described herein. In some embodiments, the compound or ion is selected from the group of compounds provided in Table A.

TABLE A

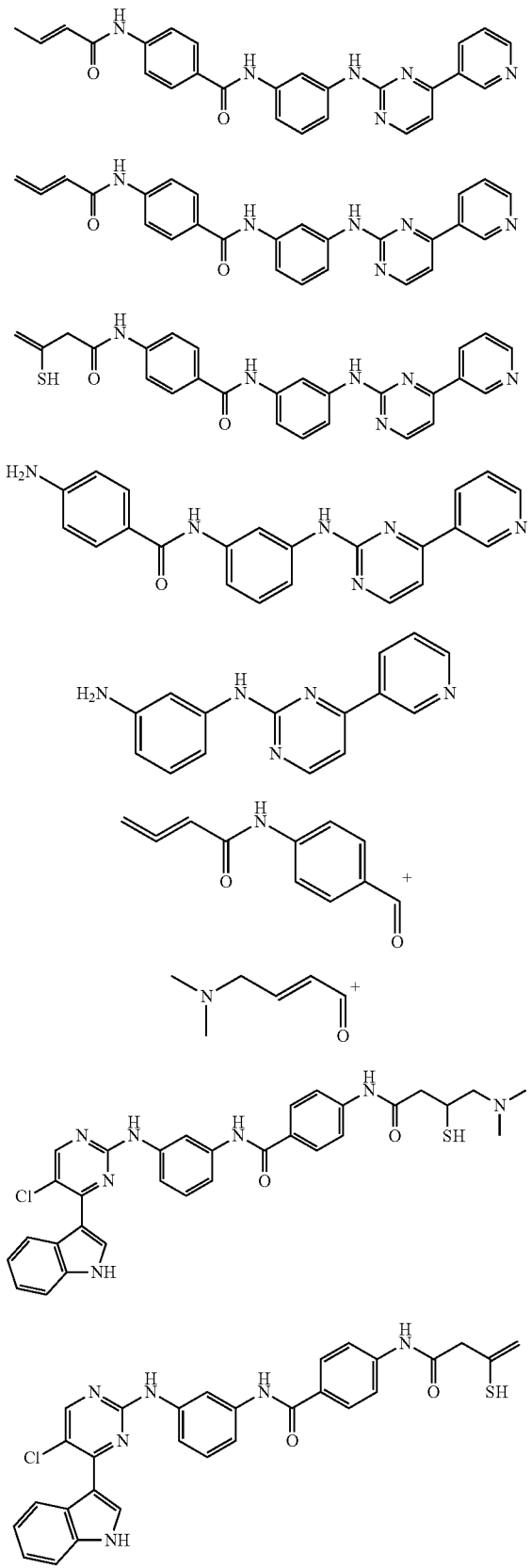

TABLE A-continued

TABLE A-continued
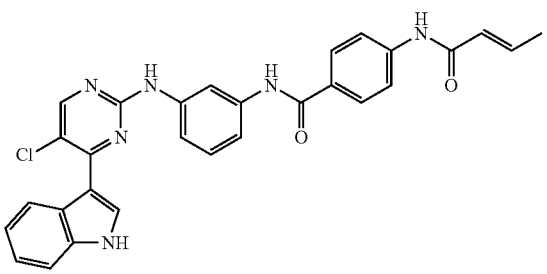 [SMILES: C/C=C/C(=O)Nc1ccc(C(=O)Nc2cccc(Nc3ncc(Cl)c(-c4c[nH]c5ccccc45)n3)c2)cc1]
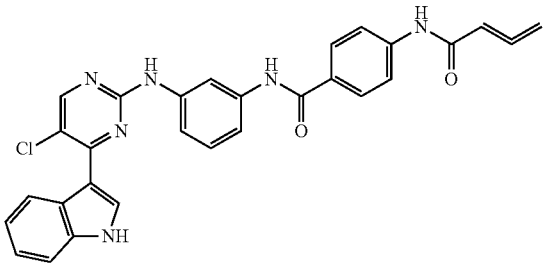 [SMILES: C=C=CC(=O)Nc1ccc(C(=O)Nc2cccc(Nc3ncc(Cl)c(-c4c[nH]c5ccccc45)n3)c2)cc1]
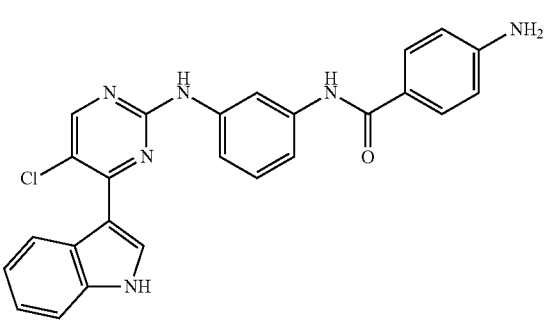 [SMILES: Nc1ccc(C(=O)Nc2cccc(Nc3ncc(Cl)c(-c4c[nH]c5ccccc45)n3)c2)cc1]
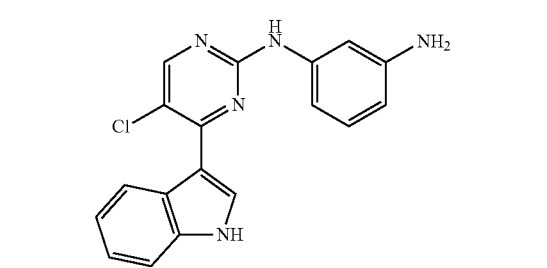 [SMILES: Nc1cccc(Nc2ncc(Cl)c(-c3c[nH]c4ccccc34)n2)c1]
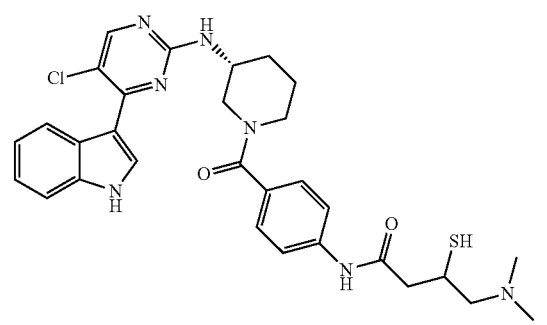 [SMILES: CN(C)CC(S)CC(=O)Nc1ccc(C(=O)N2CCC[C@@H](Nc3ncc(Cl)c(-c4c[nH]c5ccccc45)n3)C2)cc1]
TABLE A-continued
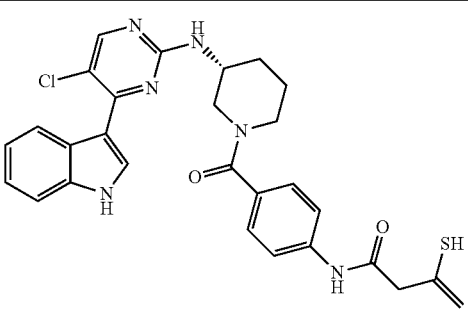
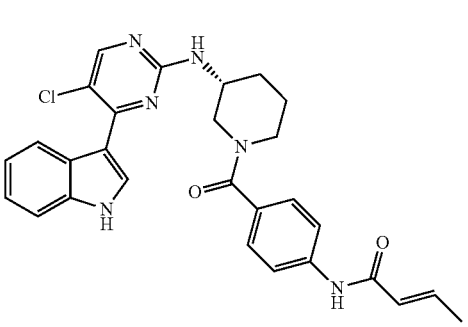 [SMILES: C/C=C/C(=O)Nc1ccc(C(=O)N2CCC[C@@H](Nc3ncc(Cl)c(-c4c[nH]c5ccccc45)n3)C2)cc1]
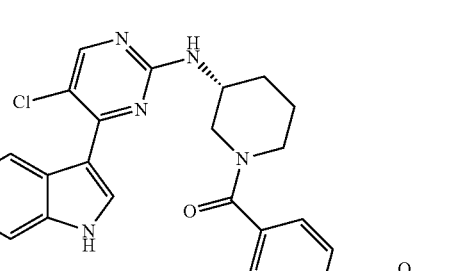
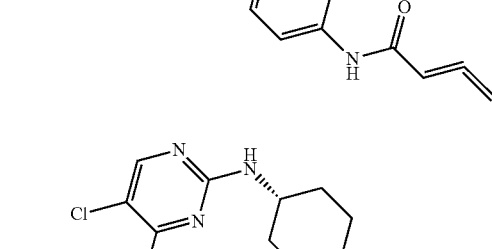
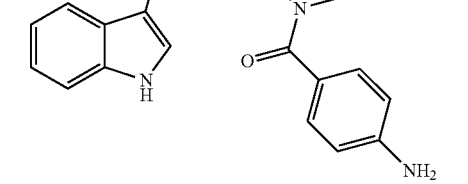
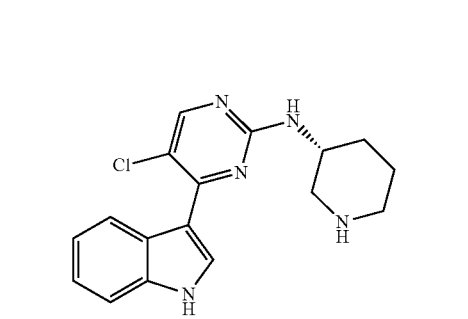 [SMILES: Clc1cnc(N[C@@H]2CCCNC2)nc1-c1c[nH]c2ccccc12]

TABLE A-continued
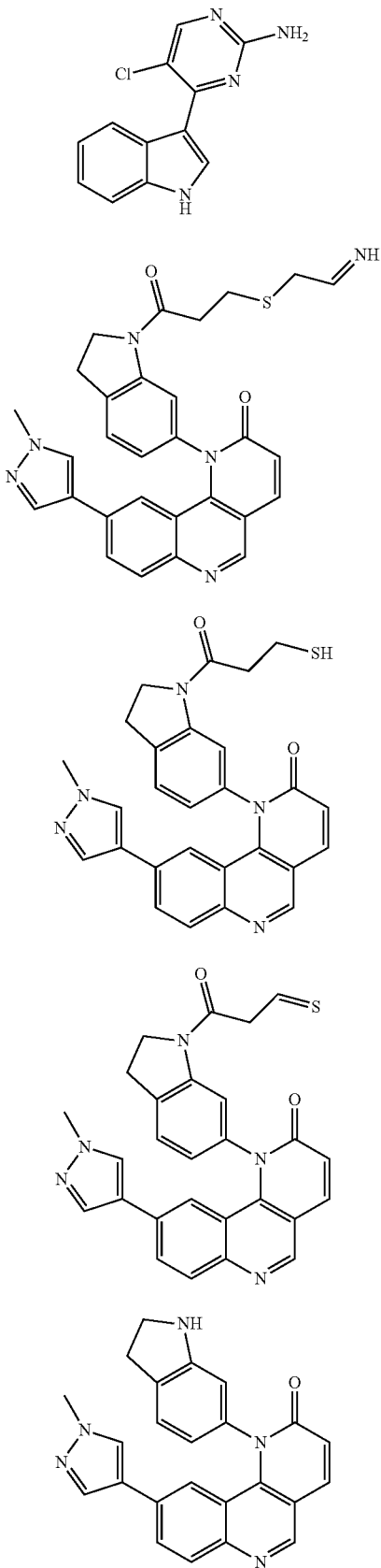
TABLE A-continued
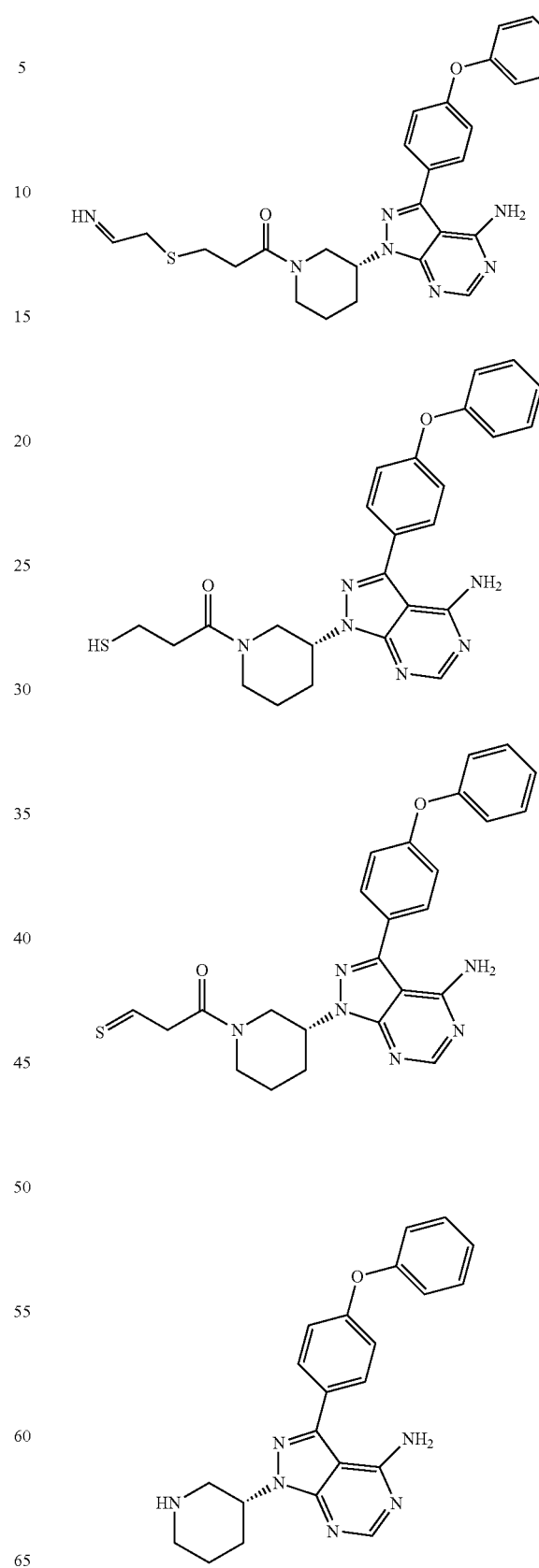

TABLE A-continued
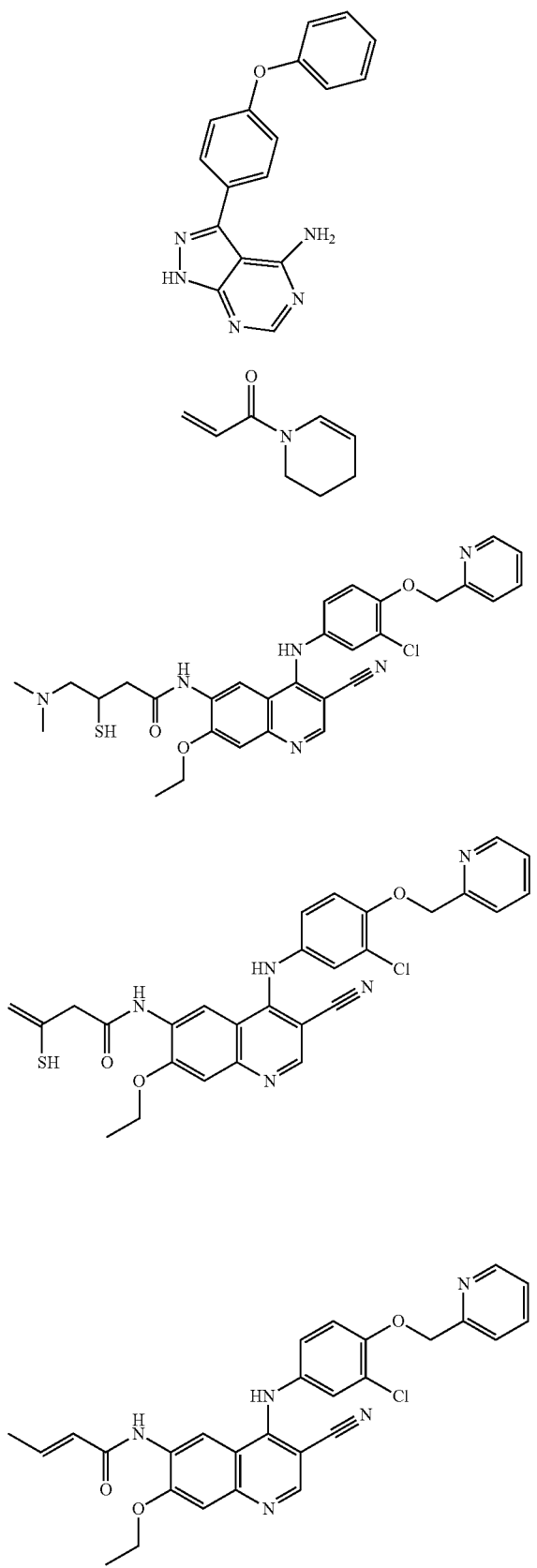
TABLE A-continued
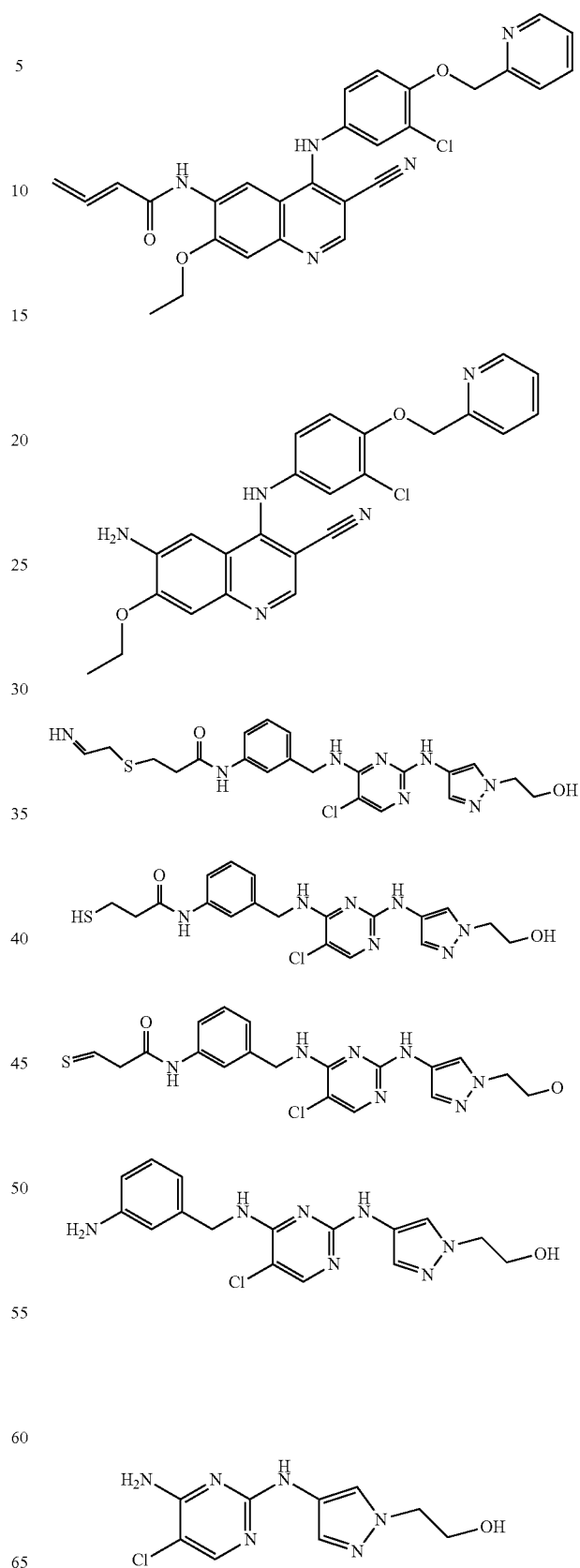

TABLE A-continued
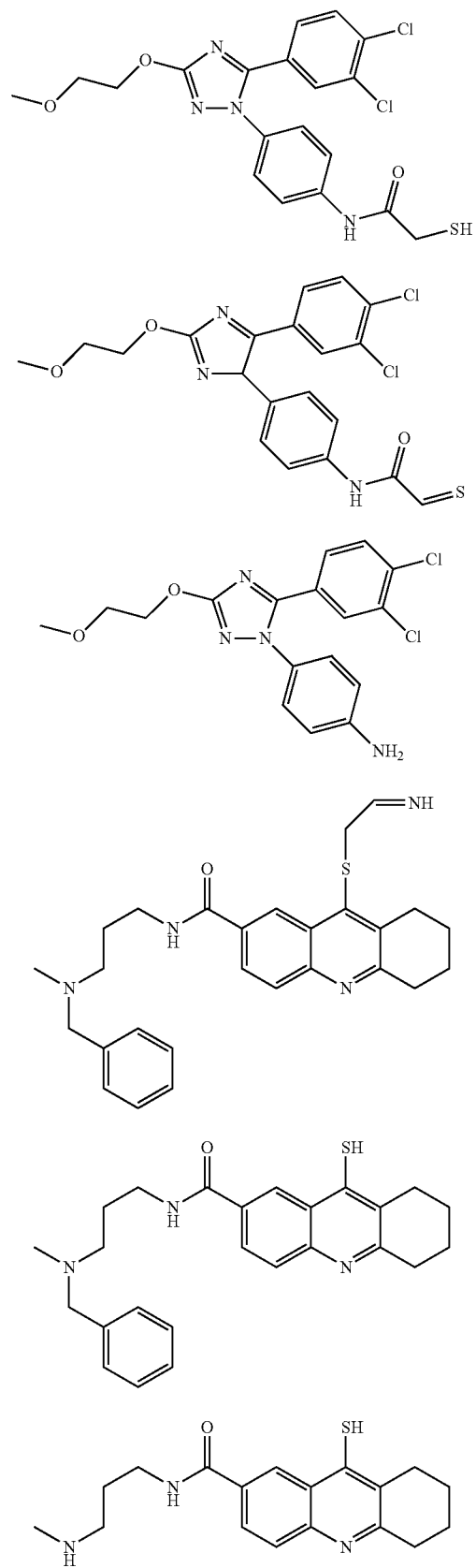
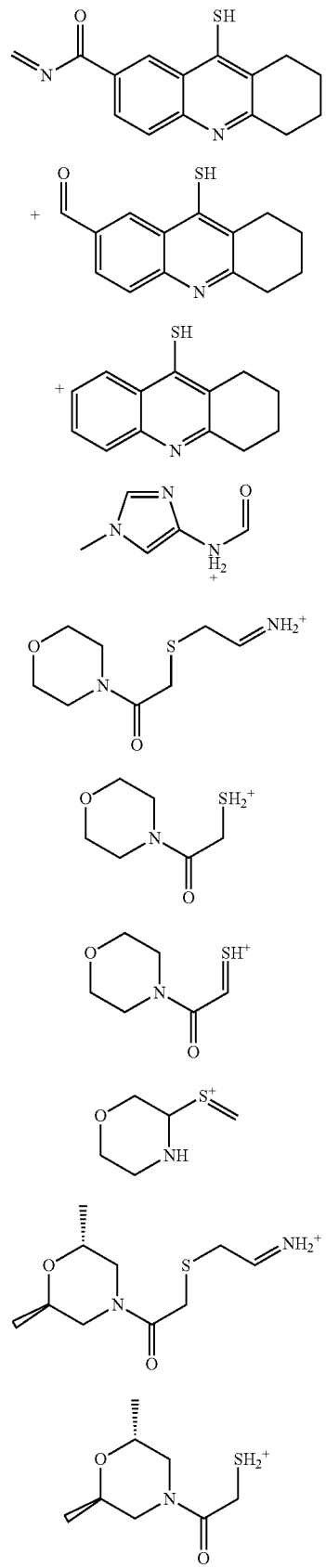

TABLE A-continued
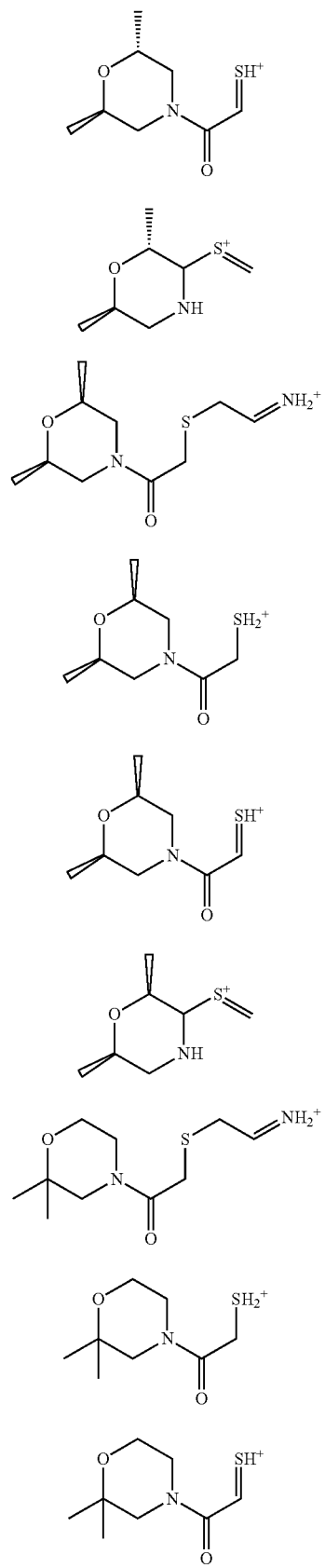
TABLE A-continued
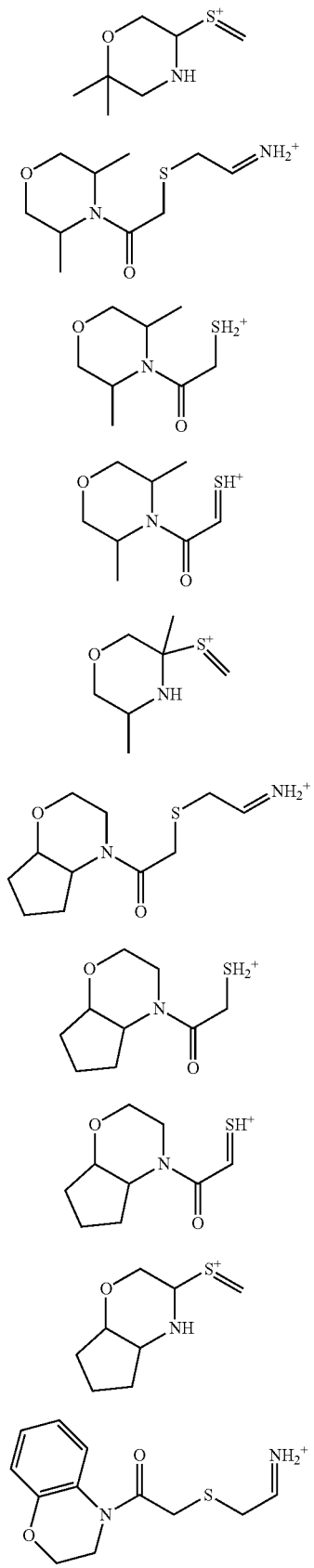

TABLE A-continued

TABLE A-continued

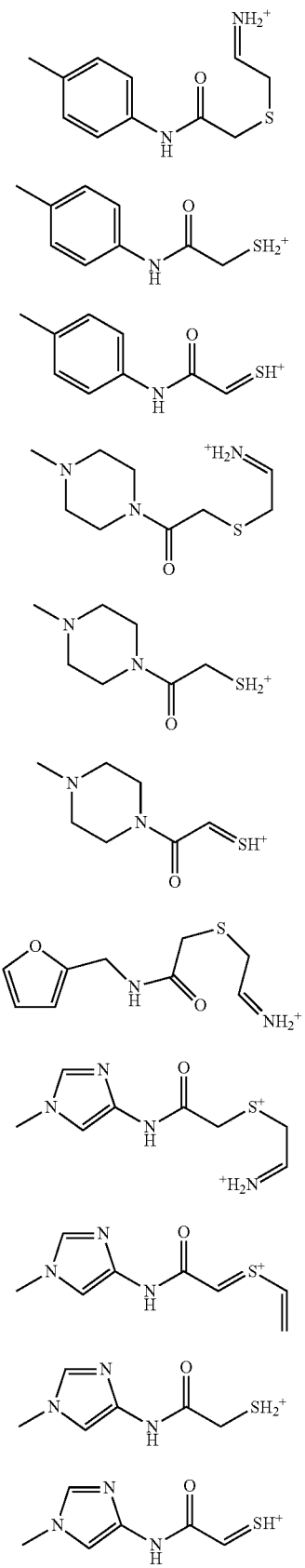

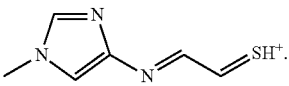

In some embodiments, a compound or ion provided in Table A is an isotopically labeled compound or ion.

As used herein, a compound or ion described herein as "isotopically labeled" (e.g., a compound labeled with one or more heavy isotopes; a compound comprising one or more heavy isotopes; and the like) is a compound or ion wherein one or more atoms are replaced or substituted by an atom having an atomic mass or mass number different from the most abundant atomic mass or mass number typically found in nature (i.e., naturally occurring). Exemplary isotopes that may be incorporated in compounds or ions of the present invention include but are not limited to $^{2}H$ (also written as D for deuterium), $^{3}H$ (also written as T for tritium), $^{13}C$, $^{15}N$, $^{18}O$, $^{35}S$, $^{36}Cl$, $^{82}Br$, $^{75}Br$, $^{76}Br$, $^{77}Br$.

In some embodiments, a compound provided in Table A comprises one or more heavy isotopes of carbon, oxygen, nitrogen, sulfur, phosphorous, chlorine, bromine, or hydrogen.

In some embodiments, one or more nitrogen atoms of a compound provided in Table A are replaced by $^{15}N$.

In some embodiments, one or more carbon atoms of a compound provided in Table A are replaced by $^{13}C$.

In some embodiments, one or more oxygen atoms of a compound provided in Table A are replaced by $^{18}O$.

As described herein, the reactions for preparing the test compounds, polypeptides, and test compound-polypeptide conjugates described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C. (such as about 25° C.).

Preparation of test compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). The test compounds, polypeptides, and test compound-polypeptide conjugates described herein can be purified by those skilled in the art by a variety of methods, including for example, high performance liquid chromatography (HPLC) and normal phase silica chromatography.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Preparation of Model Mixtures

Model peptides were synthesized using standard Fmoc chemistry known in the art and purified by reversed phase HPLC. Test compounds (i.e., peptide inhibitors) were synthesized as previously described (see e.g., Kwiatkowski et al, *Nature*, 2014, 511:616-620; Tan et al, *J. Med. Chem.* 2015, 58:6589-6606; and Zhang et al, *Chem. Biol.* 2012, 19:140-154) or obtained from commercial sources. All other compounds, unless noted otherwise, were obtained from Sigma-Aldrich.

K562 tryptic peptide aliquots were prepared as described (see e.g., Ficarro et al, *Mol. Cell Proteomics*, 2011, 10, 0111, 011064). Peptides modified with inhibitors were produced by incubating a 10-fold molar excess of inhibitor with synthetic peptides (F-G-L-C-S-G-P-A-D-T-G-R (SEQ ID NO: 7) or Y-M-A-N-G-C-L-sL-N-Y-L-R (SEQ ID NO: 8), sL=$^{15}$N-1, $^{13}$C-6 leucine) or reduced, desalted tryptic bovine serum albumin peptides in 1:1 DMSO/100 mM triethylammonium bicarbonate, pH 8.5 at 37° C. overnight. Some combinations required incubation at 60° C. overnight to produce useful levels of derivatization.

Example 2. Collision Energy Profiling

Synthetic covalently modified peptides were diluted 1:200 with 50% MeCN/water with 1% acetic acid and directly infused into a QExactive HF mass spectrometer at a flow rate of 3 µL/min using the standard ion source (spray voltage=4 kV, sheath gas=1). Spectra at a range of collision energies (e.g., 10-100 eV) were manually acquired in tune mode from m/z 100 to 1500 at a resolution of 15000. Intensities of ions were extracted and exported using multiplierz scripts. Normalized intensity values were derived and plotted using R (version 3.0.2).

Example 3. Protein Labeling and Nanoflow LC-MS/MS

Recombinant JNK, JAK3, CDK12, CDK7, EGFR, USP-7 and ITK proteins were labeled, digested, and analyzed as previously described (see e.g., Kwiatkowski et al, *Nature*, 2014, 511:616-620; Tan et al, *J. Med. Chem.* 2015, 58:6589-6606; and Zhang et al, *Chem. Biol.* 2012, 19:140-154).

Example 4. Precursor Ion Scanning

Model peptides F-G-L-C-S-G-P-A-D-T-G-R (SEQ ID NO: 7; 250 fmol) and Y-M-A-N-G-C-L-sL-N-Y-L-R (SEQ ID NO: 8; 500 fmol) conjugated to QL47 or ibrutinib were spiked into 500 ng K562 tryptic peptides and analyzed on a QTRAP 5500 mass spectrometer (AB Sciex, Framingham, Mass.). To detect QL47 modified peptides, the mass spectrometer conducted scan cycles of Q3MS followed by precursors of 482 (CE=30) or 394 (CE=40). For ibrutinib modified peptides, the mass spectrometer scanned for precursors of 474 (CE=32) or 304 (CE=50).

Example 5. Mass Spectrometry Analysis

Previously characterized acrylamide-warhead kinase probes (i.e., test compounds) were selected for analysis, and are shown below in Table 1.

TABLE 1

| Test Compounds | Primary Target Proteins | Reactive Group | Reference |
|---|---|---|---|
| JNK-IN-7 | JNK2/3 | Acrylamide* | Zhang et al, Chem. Biol. 2012, 19:140-154 |
| THZ1 | CDK7 | Acrylamide* | Kwiatkowski et al, Nature, 2014, 511:616-620 |
| THZ531 | CDK12/13 | Acrylamide* | Kwiatkowski et al. |
| TL10-201 | JAK3 | Acrylamide | Tan et al, J. Med. Chem. 2015, 58:6589-6606 |
| Ibrutinib | BTK/ITK | Acrylamide | Pan et al, ChemMedChem, 2007, 2:58-61 |
| Neratinib | HER2/EGFR | Acrylamide* | Burstein et al, J. Clin. Oncol. 2010, 28:1301-1307 |
| QL-47 | BTK | Acrylamide | Wu et al, ACS Chem. Biol. 2014, 9:1086-1091 |
| HBX-19818 | USP7 | C-Cl | Reverdy et al, Chem. Biol. 2012, 19:467-477 |
| MI-2 | MALT-1 | Chloroacetamide | Fontan et al, Cancer Cell, 2012, 22, 812-824 |

*denotes a dimethylamino group functionalized near the warhead.

Each test compound was incubated separately with the target protein, after which mass spectrometry was used to detect intact test compound-protein conjugates, and to verify the number of covalent modifications per protein. Next, each protein was digested, the resulting peptides were desalted, and nanoflow LC-MS/MS data was acquired. FIG. 1A shows a JNK-derived peptide (L-M-D-A-N-L-C-Q-V-I-Q-M-E (SEQ ID NO.: 1)) containing Cys116 modified by JNK-IN-7. It was noted that several ions detected in the MS/MS spectrum could not be assigned to canonical b- or y-type fragments which result from gas-phase cleavage of peptide amide bonds. Further investigation showed that these and other fragments were derived from the test compound, as shown in Table 2.

TABLE 2

Test Compounds and Inhibitor-Specific Fragment Ion Identified in MS/MS Spectrum of JNK-IN-7 Modified JNK2 Target Peptide

| ION | PROPOSED STRUCTURE | FORMULA | Ion m/z |
|---|---|---|---|
| Test Compound (JNK-IN-7) | | C28 H27 N7 O2 | N/A |
| TH (Thiolated ion) | | C28 H29 N7 O2 S1 | 528.2176 (H+) |
| RMA (Retro-Michael addition) | | C28 H27 N7 O2 | 494.2299 (H+) |
| RMA-DMAE-1 (Retro-Michael addition/ dimethylamine elimation type 1) | | C26 H22 N6 O2 | 451.1877 (H +) |
| RMA-DMAE-2 (Retro-Michael addition/ dimethylamine elimation type 2) | | C26 H20 N6 O2 | 449.1721 (H+) |
| TH-DMAE (Thiolated ion with dimethylamine elimination) | | C26 H22 N6 O2 S1 | 483.1598 (H+) |
| iy1 | | C22 H18 N6 O1 | 383.1615 (H+) |
| iy2 | | C15 H13 N5 | 264.1244 (H+) |
| ib2 RMA-DMAE2 1b2 with retro-Michael addition-and type 2 dimethylamine elimination | | C11 H8 N1 O2 | 186.0555 |
| ib1 | | C6 H10 N1 O1 | 112.0762 |

In particular, one fragment (FIG. 1A, "*" and Table 2, row labeled "TH (Thiolated)") corresponded to cleavage of the peptide-probe conjugate, yielding an ion containing the intact inhibitor in addition to the target cysteine thiol. These data further confirm Cys116 on JNK as the site of covalent modification. Other fragments resulted from various elimination reactions, forming "derivative ions" as described throughout the present application, for example, of the dimethylamino group or the inhibitor itself (retro-Michael addition), or cleavage of amide bonds within the inhibitor. The nomenclature provided in Table 2 describes each amide linkage in an inhibitor which is numbered based on proximity to the cysteine thiol (e.g., $iy_1$ and $ib_1$, $iy_2$ and $ib_2$, etc.).

In addition, neutral loss of the inhibitor was observed from canonical b- and y-type ions via retro-Michael addition, as shown in Table 2.

The same fragmentation pathways (i.e., formation of thiolated ions, or derivative ions thereof) were then characterized in two well-characterized acrylamide probes, ibrutinib and neratinib, clinical drugs which target BTK and HER2/EGFR, respectively, as shown in FIGS. 1B-1C and FIGS. 8A-8E. The presence of a dimethylamino moiety in inhibitors JNK-IN-7, THZ531, THZ1, and neratinib, as shown in Table 3, led to the production of specific fragment ions not observed in the other probes.

TABLE 3

Ions Produced by MS/MS of Representative Modified Test-Compound-Polypeptide Conjugates THZ1; Target = CDK7

| ION | PROPOSED STRUCTURE | FORMULA | Ion m/z |
|---|---|---|---|
| Test Compound | 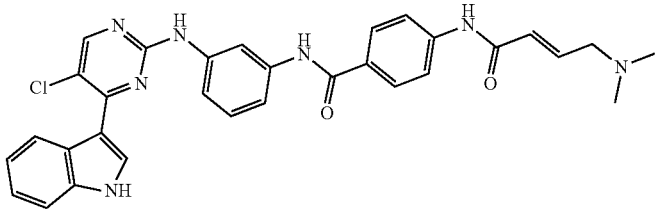 [SMILES: CN(C)C/C=C/C(=O)Nc1ccc(C(=O)Nc2cccc(Nc3ncc(Cl)c(-c4c[nH]c5ccccc45)n3)c2)cc1] | C31 H28 Cl1 N7 O2 | N/A |
| TH (Thiolated ion) | 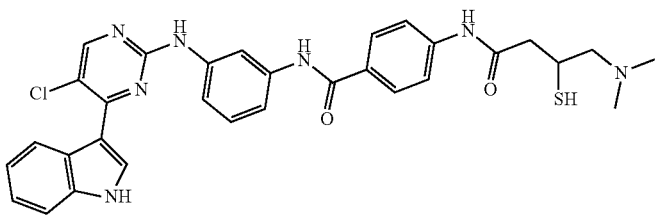 [SMILES: CN(C)CC(S)CC(=O)Nc1ccc(C(=O)Nc2cccc(Nc3ncc(Cl)c(-c4c[nH]c5ccccc45)n3)c2)cc1] | C31 H30 Cl1 N7 O2 S1 | 600.1943 (H+) |
| RMA (Retro-Michael addition) | 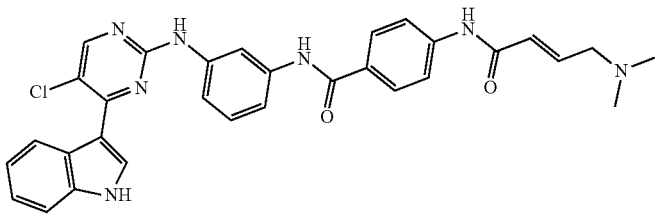 [SMILES: CN(C)C/C=C/C(=O)Nc1ccc(C(=O)Nc2cccc(Nc3ncc(Cl)c(-c4c[nH]c5ccccc45)n3)c2)cc1] | C31 H28 Cl1 N7 O2 | 566.2066 (H+) |
| TH-DMAE (Thiolated ion with dimethylamine elimination) | 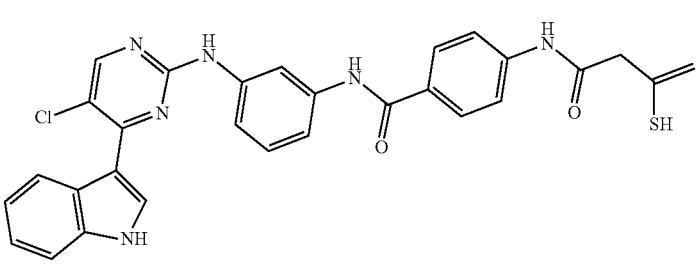 [SMILES: C=C(S)CC(=O)Nc1ccc(C(=O)Nc2cccc(Nc3ncc(Cl)c(-c4c[nH]c5ccccc45)n3)c2)cc1] | C29 H23 Cl1 N6 O2 S1 | 555.1365 (H+) |

TABLE 3-continued

Ions Produced by MS/MS of Representative Modified Test-Compound-Polypeptide Conjugates

| | | | |
|---|---|---|---|
| RMA-DMAE-1 (Retro-Michael addition/ dimethyl amine elimination type 1) | 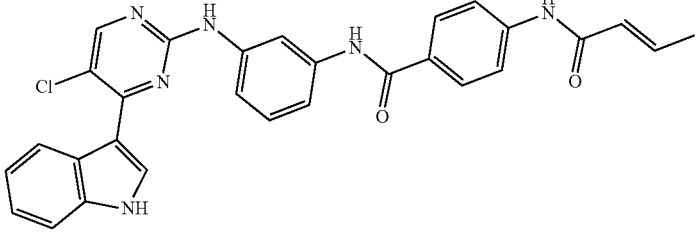 | C29 H23 Cl1 N6 O2 | 523.1644 (H+) |
| RMA-DMAE-2 (Retro-Michael addition/ dimethyl amine elimination type 2) | 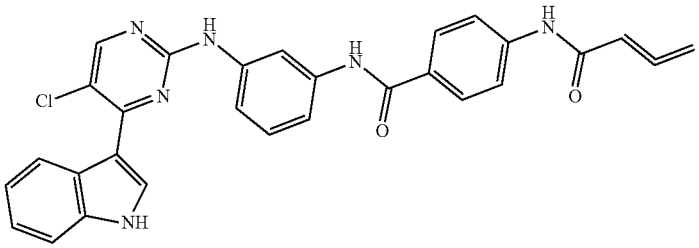 [SMILES: C=C=CC(=O)Nc1ccc(C(=O)Nc2cccc(Nc3ncc(Cl)c(-c4c[nH]c5ccccc45)n3)c2)cc1] | C29 H21 Cl1 N6 O2 | 521.1487 (H+) |
| iy1 | 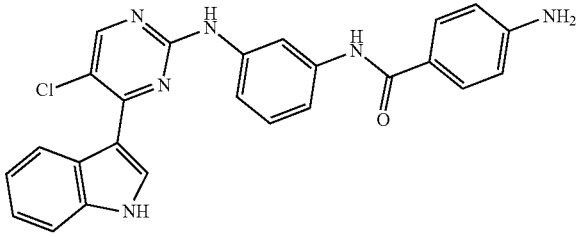 [SMILES: Nc1ccc(C(=O)Nc2cccc(Nc3ncc(Cl)c(-c4c[nH]c5ccccc45)n3)c2)cc1] | C25 H19 Cl1 N6 O1 | 455.1382 (H+) |
| iy2 | 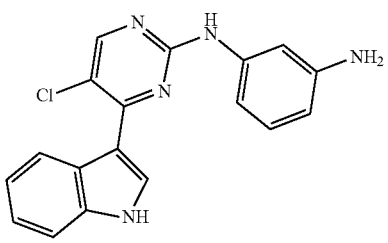 [SMILES: Nc1cccc(Nc2ncc(Cl)c(-c3c[nH]c4ccccc34)n2)c1] | C18 H14 Cl1 N5 | 336.1011 (H+) |
| ib2-RMA-DMAE-2 ib2 with retro-Michael addition and dimethylamine elimination type-2 | 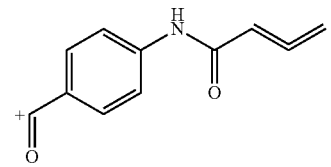 | C11 H8 N1 O2 | 186.0555 |
| ib1 | 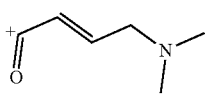 | C6 H10 N1 O1 | 112.0762 |

Figure 2A:
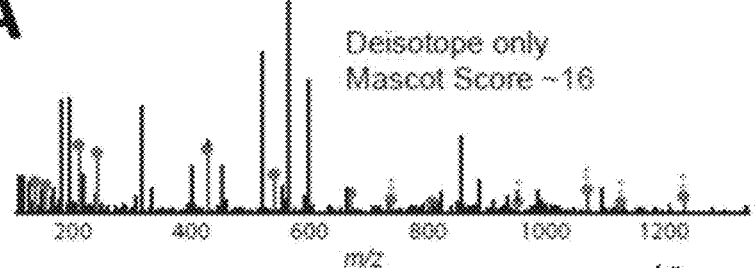
FIGS. 2A-2D show pre-processing peak lists from fragment ion spectra to account for inhibitor-related dissociation pathways, which significantly increases MASCOT peptide scores.

TABLE 3-continued
Ions Produced by MS/MS of Representative Modified Test-Compound-Polypeptide Conjugates
THZ531; Target = CDK12
*, cleavage at alkylated amine only observed at high collision energies
| ION | PROPOSED STRUCTURE (1-9 corresponds to FIG. 2A) | FORMULA | Ion m/z |
|---|---|---|---|
| Test Compound | 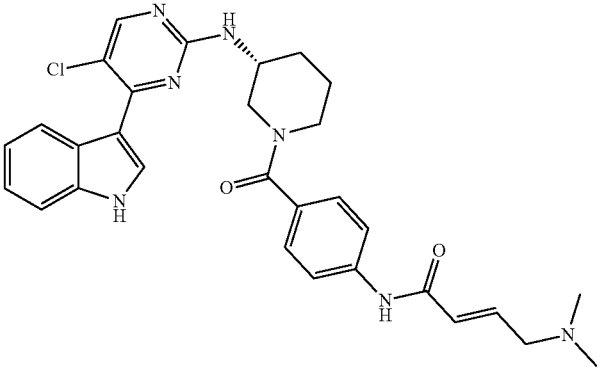 [SMILES: CN(C)C/C=C/C(=O)Nc1ccc(C(=O)N2CCC[C@@H](Nc3ncc(Cl)c(-c4c[nH]c5ccccc45)n3)C2)cc1] (8) | C30 H32 Cl1 N7 O2 H | N/A |
| TH (Thiolated ion) | 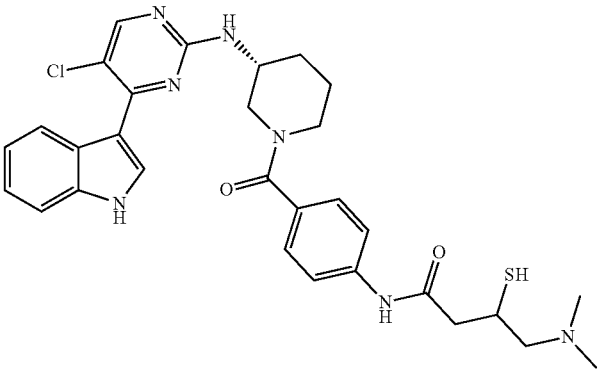 [SMILES: CN(C)CC(S)CC(=O)Nc1ccc(C(=O)N2CCC[C@@H](Nc3ncc(Cl)c(-c4c[nH]c5ccccc45)n3)C2)cc1] (9) | C30 H34 Cl1 N7 O2 S1 | 592.2256 (H+) |
| RMA (Retro-Michael addition) | 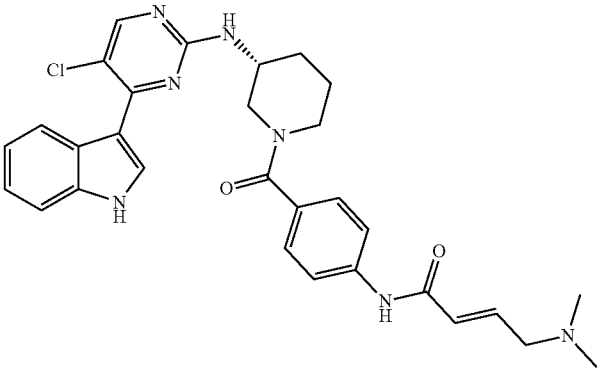 [SMILES: CN(C)C/C=C/C(=O)Nc1ccc(C(=O)N2CCC[C@@H](Nc3ncc(Cl)c(-c4c[nH]c5ccccc45)n3)C2)cc1] (8) | C30 H32 Cl1 N7 O2 H | 558.2379 (H+) |

TABLE 3-continued
Ions Produced by MS/MS of Representative Modified Test-Compound-Polypeptide Conjugates
| | | | |
|---|---|---|---|
| TH-DMAE (Thiolated ion with dimethylamine elimination) | 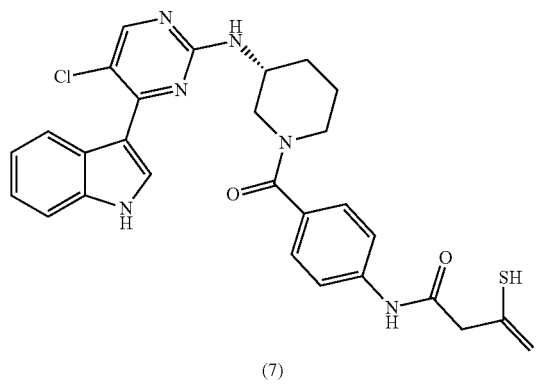 (7) | C28 H27 Cl1 N6 O2 S1 | 547.1678 (H+) |
| RMA-DMAE-1 (Retro-Michael addition/ dimethyl amine elimination type 1) | 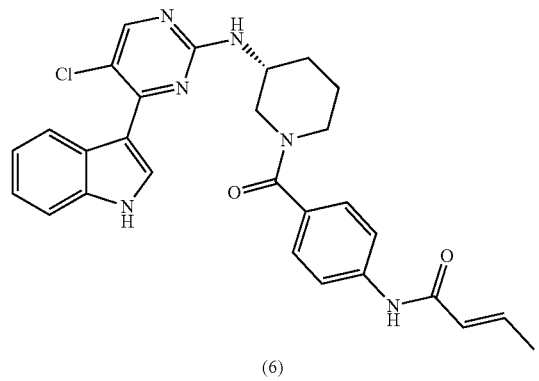 (6) | C28 H27 Cl1N6 O2 | 515.1957 (H+) |
| RMA-DMAE-2 (Retro-Michael addition/ dimethyl amine elimination type 2) | 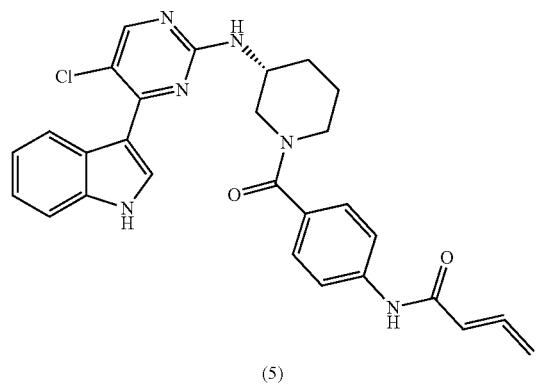 (5) | C28 H25 Cl1 N6 O2 | 513.1800 (H+) |
| iy1 | 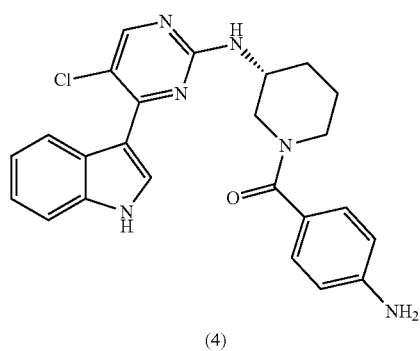 (4) | C24 H23 Cl1 N6 O1 | 447.1695 (H+) |

TABLE 3-continued
Ions Produced by MS/MS of Representative Modified Test-Compound-Polypeptide Conjugates
| | | | |
|---|---|---|---|
| iy2 | 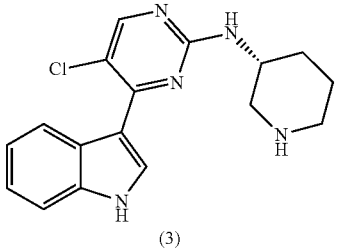 (3) | C17 H18 Cl1 N5 | 328.1323 (H+) |
| Cleavage at alkylated amine | 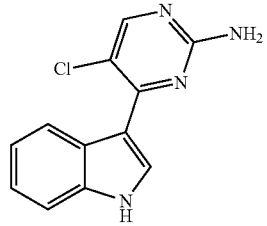 [SMILES: Nc1ncc(Cl)c(-c2c[nH]c3ccccc23)n1] *see note above | C12 H9 Cl1 N4 | 245.0589 (H+) |
| ib2-RMA-DMAE-2 ib2 with retro-Michael addition and dimethylamine elimination type-2 | 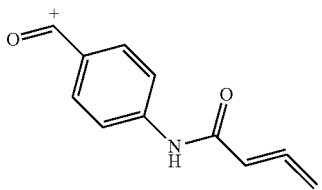 (2) | C11 H8 N1 O2 | 186.0555 |
| ib1 | 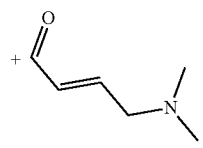 (1) | C6 H10 N1 O1 | 112.0762 |
QL-47; Target = BTK
| ION | PROPOSED STRUCTURE | FORMULA | Ion m/z |
|---|---|---|---|
| Compound modified immonium ion | 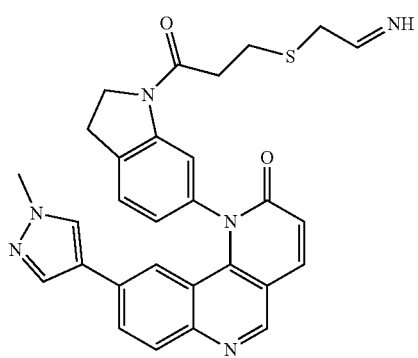 [SMILES: Cn1cc(-c2ccc3ncc4ccc(=O)n(-c5ccc6c(c5)N(C(=O)CCSCC=N)CC6)c4c3c2)cn1] | C29 H26 N6 O2 S | 523.1911 (H+) |

TABLE 3-continued
Ions Produced by MS/MS of Representative Modified Test-Compound-Polypeptide Conjugates
| | | | |
|---|---|---|---|
| Test Compound | 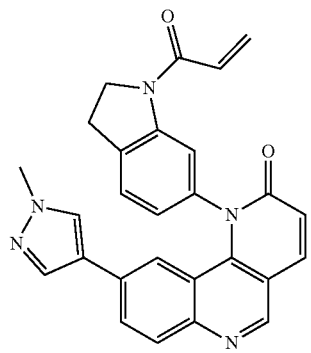 [SMILES: C=CC(=O)N1CCc2ccc(-n3c(=O)ccc4cnc5ccc(-c6cnn(C)c6)cc5c43)cc21] | C27 H21 N5 O2 | N/A |
| TH (Thiolated ion) | 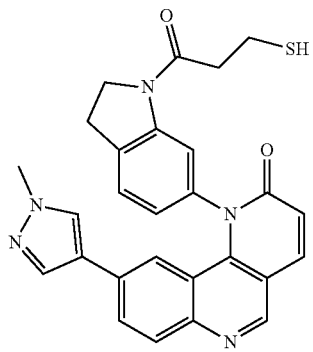 [SMILES: Cn1cc(-c2ccc3ncc4ccc(=O)n(-c5ccc6c(c5)N(C(=O)CCS)CC6)c4c3c2)cn1] | C27 H23 N5 O2 S1 | 482.1645 (H+) |
| TH-H2 (Thiolated ion with H2 elimination) | 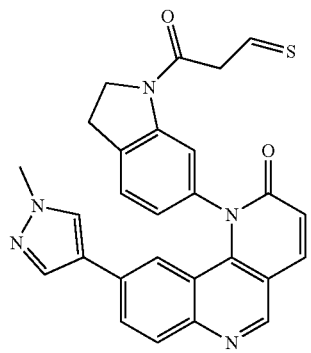 [SMILES: Cn1cc(-c2ccc3ncc4ccc(=O)n(-c5ccc6c(c5)N(C(=O)CC=S)CC6)c4c3c2)cn1] | C27 H21 N5 O2 S1 | 480.1489 (H+) |
| RMA (Retro-Michael addition) | 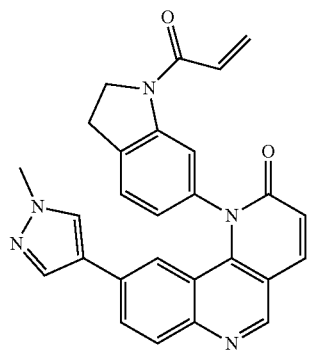 [SMILES: C=CC(=O)N1CCc2ccc(-n3c(=O)ccc4cnc5ccc(-c6cnn(C)c6)cc5c43)cc21] | C27 H21 N5 O2 | 448.1768 (H+) |

TABLE 3-continued
Ions Produced by MS/MS of Representative Modified Test-Compound-Polypeptide Conjugates
| iyl | 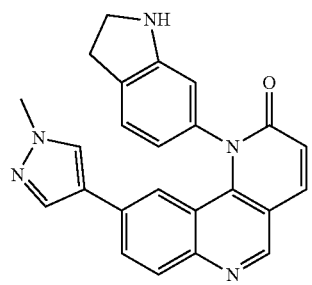 [SMILES: Cn1cc(-c2ccc3ncc4ccc(=O)n(-c5ccc6c(c5)NCC6)c4c3c2)cn1] | C24 H19 N5 O1 | 394.1662 (H+) |
Ibrutinib; Target = BTK
| ION | PROPOSED STRUCTURE | FORMULA | Ion m/z |
|---|---|---|---|
| Compound modified immonium ion | 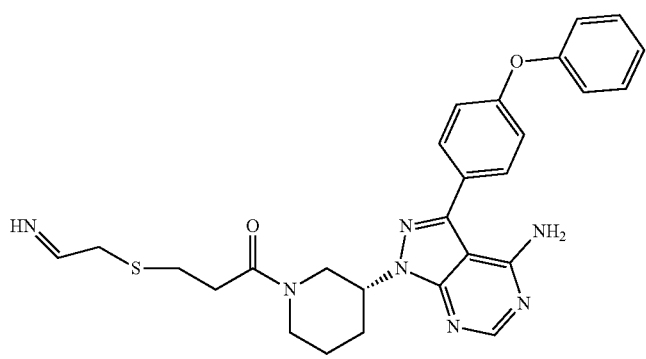 [SMILES: N=CCSCCC(=O)N1CCC[C@@H](n2nc(-c3ccc(Oc4ccccc4)cc3)c3c(N)ncnc32)C1] | C27 H29 N7 O2 S | 516.2176 (H+) |
| Test Compound | 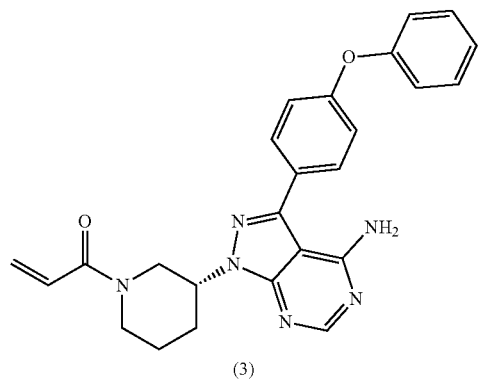 (3) | C25 H24 N6 O2 | N/A |
| TH (Thiolated ion) | 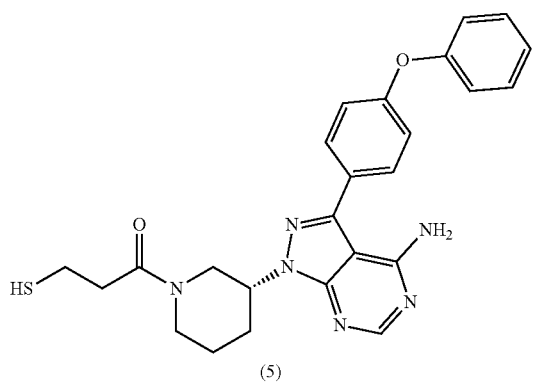 (5) | C25 H26 N6 O2 S1 | 475.1911 (H+) |

TABLE 3-continued
Ions Produced by MS/MS of Representative Modified Test-Compound-Polypeptide Conjugates
| | | | |
|---|---|---|---|
| Thiolated ion with H2 elimination | 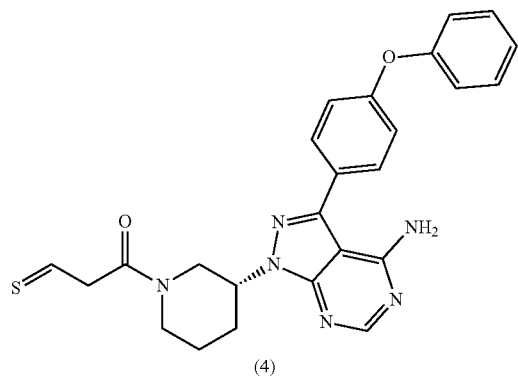 (4) | C25 H24 N6 O2 S1 | 473.1754 (H+) |
| RMA (Retro-Michael addition) | 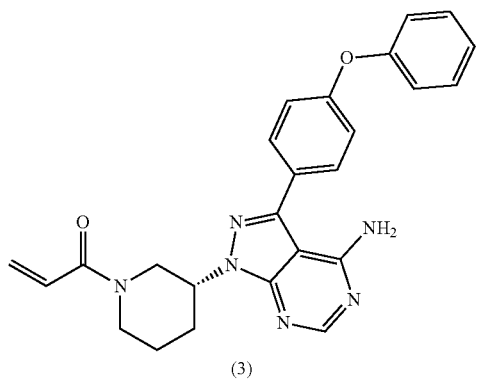 (3) | C25 H24 N6 O2 | 441.2034 (H+) |
| iyl | 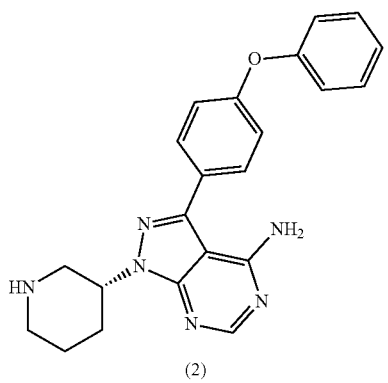 (2) | C22 H22 N6 O1 | 387.1928 (H+) |
| Cleavage at alkylated amine | 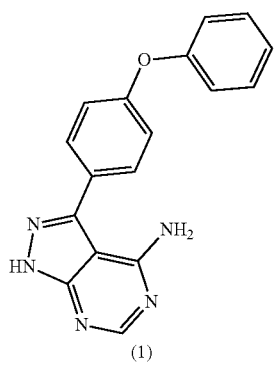 (1) | C17 H13 N5 O1 | 304.1193 (H+) |

TABLE 3-continued

Ions Produced by MS/MS of Representative Modified Test-Compound-Polypeptide Conjugates

| RMA with alkylated amine cleavage | [structure of acryloyl-tetrahydropyridine] | C8 H12 N1 O1 | 138.0913 (H+) |

Neratinib; Target = EGFR/Her2

| ION | PROPOSED STRUCTURE | FORMULA | Ion m/z |
|---|---|---|---|
| Test Compound | [structure of neratinib] | C30 H29 Cl1 N6 O3 | N/A |
| TH (Thiolated ion) | [structure of thiolated neratinib] | C30 H31 Cl1 N6 O3 S1 | 591.19396 (H+) |
| RMA (Retro-Michael addition) | [structure of neratinib after retro-Michael addition] | C30 H29 Cl1 N6 O3 | 557.20624 (H+) |

TABLE 3-continued
Ions Produced by MS/MS of Representative Modified Test-Compound-Polypeptide Conjugates
TH-DMAE
(Thiolated ion with dimethylamine elimination)
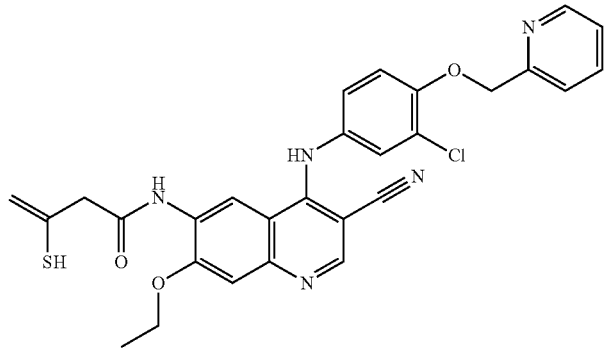 [SMILES: C=C(S)CC(=O)Nc1cc2c(Nc3ccc(OCc4ccccn4)c(Cl)c3)c(C#N)cnc2cc1OCC]
C28 H24 Cl1 N5 O3 S1     546.13611 (H+)
RMA-DMAE-1
(Retro-Michael addition/ dimethyl amine elimination type 1)
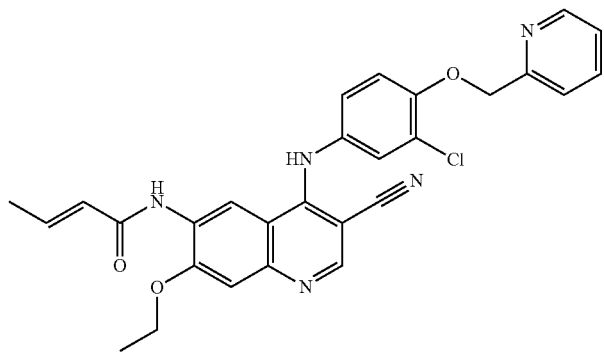 [SMILES: C/C=C/C(=O)Nc1cc2c(Nc3ccc(OCc4ccccn4)c(Cl)c3)c(C#N)cnc2cc1OCC]
C28 H24 Cl1N5 O3     514.16404 (H+)
RMA-DMAE-2
(Retro-Michael addition/ dimethyl amine elimination type 2)
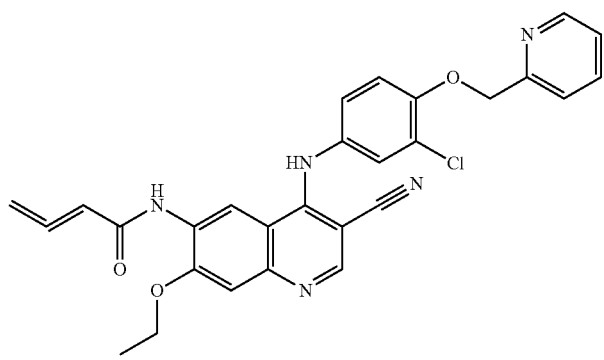 [SMILES: C=C=CC(=O)Nc1cc2c(Nc3ccc(OCc4ccccn4)c(Cl)c3)c(C#N)cnc2cc1OCC]
C28 H22 Cl1N5 O3     512.14839 (H+)
iy1
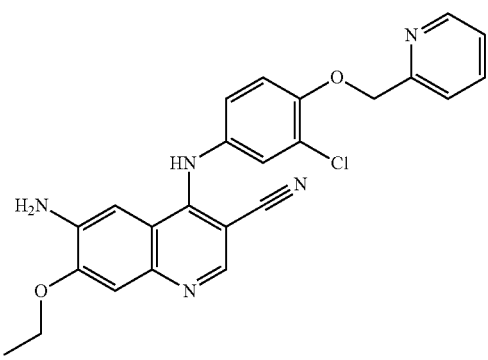 [SMILES: CCOc1cc2ncc(C#N)c(Nc3ccc(OCc4ccccn4)c(Cl)c3)c2cc1N]
C24 H20 Cl1 N5 O2     446.13783 (H+)

TABLE 3-continued

Ions Produced by MS/MS of Representative Modified Test-Compound-Polypeptide Conjugates

| ib1 | 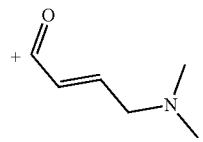 | C6 H10 N1 O1 | 112.07624 |

TL10-201; Target = JAK3

| ION | PROPOSED STRUCTURE | FORMULA | Ion m/z |
|---|---|---|---|
| Compound modified immonium ion | 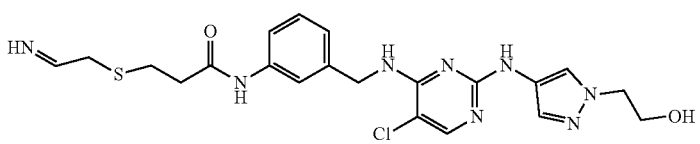 [SMILES: N=CCSCCC(=O)Nc1cccc(CNc2nc(Nc3cnn(CCO)c3)ncc2Cl)c1] | C21 H25 Cl N8 O2 S | 489.1582 (H+) |
| Test Compound | 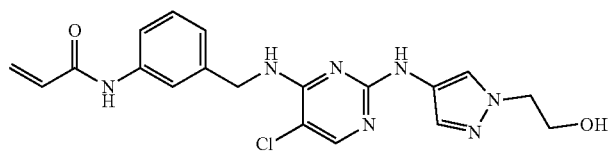 [SMILES: C=CC(=O)Nc1cccc(CNc2nc(Nc3cnn(CCO)c3)ncc2Cl)c1] | C19 H20 Cl1 N7 O2 | N/A |
| TH (Thiolated ion) | 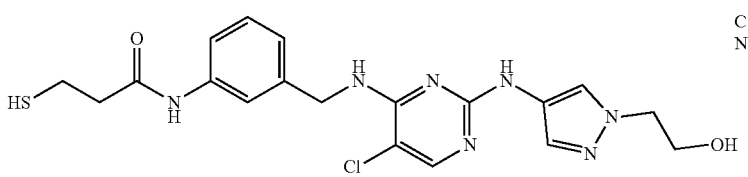 | C19 H22 Cl1 N7 O2 S1 | 448.13170 (H+) |
| Thiolated ion with H2 elimination | 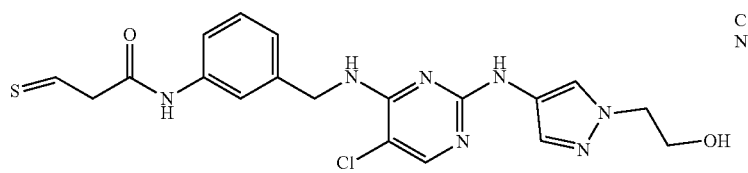 | C19 H20 Cl1 N7 O2 S1 | 446.1160 (H+) |
| RMA (Retro-Michael addition) | 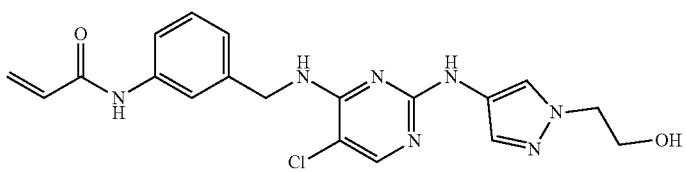 [SMILES: C=CC(=O)Nc1cccc(CNc2nc(Nc3cnn(CCO)c3)ncc2Cl)c1] | C19 H20 Cl1 N7 O2 | 414.14398 (H+) |
| iy1 | 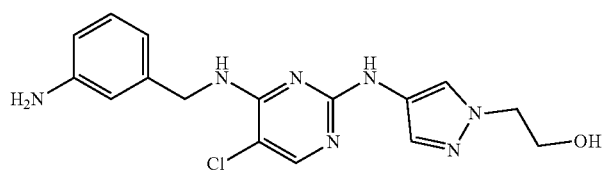 [SMILES: Nc1cccc(CNc2nc(Nc3cnn(CCO)c3)ncc2Cl)c1] | C16 H18 Cl1 N7 O1 | 360.13341 (H+) |
| Cleavage at alkylated amine | 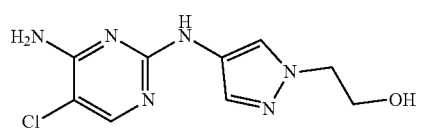 [SMILES: Nc1nc(Nc2cnn(CCO)c2)ncc1Cl] | C9 H11 Cl1 N6 O1 | 255.07556 (H+) |

TABLE 3-continued

Ions Produced by MS/MS of Representative Modified Test-Compound-Polypeptide Conjugates MI-2; Target = MALT1

| ION | PROPOSED STRUCTURE | FORMULA | Ion m/z |
|---|---|---|---|
| Test Compound | | C19 H17 Cl3 N4 O3 | N/A |
| TH (Thiolated ion) | | C19 H18 Cl2 N4 O3 S1 | 453.05494 (H+) |
| Thiolated ion with H2 elimination | | C19 H16 Cl2 N4 O3 S1 | 451.03929 (H+) |
| iyl | | C17 H16 Cl2 N4 O2 | 379.07231 (H+) |

TABLE 3-continued

Ions Produced by MS/MS of Representative Modified Test-Compound-Polypeptide Conjugates HBX-19818; Target = USP7

| ION | PROPOSED STRUCTURE | FORMULA | Ion m/z |
| --- | --- | --- | --- |
| Compound modified immonium ion | | C27 H32 N4 O S | 461.2370 (H+) |
| Test Compound | | C25 H28 Cl1 N3 O1 | N/A |
| TH (Thiolated ion) | | C25 H29 N3 O1 S1 | 420.21041 (H+) |
| Cleavage at alkylated amine | | C18 H23 N3 O1 S1 | 330.1635 (H+) |
| Elimination product | | C15 H14 N2 O1 S1 | 271.0900 (H+) |
| ib1 | | C14 H12 N1 O1 S1 | 242.06396 |

TABLE 3-continued

Ions Produced by MS/MS of Representative Modified Test-Compound-Polypeptide Conjugates

| | | | |
|---|---|---|---|
| ia1 (loss of CO from ib1) | SH (structure) | C13 H12 N1 S1 | 214.06904 |

To explore the fragmentation pathways in the context of alternative warheads and target families, HBX-19818 (a deubiquitinase (DUB) inhibitor, (see e.g., Reverdy et al, *Chem. Biol.* 2012, 19, 467-477) as well as the paracaspase inhibitor MI-2 (see e.g., Fontan et al, *Cancer Cell*, 2012, 22:812-824) were investigated (see e.g., Table 1 and Table 3), both of which modify cysteine residues. Thiolated ions were observed in the MS/MS spectra of peptides labeled with each probe, confirming this as a dissociation pathway shared across covalent inhibitors which modify their targets through a thioether bond (see e.g., FIGS. 8D, 8F, and 8H). Consistent with the data above, amide bond cleavage was observed within each inhibitor (see e.g., FIG. 8G, labeled "1" and FIG. 8H, labeled "1"). It was further observed that peptides covalently modified with HBX-19818 or MI-2 did not undergo retro-Michael addition, but rather a low-yield elimination reaction to produce a series of dehydroalanine-containing b- and y-type fragment ions (see e.g., FIG. 8F). It was determined that the dissociation pathways described above are agnostic with respect to peptide sequence, charge state, and proteolytic enzyme.

Collectively, these results suggest that probes which form covalent adducts through a thioether linkage dissociate under MS/MS conditions to yield predictable, structurally specific fragment ions.

Example 6. Spectral Match Scores

Figure 9A:
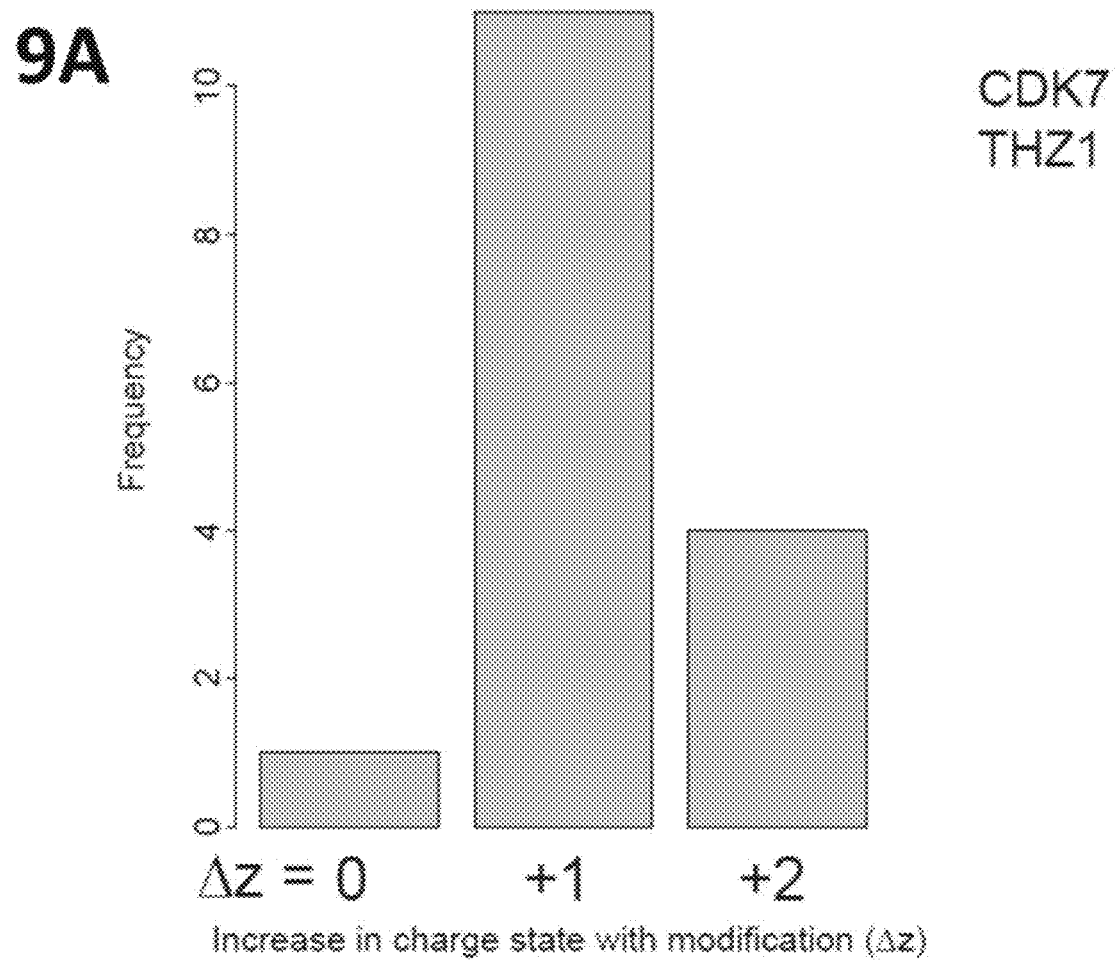
FIGS. 9A-9B show bar graphs illustrating shift in charge state distribution observed after conjugation of reduced BSA peptides to (FIG. 9A) THZ1 (CDK7 inhibitor) or (FIG. 9B) THZ531 (CDK12 inhibitor) compared to the same peptides alkylated with iodoacetamide.
Figure 9B:
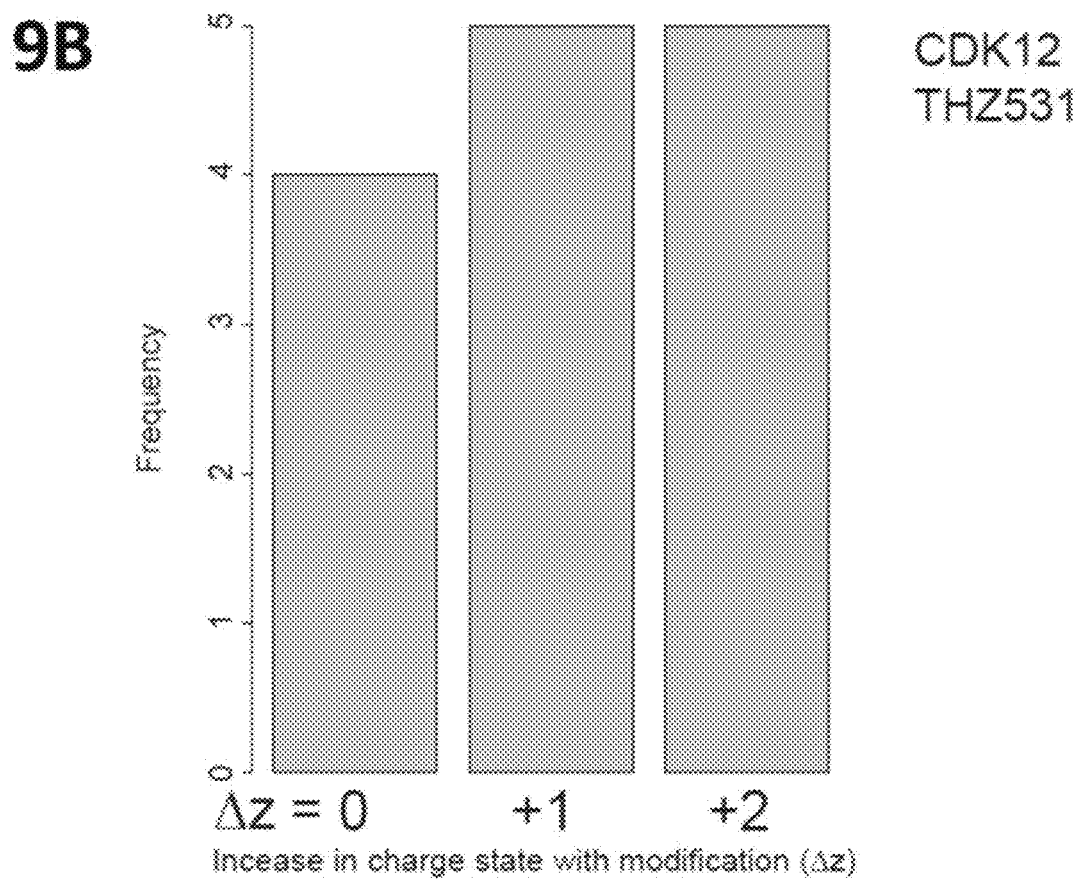

Though covalently modified peptides were identified as described in Example 5, in many instances the associated fragment ions provided relatively low spectral match scores when using the commercial MASCOT algorithm (see e.g., Perkins et al, *Electrophoresis*, 1999, 20:3551-3567) for database search and sequence assignment. For example, the high-resolution MS/MS spectrum shown in FIG. 2A (THZ531) yielded a confidence peptide score of 15.68. A majority of kinase inhibitors contain one or more heterocyclic rings that impart significant gas-phase basicity, leading to increased peptide charge state (typically ≥3+, shown in FIGS. 9A and 9B). Dissociation of higher charge state peptides can yield complicated product ion spectra containing multiply-charged fragment ions which can diminish the performance of search algorithms. To account for these effects the spectral pre-processing scripts were modified to normalize all fragment ions to the 1+ charge state. This modification increased the MASCOT score for the MS/MS spectrum to 40.

Figure 2B:
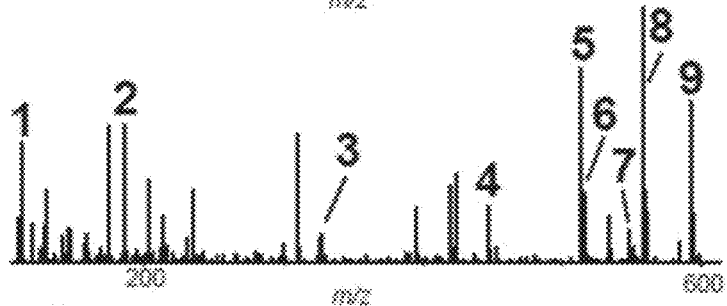
Figure 2C:
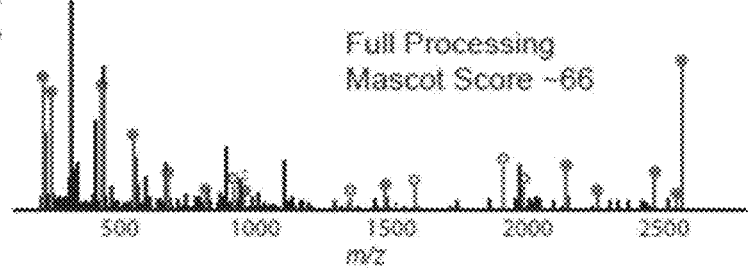
Figure 2D:
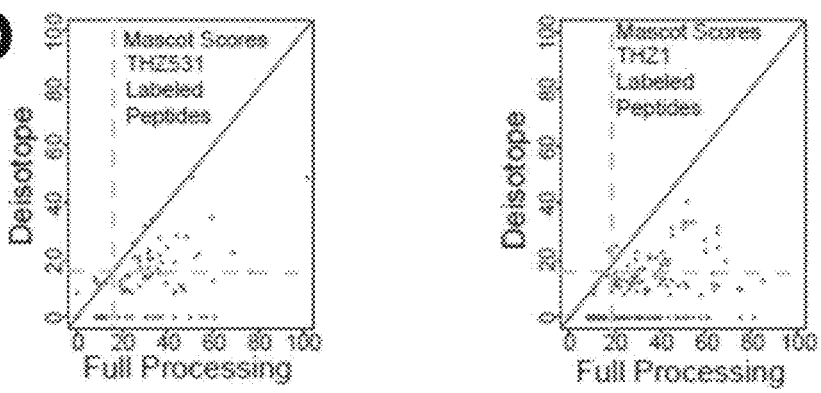
Figures 3A, 3B, 3C:
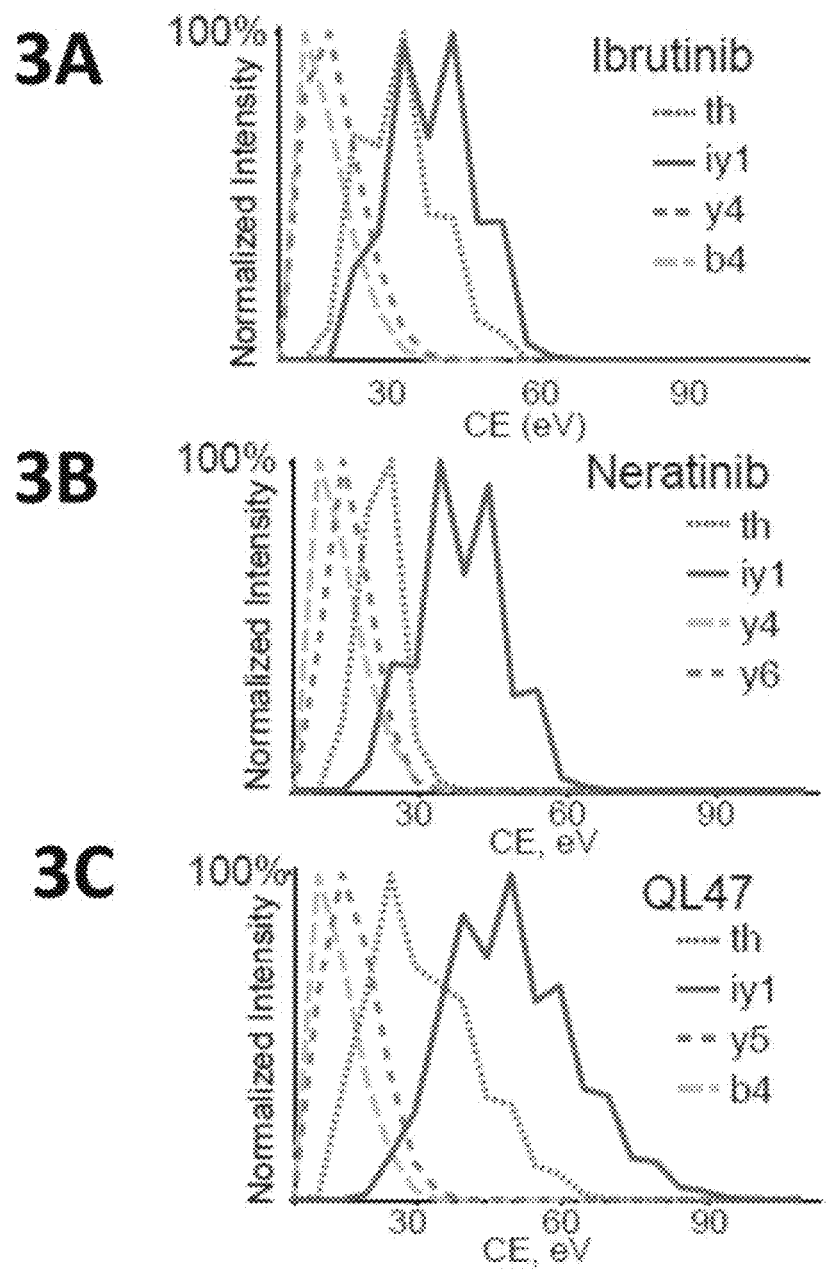
FIGS. 3A-3C show normalized fragment ion intensity vs. collision energy (CE) for inhibitor specific (thiolated and iy1) ions produced by MS/MS of a triply charged synthetic cysteine-containing peptide (FGLCSGPADTGR (SEQ ID NO: 7)) labeled with (FIG. 3A) Ibrutinib.

Without being bound by theory, it was surmised that the myriad of MS/MS ions derived from fragmentation of the inhibitor (see e.g. FIG. 2B and Tables 2-3) further diminished the quality of spectral matches. To test this hypothesis MS/MS spectra were pre-processed (e.g., prior to submission for MASCOT database search) based on the fragmentation pathways described above in Example 5. First, neutral loss of the inhibitor from the peptide backbone was defined as part of the variable/fixed modification in MASCOT; this step increased the peptide score to 50. Second, the remaining inhibitor-related ions described in Tables 2-3 were removed (FIG. 2B), which further improved the MASCOT score to 66, as shown in FIG. 2C. To assess these improvements across a larger population of modified peptides, THZ531 and THZ-1 with reduced bovine serum albumin (BSA) and the MASCOT peptide scores were compared for spectra which were subject to minimal (deisotope only) or extensive pre-processing. It was observed that use of the full pre-processing scheme as described above led to consistent and significant improvements in MASCOT scores for >90% of MS/MS spectra, as shown in FIG. 2D. These results demonstrate that the consistent, inhibitor-associated fragmentation pathways can be used to improve the ability to identify covalently modified peptides.

Example 7. Targeted Mass Spectrometry

Figures 10A, 10B, 10C, 10D:
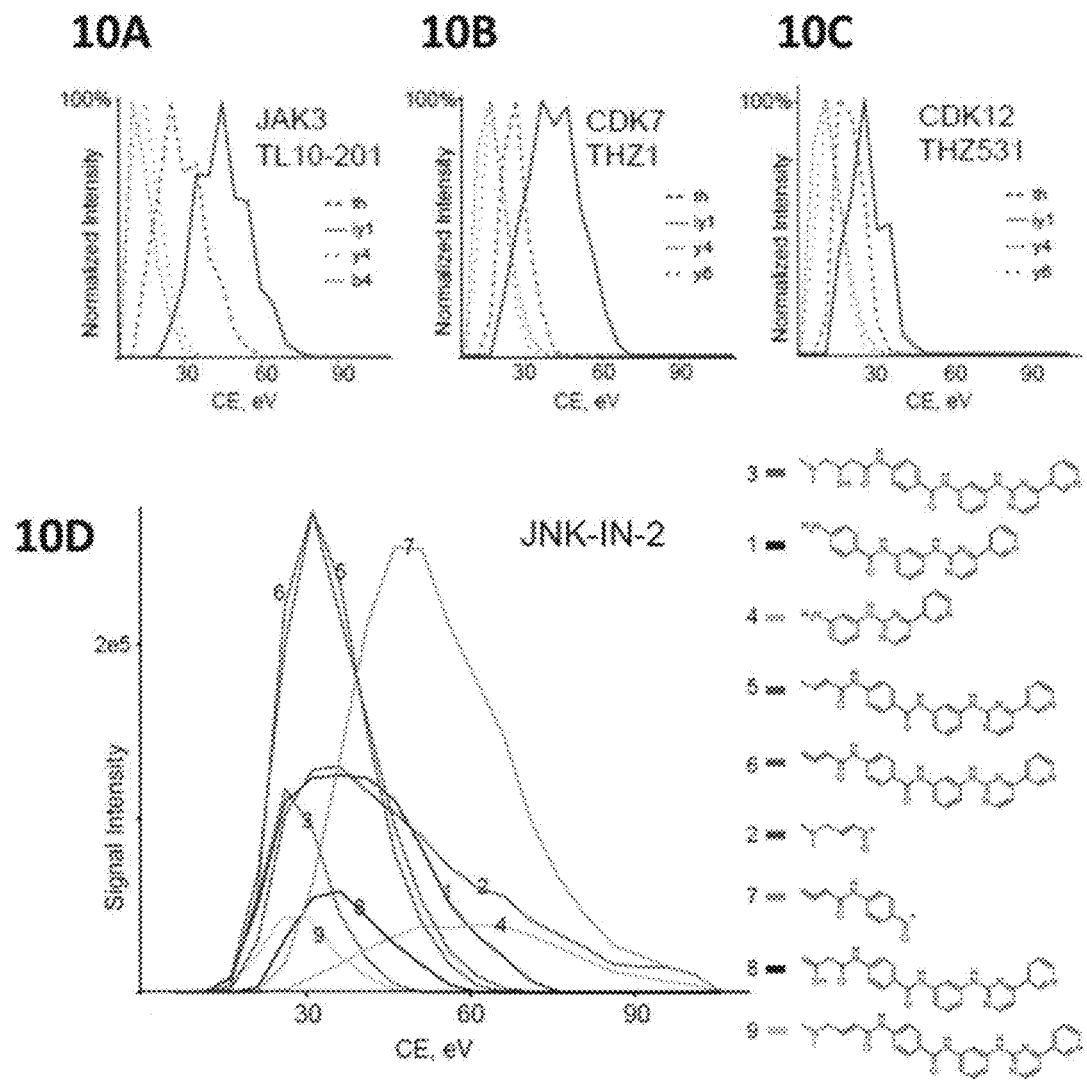
FIGS. 10A-10F show normalized fragment ion intensity vs. collision energy (CE) for inhibitor specific (thiolated and iy1) ions produced by MS/MS of triply charged synthetic cysteine-containing peptide FGLCSGPADTGR (SEQ ID NO: 7) labeled with (FIG. 10A) TL10-201.
Figure 10E:
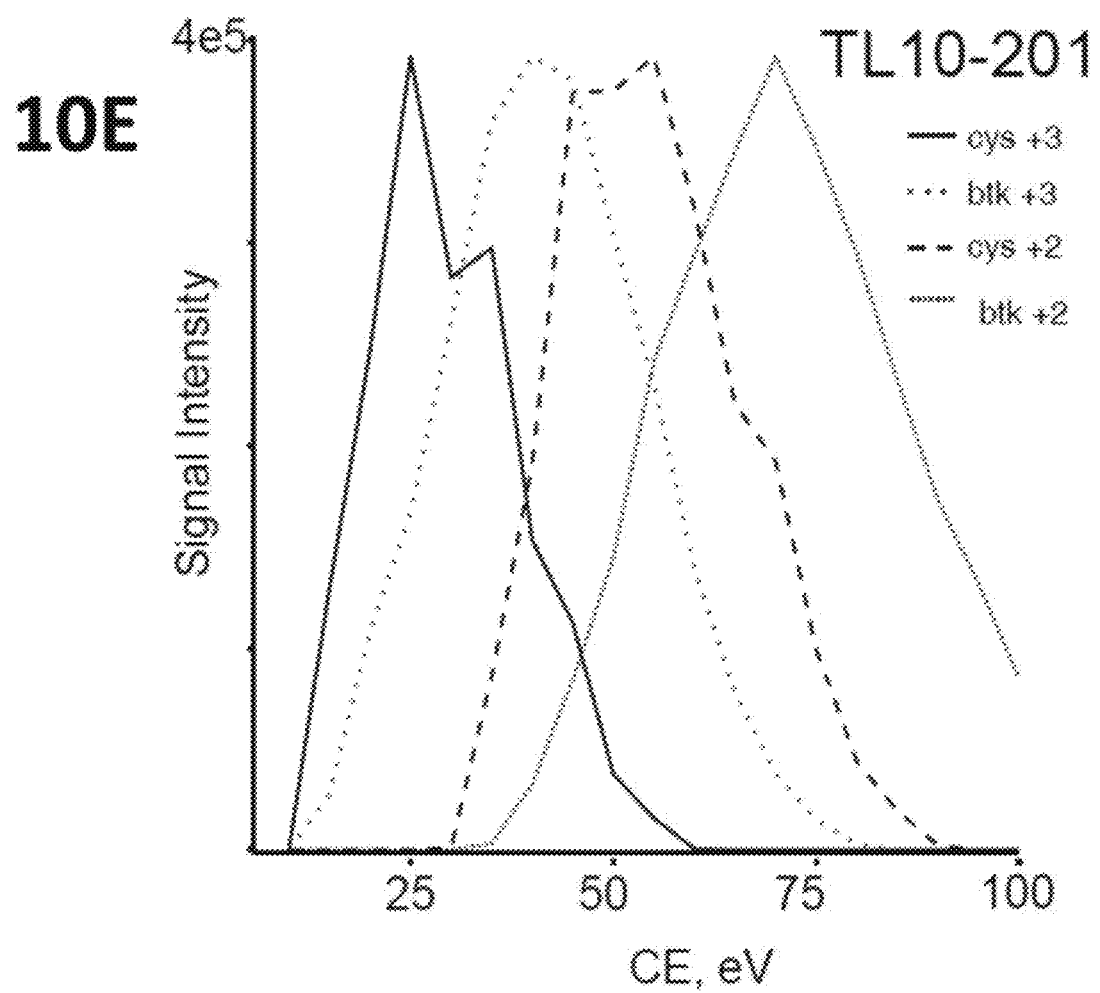
Figure 10F:
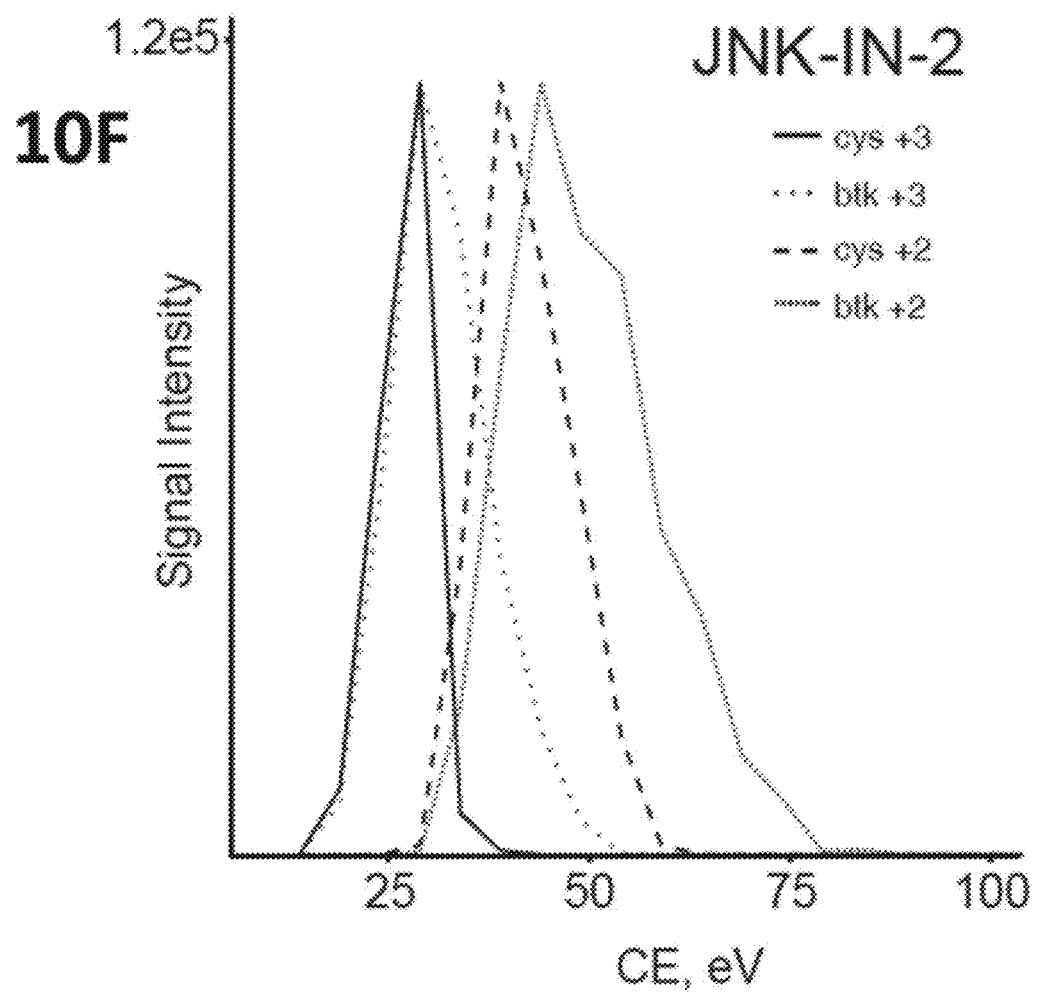

Based on the results described in Example 5-6, it was speculated that inhibitor-associated fragmentation pathways can be used as the basis for highly-selective precursor scanning or other targeted mass spectrometry assays. As a prerequisite to these experiments, the yield of inhibitor-specific fragment ions as a function of kinetic energy during MS/MS was investigated. Accordingly, conjugated model cysteine-containing peptides with 8 different acrylamide inhibitors were prepared. Next, direct infusion of the mixture was used to acquire MS/MS spectra for each modified peptide across a range of collision energies (CE). Plots of ion yield as a function of CE revealed several trends. For example, it was observed that use of higher CE resulted in gas phase enrichment of structure-specific fragment ions from each inhibitor relative to canonical peptide b- and y-type ions. In fact, the $iy_n$ ions reached a maximum yield at >40 eV, a CE where peptide fragment ion intensities were greatly reduced, as shown in FIGS. 3A-3C and FIGS. 10A-10D. In addition, for specific ion types (e.g., thiolated ion) there existed sufficient overlap in CE profiles such that a single collision energy generated significant signal intensity (>50% max) for at least one charge state of a given peptide, as shown in FIGS. 10E and 10F. Finally, inhibitors incorporating a dimethylamino group produced a characteristic fragment at m/z=112, a relatively 'quiet' region of peptide MS/MS spectra, as shown in FIG. 10D.

Figures 4A, 4B, 4C, 4D, 4E, 4F, 4G:
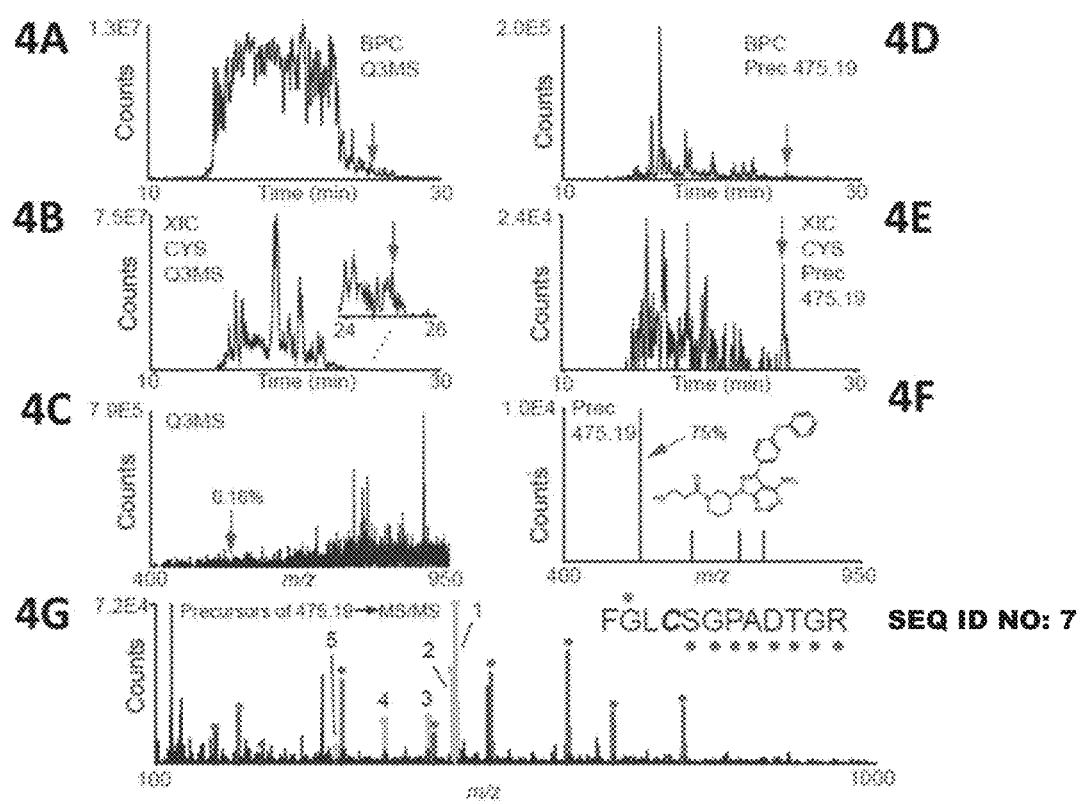
FIGS. 4A-4G show novel dissociation pathways associated with thioether linked covalent probes, which provide for significant gas-phase enrichment during precursor ion scanning mass spectrometry.
Figures 11A, 11B, 11C, 11D, 11E, 11F:
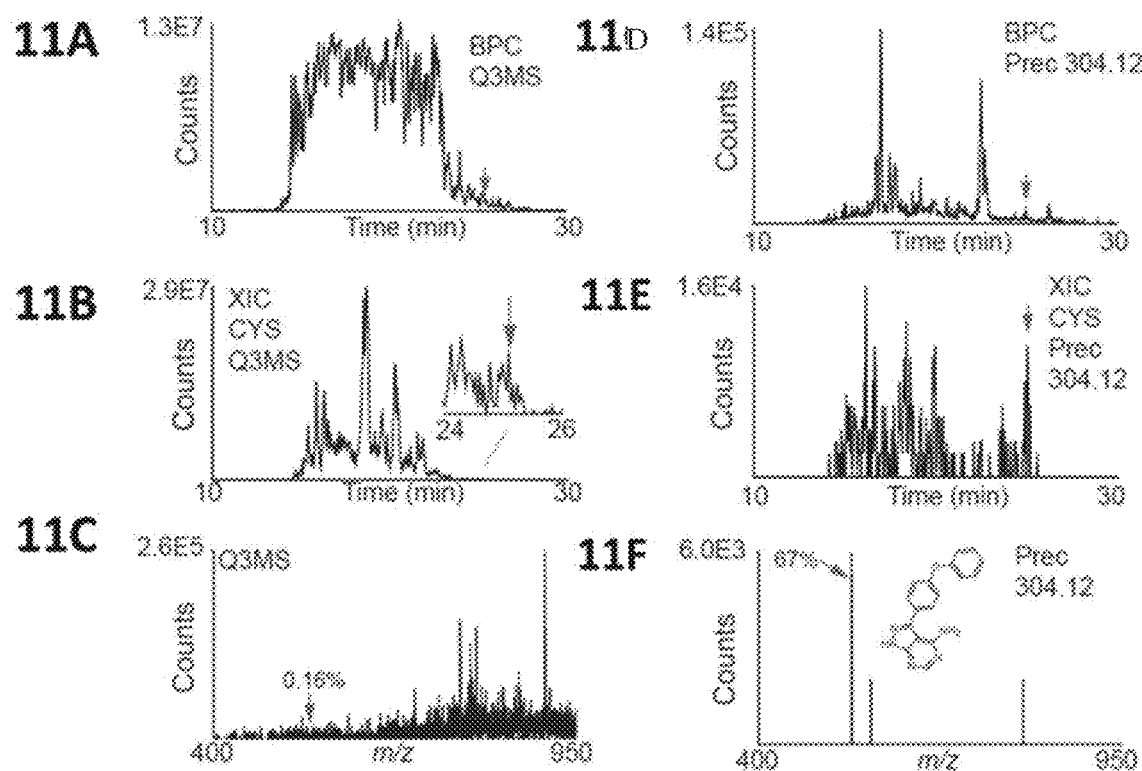
FIGS. 11A-11F show that a second dissociation pathway can be used to afford selective detection of an Ibrutinib labeled peptide by precursor ion mass spectrometry.
Figures 12A, 12B, 12C:
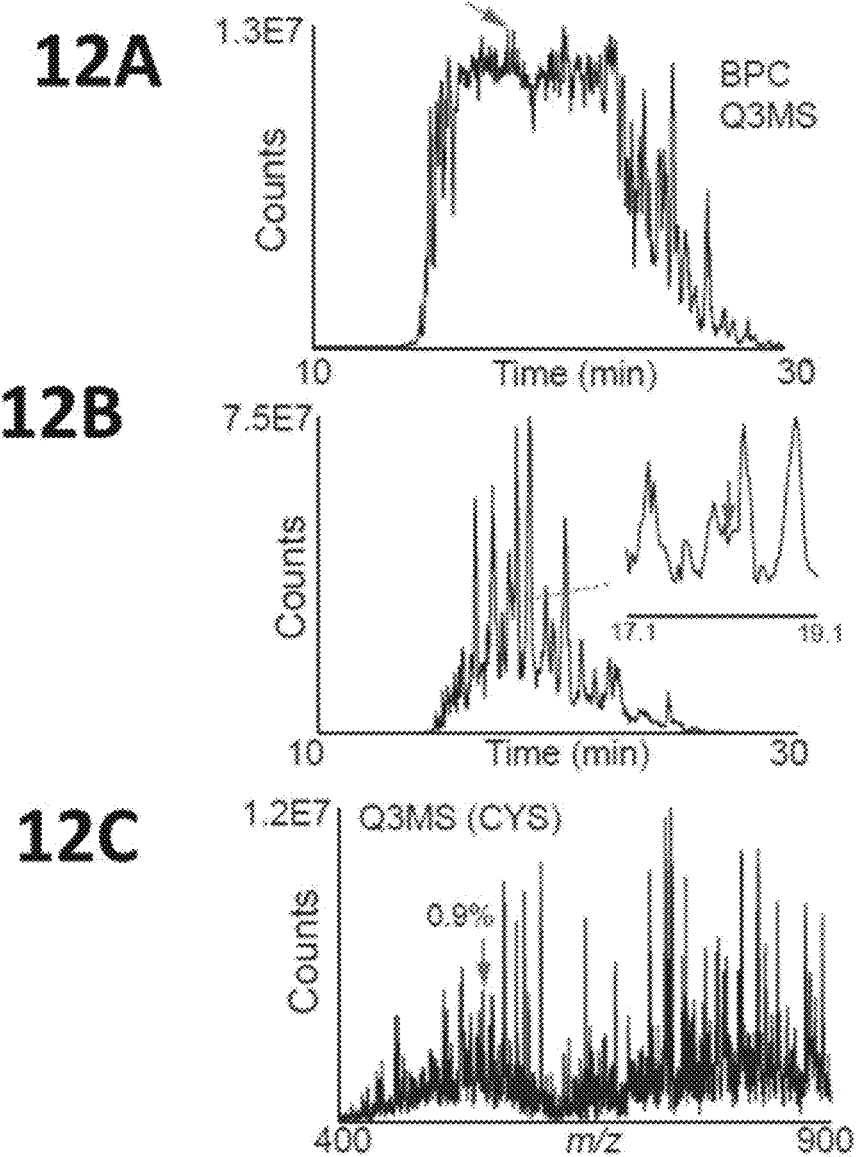
FIGS. 12A-12J show selective detection of QL47-modified peptides using precursor ion scanning mass spectrometry.
Figures 12D, 12E, 12F:
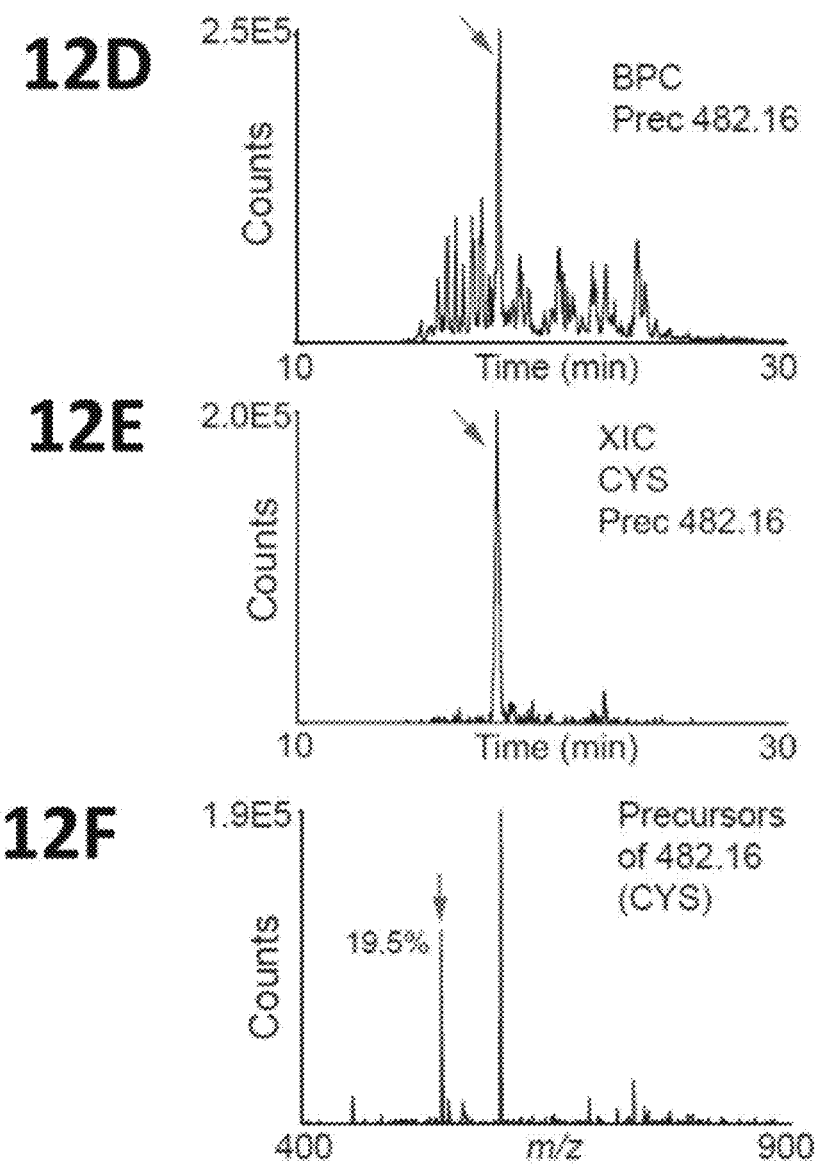
Figures 12G, 12H, 12I:
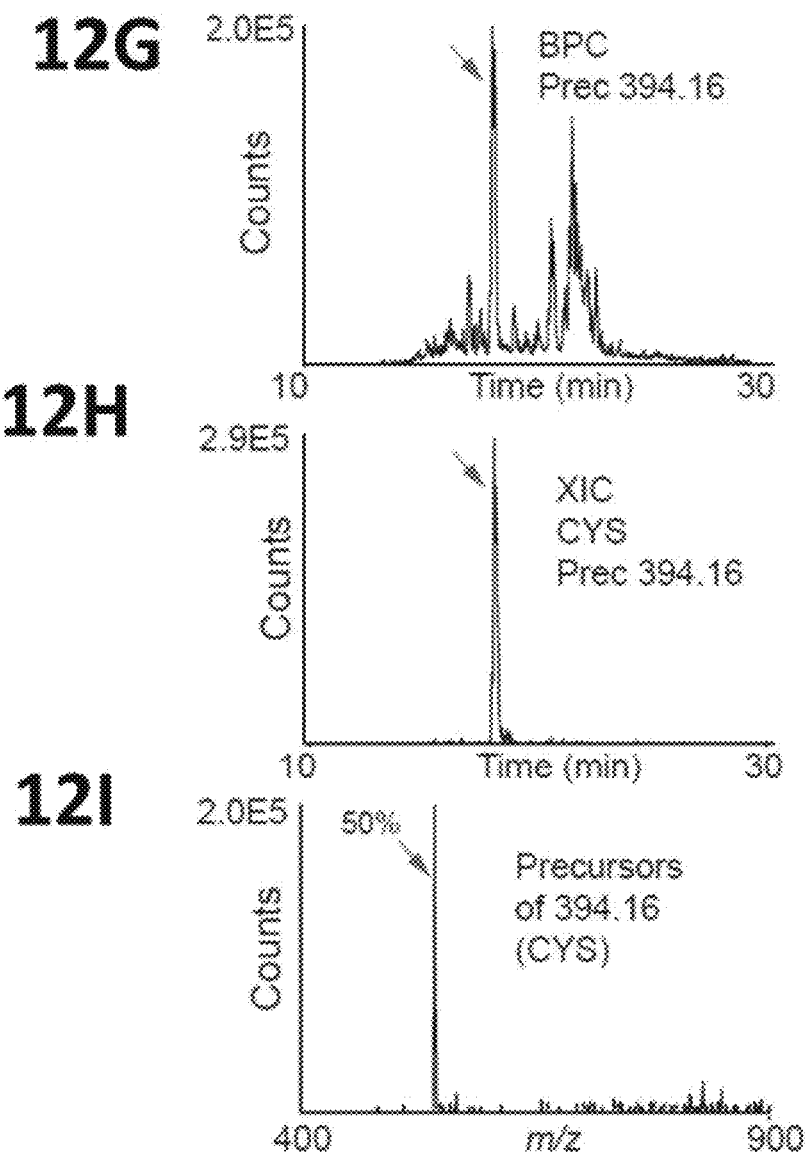
Figure 12J:
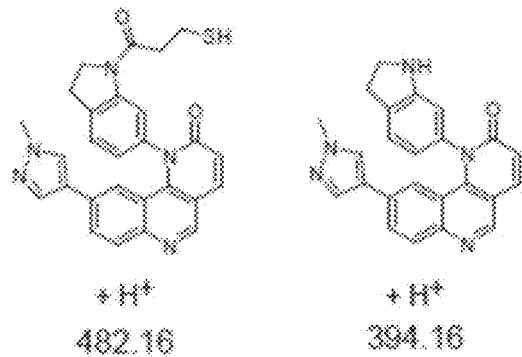
Figure 13A:
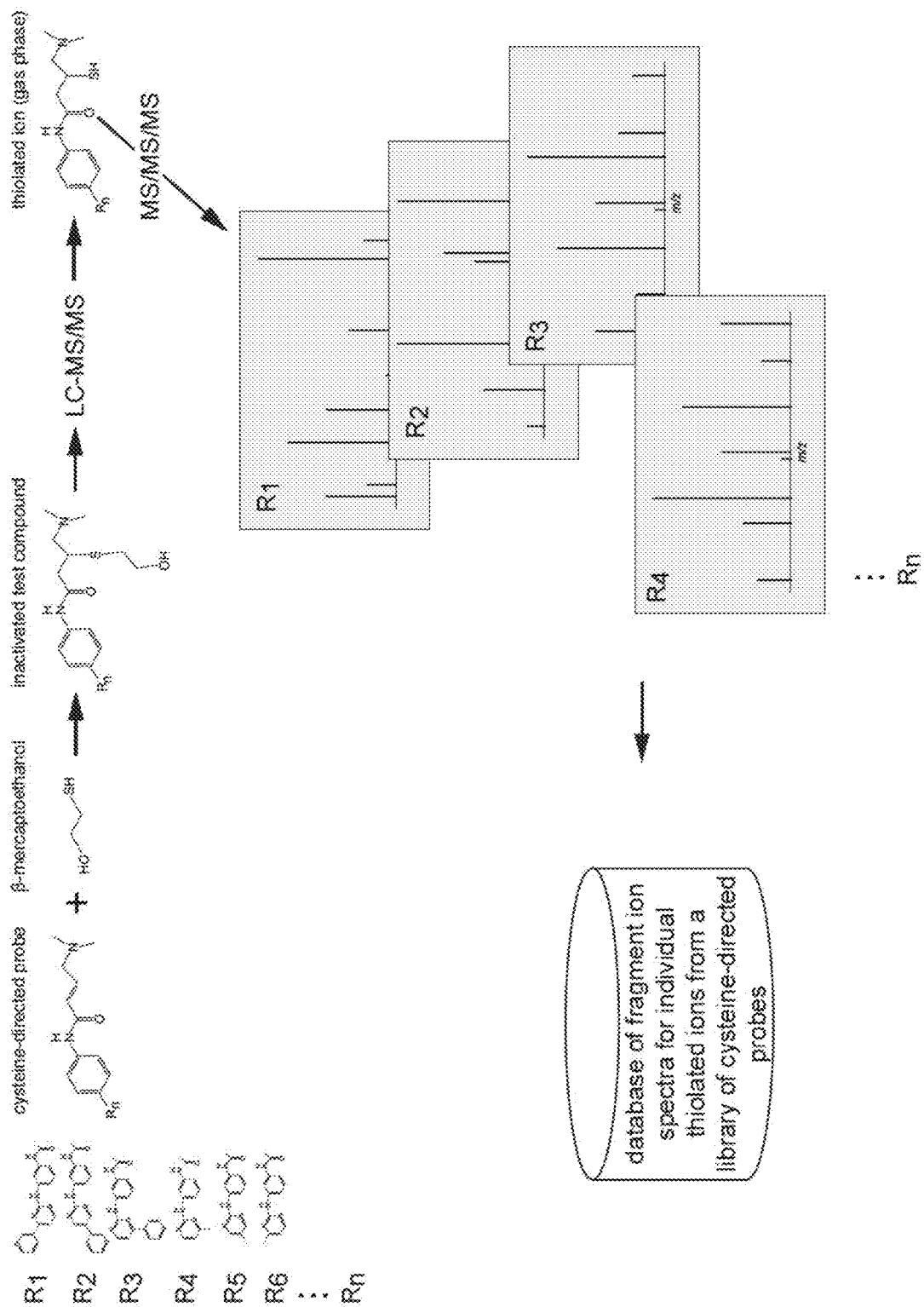
FIGS. 13A-13B illustrate creation of a spectral library of test compound derived thiolated ions.
Figure 13B:
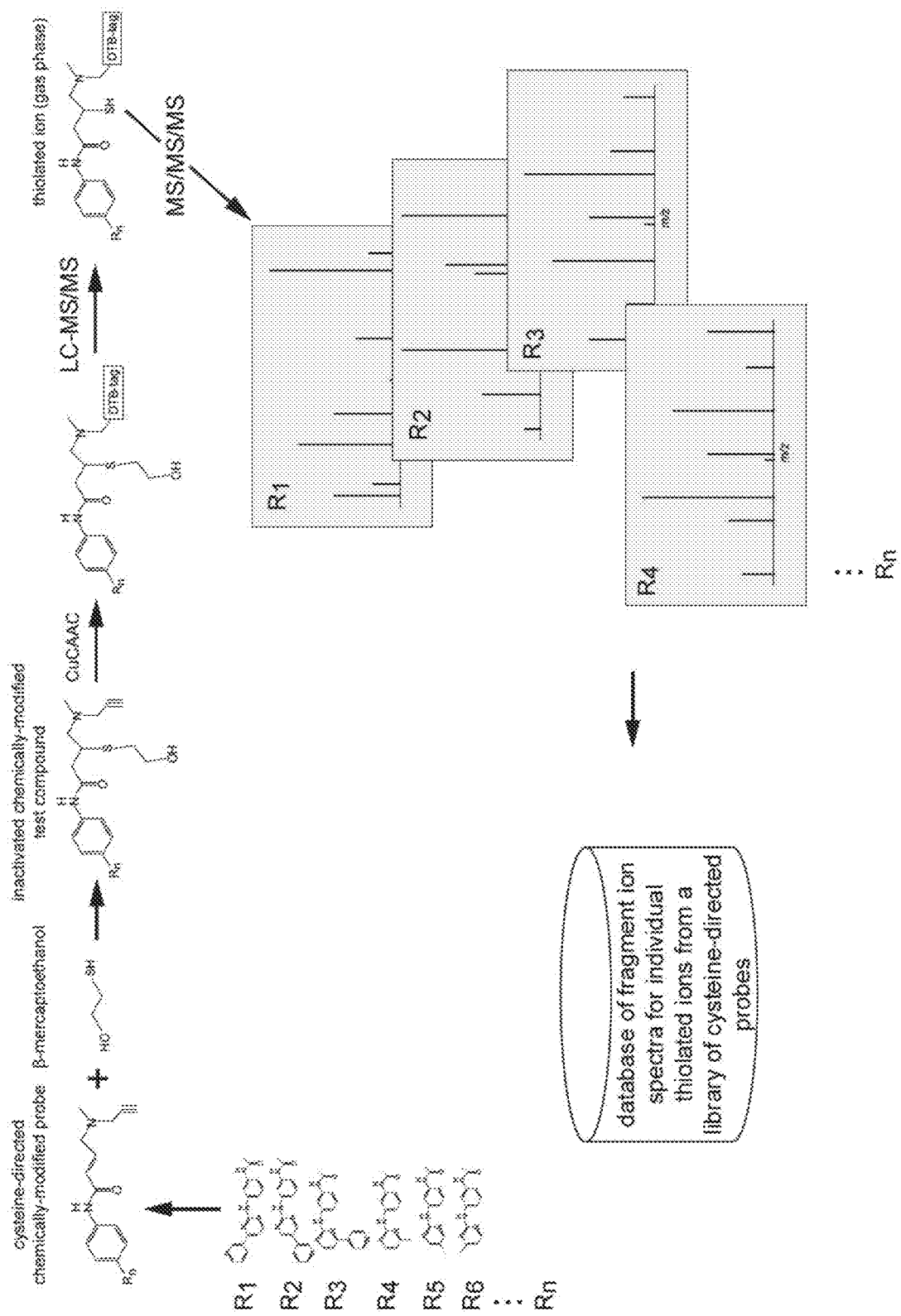
Figure 14A:
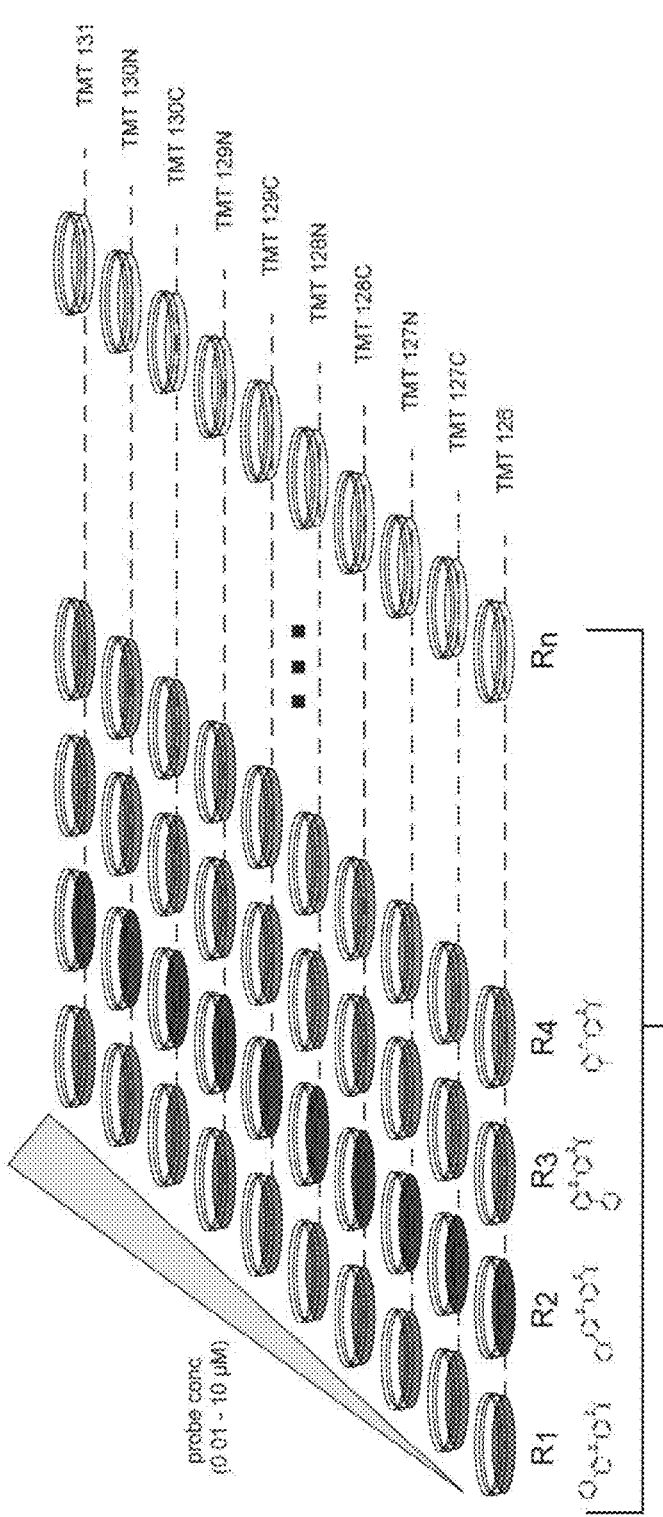
FIGS. 14A-14B show sample processing workflows for massively multiplexed Chemoformics assay.
Figure 14B:
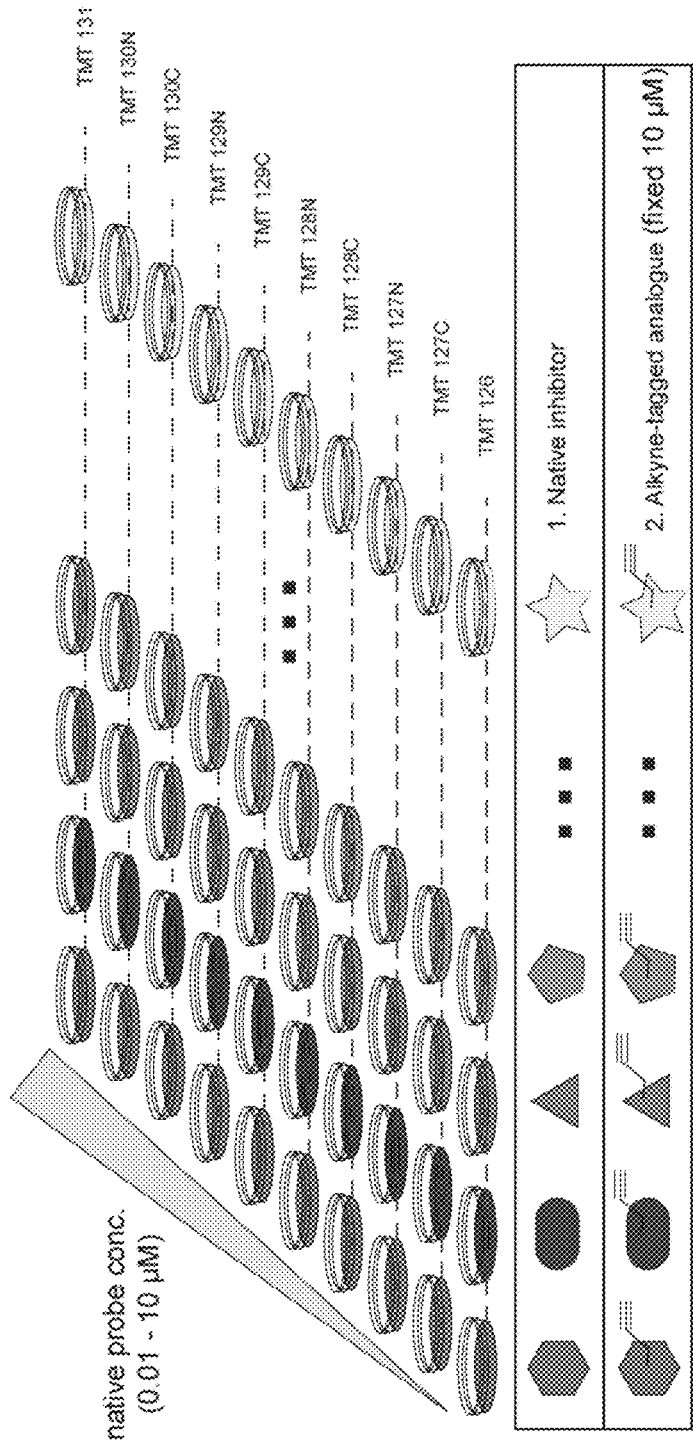
Figure 15:
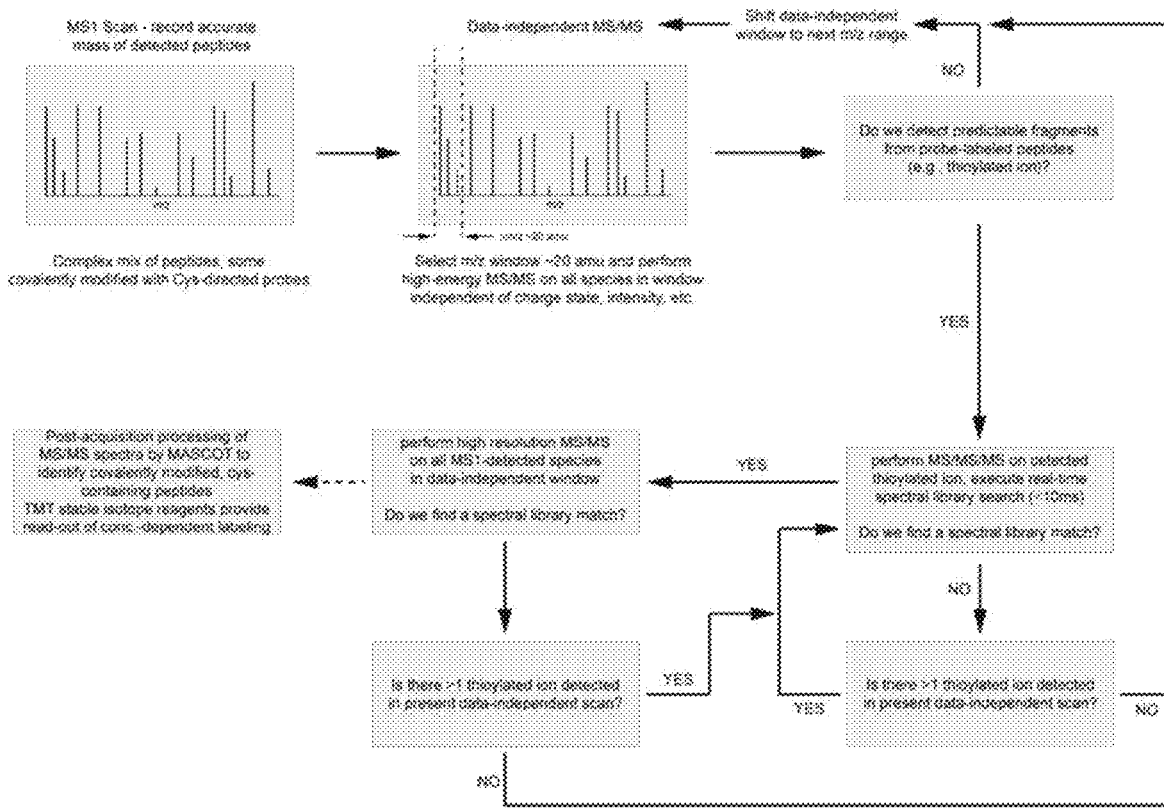
FIG. 15 shows a custom data acquisition scheme for Chemoformics assay. A high resolution MS1 scan records m/z values of tryptic peptides, some of which will be covalently modified by test compounds. Small segments of m/z space (e.g., ~20 Da) are incrementally subjected to MS/MS and spectra screened for thiolated ions or derivative ions thereof. When such ions are detected, MS/MS/MS is used to fragment the thiolated ion and the resulting spectrum is searched against a previously generated thiolated ion spectral library (see e.g., FIG. 13). If there is a match in the spectral database, high resolution MS/MS scans are acquired within the original m/z window (e.g., ~20 Da). MS/MS spectra are matched to parent protein sequences using MASCOT, with variable modification of cysteine set according to the inhibitor identified by the spectral library search. The cycle is repeated until the end of the LC gradient.
Figure 16:
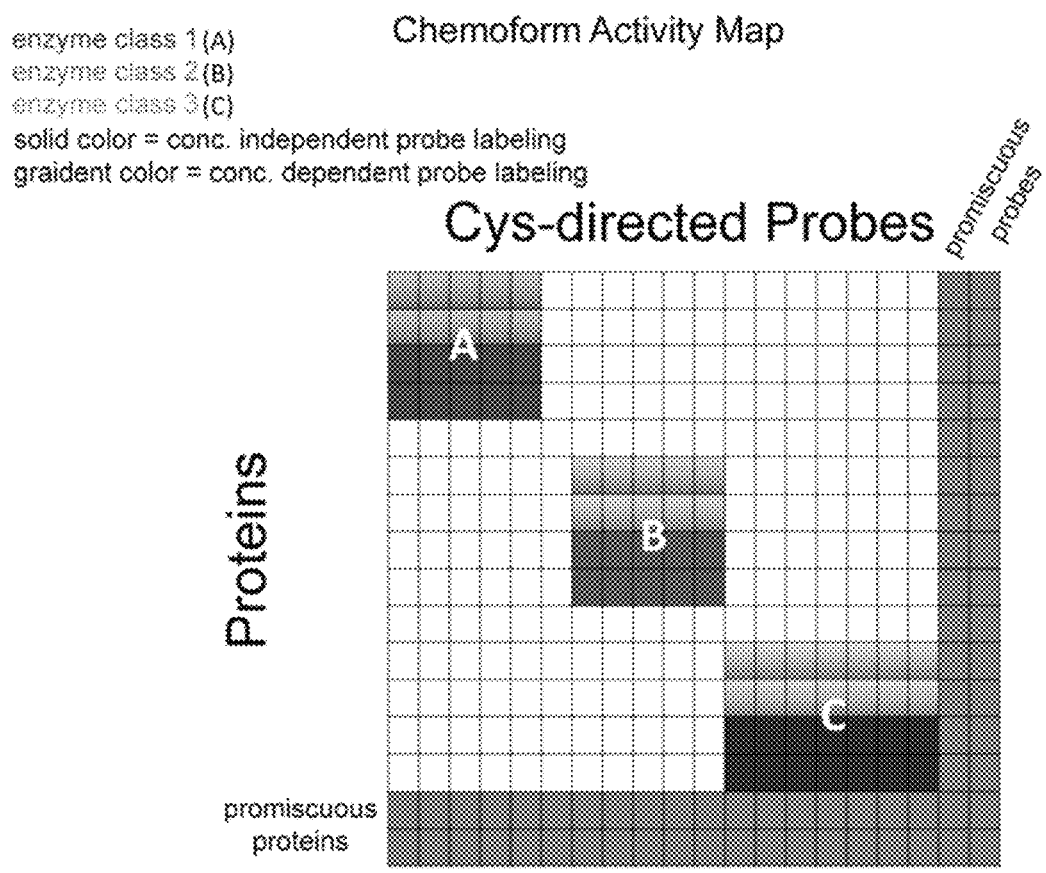
FIG. 16 shows features of a hypothetical representative Chemoformic Activity Map. Proteins detected based on cysteine residues modified by test compounds are listed on the y-axis. Each test compound used in the Chemoformic assay is listed on the x-axis. Color gradients indicate dose-dependent covalent binding for test compounds at different protein-cysteine residues. Some test compounds may covalently modify multiple proteins in a given family such as kinases, deubiquitinating enzymes, etc. These protein families may cluster within the Chemoformic Activity Map (e.g., "A", "B", "C" of FIG. 16). Non-selective covalent test compounds (e.g. "promiscuous probes" of FIG. 16) may exhibit highly promiscuous activity and covalently bind large numbers of proteins; similarly, a subset of cysteine residues on a small number of proteins may be highly reactive and form covalent bonds with a large number of test compounds (e.g., "promiscuous proteins" of FIG. 16).

Next the energetics associated with inhibitor-specific ions was investigated to develop precursor scan mass spectrometry methods to enable selective detection of peptide-probe conjugates. Two peptides were labeled with ibrutinib and spiked into a complex mixture of tryptic peptides derived from human myeloid K562 cells. Precursor scans were then performed on a triple quadrupole mass spectrometer using the collision energies as described above. FIGS. 4A-4G and FIGS. 11A-11F show that selective detection of the thiolated (FIG. 4F) or alkylated amine cleavage product (m/z=304.12, FIG. 11F) ions provide more than an order of magnitude improvement in selectivity as compared to standard full mass range data acquisition (FIG. 4C and FIG. 11C). As a further test of selectivity we next triggered full-scan MS/MS acquisition based on precursor ion signals corresponding to Ibrutinib thiolated ions (m/z 475.19; FIG. 4D). After pre-processing of the resulting peak lists, a MASCOT search yielded 22 peptide-spectral matches (PSMs), corresponding to 16 unique peptide sequences. Notably, the spiked-in synthetic was the only Ibrutinib-modified peptide detected (FIG. 4G, MASCOT score ~49), even though it was amongst the lowest intensity precursor ions in the base peak chromatogram (BPC). Similar gas phase enrichment was observed for precursor ion data obtained for QL47 (targeting thiolated ion and $iy_1$, shown in FIG. 12A-12J). These data suggest that predictable inhibitor-associated fragmentation may be used as a basis to develop selective mass spectrometry assays for detection of proteins targeted by cysteine-directed covalent probes.

Several novel dissociation pathways were identified based on probe structure and reactive warhead (i.e., reactive group). Our results provide evidence for several informative trends: (i) Probes covalently bound by a thioether linkage produce a characteristic thiolated ion independent of peptide sequence and charge state; (ii) Certain dissociation pathways appear to be class-specific; for example, acrylamide warheads undergo a retro Michael addition to regenerate the intact probe, while inhibitors with dimethylamino groups yield a low-mass fragment at m/z=112; (iii) Information for these novel fragmentation pathways can be used to markedly improve peptide sequence identification scores for shotgun proteomic methods; (iv) Use of higher CE provides gas phase enrichment of inhibitor-specific fragments relative to canonical peptide b- and y-type ions.

Example 8. Target Engagement Stoichiometry Assay

Figure 5:
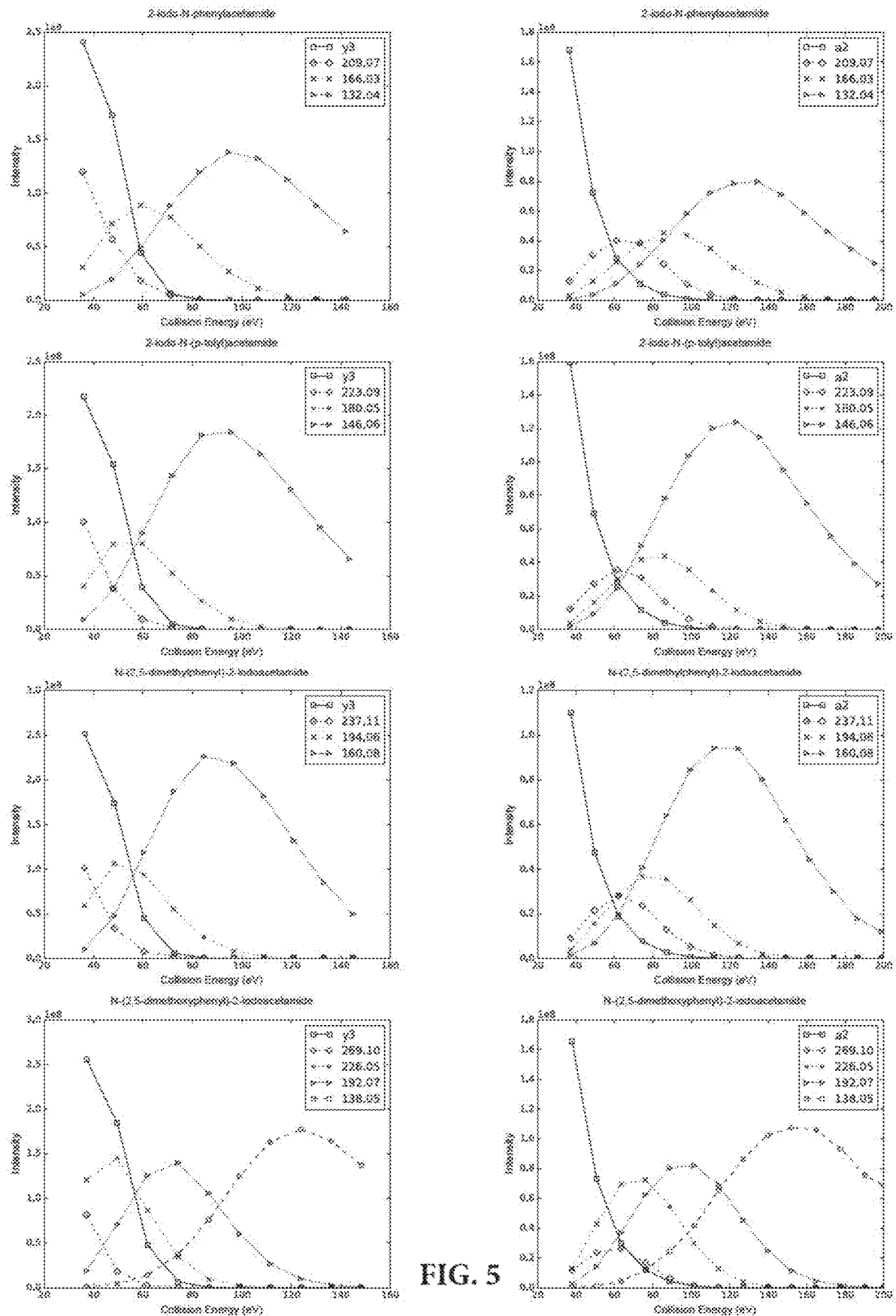
FIG. 5 shows collision energy profiles for peptide F-G-L-C-S-G-P-A-D-T-G-R (SEQ ID NO.: 7; left column) and peptide Y-F-S-N-R-P-G-P-T-P-G-C-Q-L-P-($^{13}C_6$-$^{15}N_4$)-R-P-N-C-P-V-E-T-L-K (SEQ ID NO.: 10; right column) alkylated with 15 broad thiol-reactive reagents. The intensities of peptide-derived y3 and a2 ions (for peptides F-G-L-C-S-G-P-A-D-T-G-R (SEQ ID NO.: 7) and Y-F-S-N-R-P-G-P-T-P-G-C-Q-L-P-($^{13}C_6$-$^{15}N_4$)-R-P-N-C-P-V-E-T-L-K (SEQ ID NO.: 10, respectively) and reagent-derived ions (see e.g., Table 4) are plotted as a function of collision energy (in eV).
Figure 5:
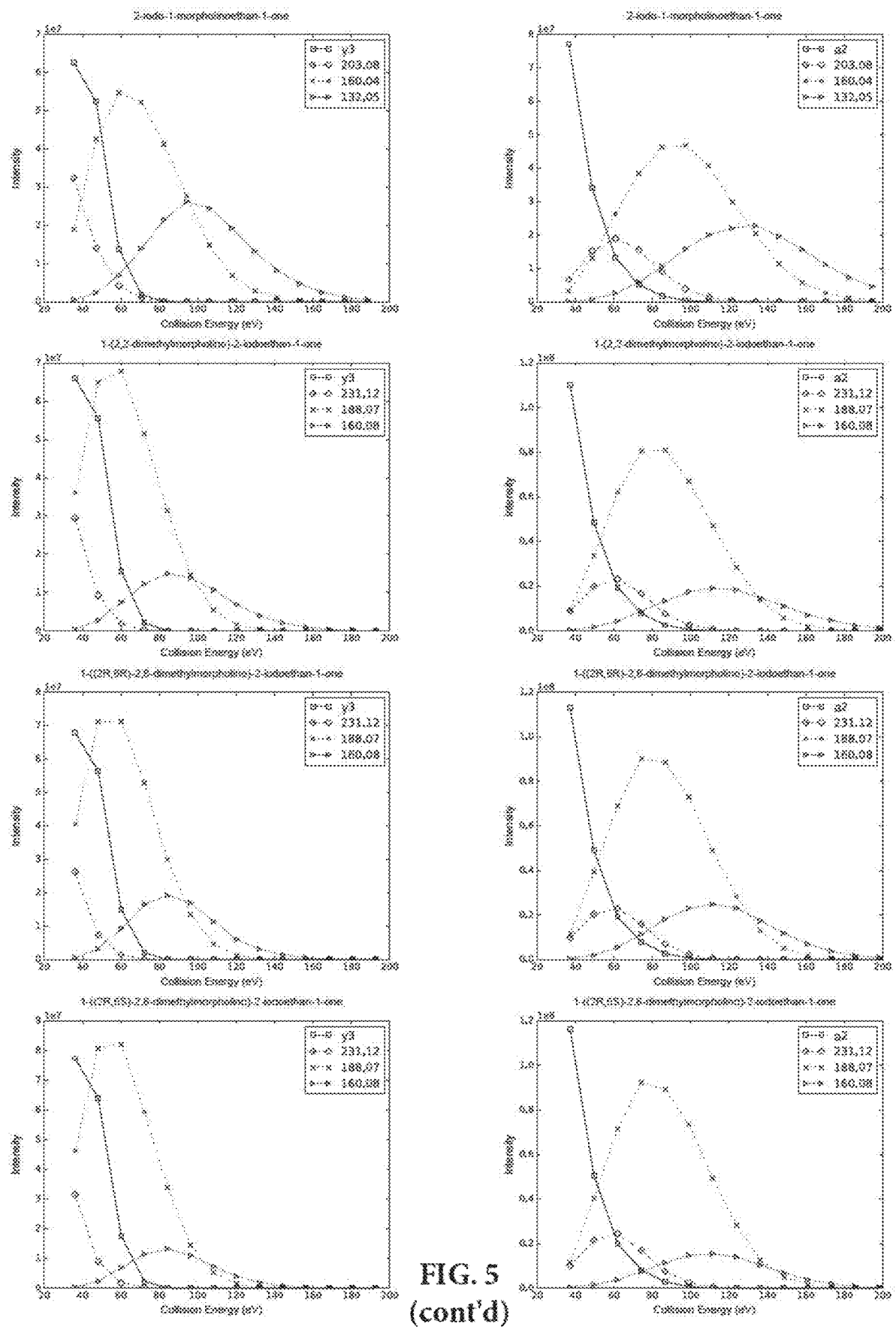
Figure 5:
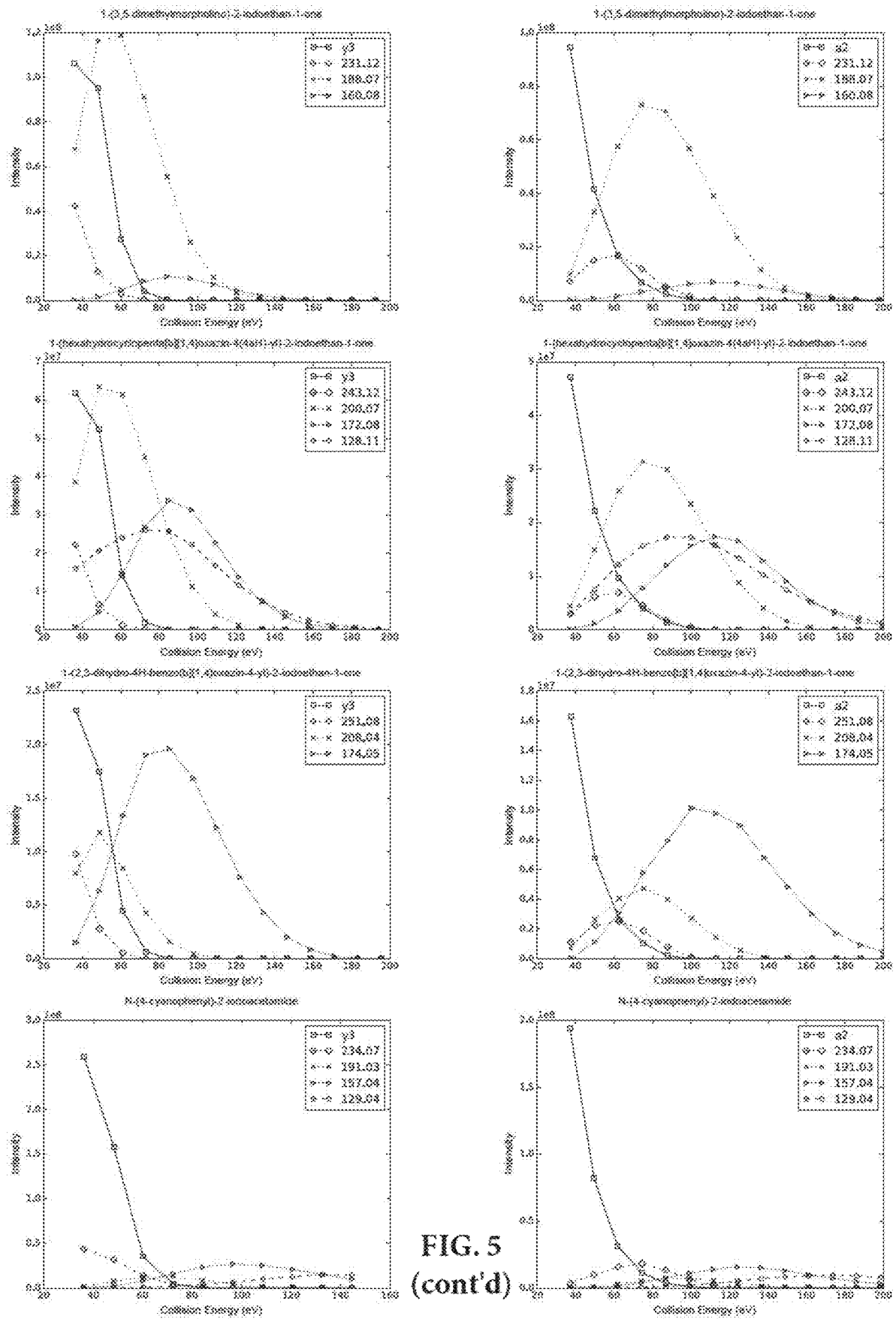
Figure 5:
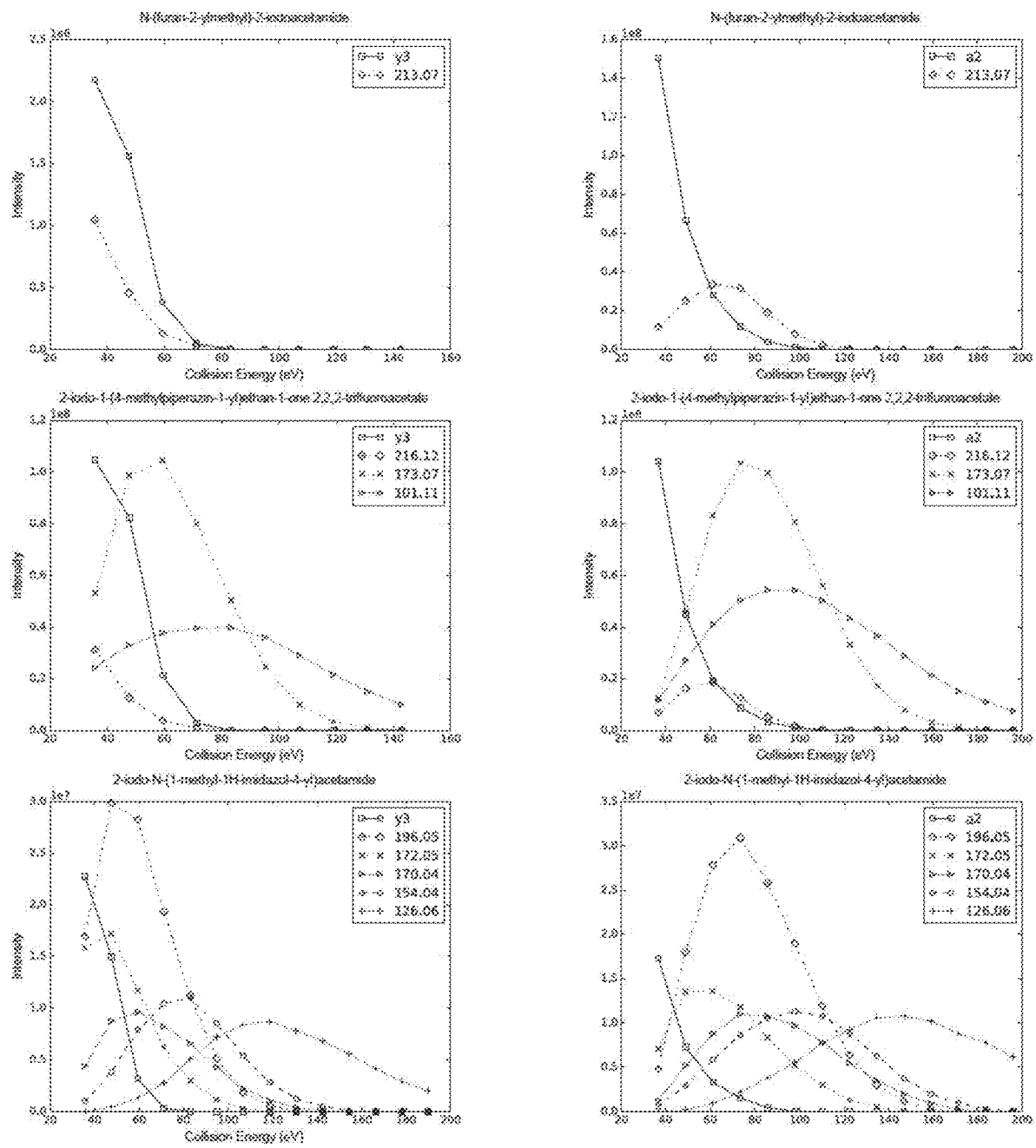
Figure 6:
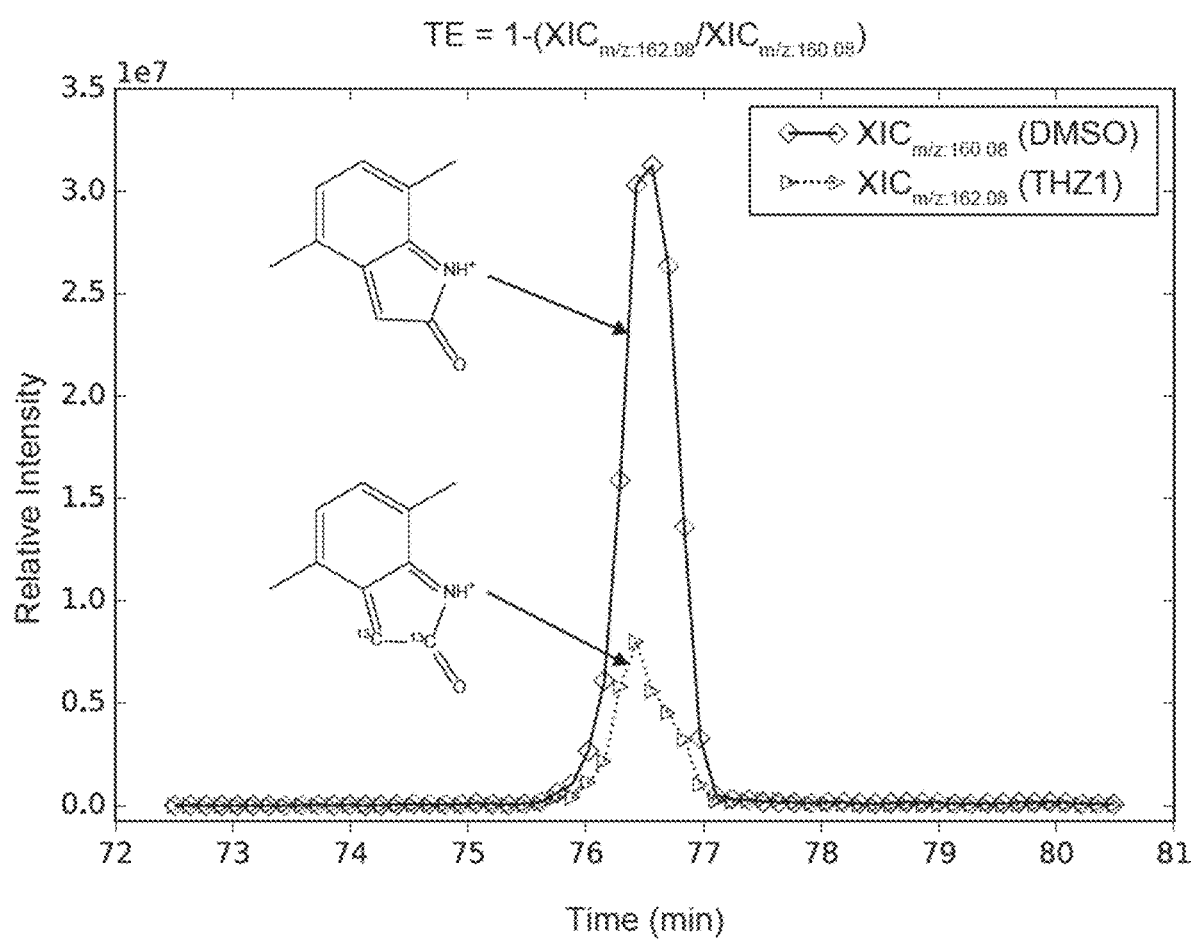
FIG. 6 shows CDK7 target engagement (TE) quantification. CDK7 was immunopurified from DMSO and THZ1-treated cells. Immunopurified CDK7 were labeled with light DMPIA (THZ1-treated) and heavy DMPIA (DMSO-treated) before trypsin digestion, as described in Example 8. eXtracted Ion Chromatograms (XIC) for light DMPIA and heavy DMPIA-derived fragment ions (m/z: 160.08 and m/z: 162.08 respectively) are shown.
Figure 7:
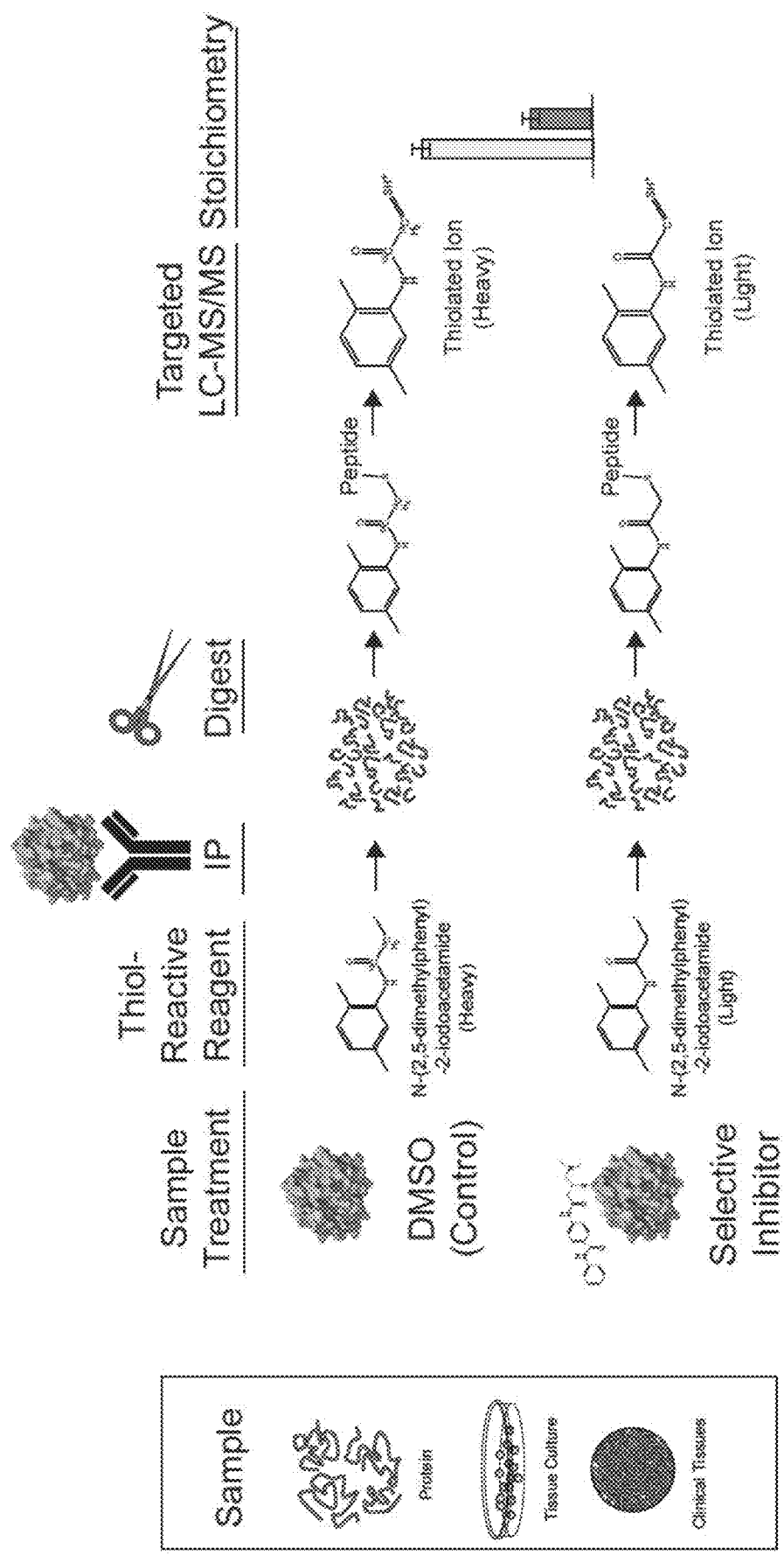
FIG. 7 shows a representative diagram visualizing the workflow of the target engagement stoichiometry assay described in Example 8.
Figures 8A, 8B, 8C, 8D:
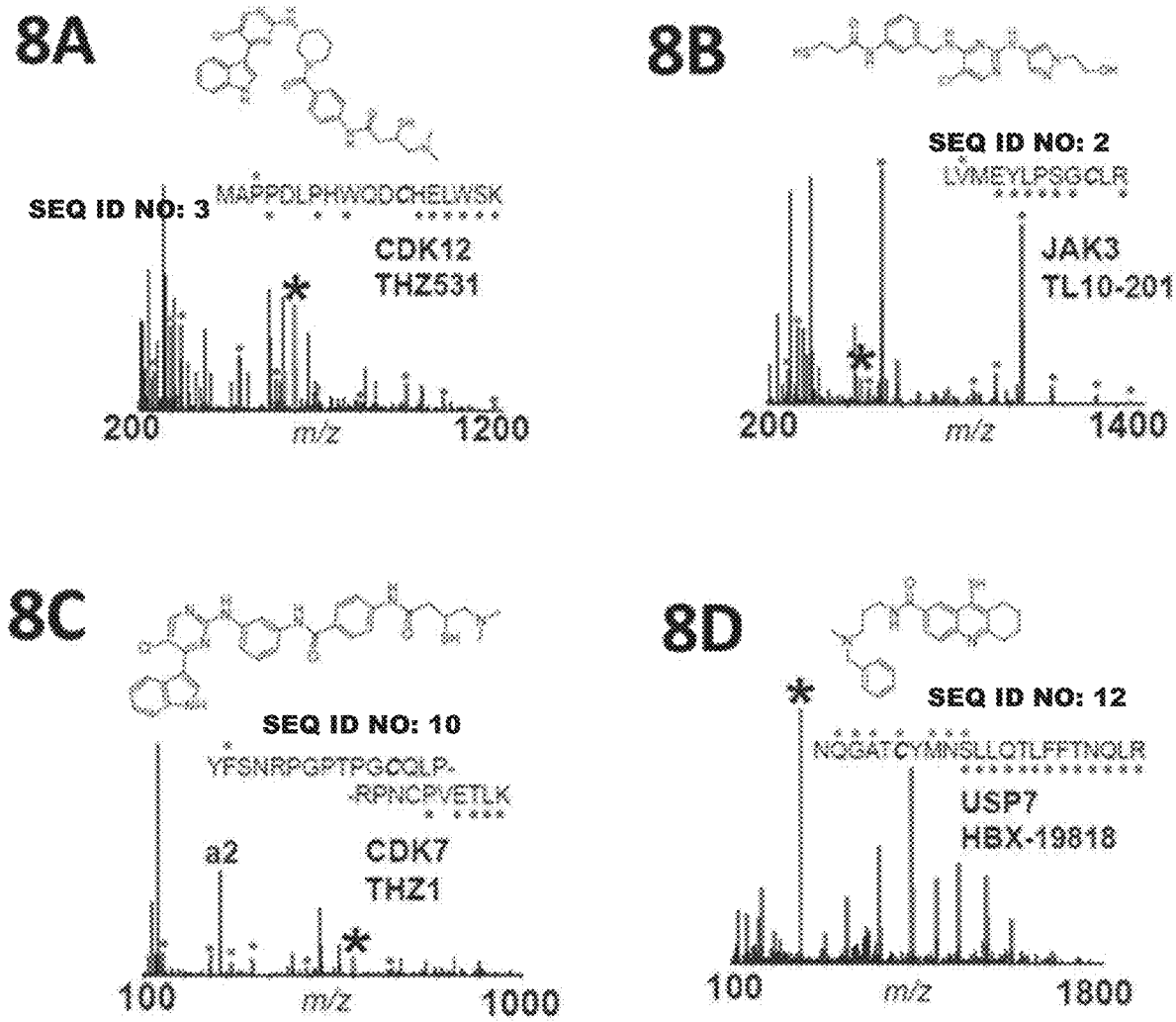
FIGS. 8A-8H show common fragmentation pathways observed in MS/MS spectra of inhibitor conjugated peptides. MS/MS spectra for inhibitor target conjugates (FIG. 8A) THZ531 labeled CDK12 peptide.
Figures 8E, 8F, 8G, 8H:
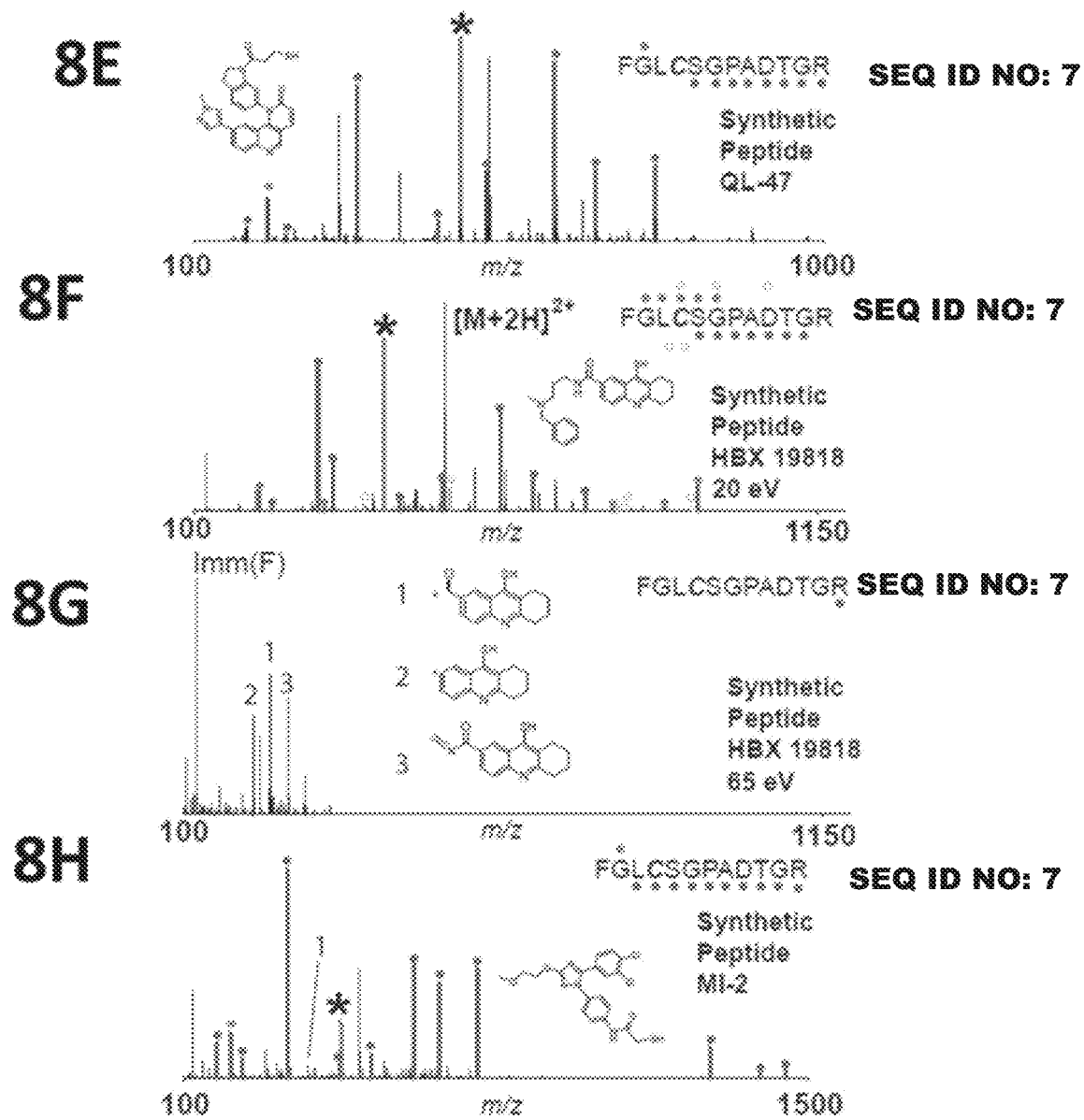

HeLa-S3 cells were treated with 100 nM THZ1 (covalent probe that targets cys-312 on the kinase CDK7) or DMSO (control) for 6 hours. CDK7 was enriched from total cell extracts by immuno-precipitation. The resulting treated (THZ1) and control (DMSO) immuno-precipitates were alkylated with heavy or light N-(2,5-dimethylphenyl)-2-iodoacetamide (DMPIA), respectively. Samples were combined, digested with trypsin, and desalted. The LC-MS/MS method comprised acquisition of targeted MS/MS spectra for both the light and heavy DMPIA-labeled CDK7 peptides containing cys-312: Y-F-S-N-R-P-G-P-T-P-G-C*Q-L-P-R-P-N-C*P-V-E-T-L-K (SEQ ID NO: 11; C* refers to a cysteine residue labeled with DMPIA). In addition, a MS/MS collision energy of 90 eV was used to simultaneously maximize the yield of thiolated ions, or derivative ions thereof, while minimizing the signals for typical fragment ions resulting from peptide amide bond cleavages. Collision energy profiles for the peptides labeled with the broad thiol-reactive reagents are shown in FIG. 5. Quantification of the CDK7 target engagement in shown in FIG. 6. A representative diagram visualizing the workflow of the target engagement stoichiometry assay in shown in FIG. 7.

Table 4 shows a list of broad thiol reactive reagents tested in the target engagement stoichiometry assay showing the chemical structure and chemical formula of the parent sample compounds and related fragment ions. The chemical structure, chemical formula and mass to charge ratio (m/z) for derivative fragment ions produced in the gas phase during MS/MS is also shown.

TABLE 4

| | Reagents and Related Fragment Ions | | |
|---|---|---|---|
| ION | PROPOSED STRUCTURE | FORMULA | ION m/z |
| Parent Iodoacetamide 2-iodo-1-morpholinoethan-1-one | | C6H10INO2 | N/A |
| Compound-modified immonium | | C8H15N2O2S+ | 203.08487 |
| Thiolated | | C6H12NO2S+ | 162.05833 |
| Thiolated-H2 | | C6H10NO2S+ | 160.04268 |

TABLE 4-continued

Reagents and Related Fragment Ions

| ION | PROPOSED STRUCTURE | FORMULA | ION m/z |
|---|---|---|---|
| Thiolated-H2-CO | | C5H10NOS+ | 132.04776 |
| Parent Iodoacetamide 1-((2R,6R)-2,6-dimethylmorpholino)-2-iodoethan-1-one | | C8H14INO2 | N/A |
| Compound-modified immonium | | C10H19N2O2S+ | 231.11617 |
| Thiolated | | C8H16NO2S+ | 190.08963 |
| Thiolated-H2 | | C8H14NO2S+ | 188.07398 |
| Thiolated-H2-CO | | C7H14NOS+ | 160.07906 |
| Parent Iodoacetamide 1-((2R,6S)-2,6-dimethylmorpholino)-2-iodoethan-1-one | | C8H14INO2 | N/A |
| Compound-modified immonium | | C10H19N2O2S+ | 231.11617 |

TABLE 4-continued

Reagents and Related Fragment Ions

| ION | PROPOSED STRUCTURE | FORMULA | ION m/z |
| --- | --- | --- | --- |
| Thiolated | | C8H16NO2S+ | 190.08963 |
| Thiolated-H2 | | C8H14NO2S+ | 188.07398 |
| Thiolated-H2-CO | | C7H14NOS+ | 160.07906 |
| Parent Iodoacetamide 1-(2,2-dimethylmorpholino)-2-iodoethan-1-one | | C8H14INO2 | N/A |
| Compound-modified immonium | | C10H19N2O2S+ | 231.11617 |
| Thiolated | | C8H16NO2S+ | 190.08963 |
| Thiolated-H2 | | C8H14NO2S+ | 188.07398 |
| Thiolated-H2-CO | | C7H14NOS+ | 160.07906 |
| Parent Iodoacetamide 1-(3,5-dimethylmorpholino)-2-iodoethan-1-one | | C8H14INO2 | N/A |

TABLE 4-continued

Reagents and Related Fragment Ions

| ION | PROPOSED STRUCTURE | FORMULA | ION m/z |
| --- | --- | --- | --- |
| Compound-modified immonium | | C10H19N2O2S+ | 231.11617 |
| Thiolated | | C8H16NO2S+ | 190.08963 |
| Thiolated-H2 | | C8H14NO2S+ | 188.07398 |
| Thiolated-H2-CO | | C7H14NOS+ | 160.07906 |
| Parent Iodoacetamide 1-(hexahydrocyclopenta[b][1,4]oxazin-4(4aH)-yl)-2-iodoethan-1-one | | C9H14INO2 | N/A |
| Compound-modified immonium | | C11H19N2O2S+ | 243.11617 |
| Thiolated | | C9H16NO2S+ | 202.08963 |
| Thiolated-H2 | | C9H14NO2S+ | 200.07398 |
| Thiolated-H2-CO | | C8H14NOS+ | 172.07906 |

TABLE 4-continued

Reagents and Related Fragment Ions

| ION | PROPOSED STRUCTURE | FORMULA | ION m/z |
| --- | --- | --- | --- |
| Parent Iodoacetamide 1-(2,3-dihydro-4H-benzo[b][1,4]oxazin-4-yl)-2-iodoethan-1-one | | C10H10INO2 | N/A |
| Compound-modified immonium | | C12H15N2O2S+ | 251.08487 |
| Thiolated | | C10H12NO2S+ | 210.05833 |
| Thiolated-H2 | | C10H10NO2S+ | 208.04268 |
| Cyclic-Thiolated-H2-SH2 | | C10H8NO2+ | 174.05495 |
| Parent Iodoacetamide N-(4-cyanophenyl)-2-iodoacetamide | | C9H7IN2O | N/A |
| Compound-modified immonium | | C11H12N3OS+ | 234.06956 |
| Thiolated | | C9H9N2OS+ | 193.04301 |
| Thiolated-H2 | | C9H7N2OS+ | 191.02736 |

TABLE 4-continued

| | Reagents and Related Fragment Ions | | |
|---|---|---|---|
| ION | PROPOSED STRUCTURE | FORMULA | ION m/z |
| Cyclic-Thiolated-H2-SH2 | (5-cyano-indolin-2-one, NH+) | C9H5N2O+ | 157.03964 |
| Cyclic-Thiolated-H2-SH2-CO | Structure to be determined | C8H5N2+ | 129.04472 |
| Parent Iodoacetamide N-(2,5-dimethylphenyl)-2-iodoacetamide | (N-(2,5-dimethylphenyl)-2-iodoacetamide) | C10H12INO | N/A |
| Compound-modified immonium | (N-(2,5-dimethylphenyl)-2-(S-CH2-CH=NH2+)acetamide) | C12H17N2OS+ | 237.10561 |
| Thiolated | (N-(2,5-dimethylphenyl)-2-(SH2+)acetamide) | C10H14NOS+ | 196.07906 |
| Thiolated-H2 | (N-(2,5-dimethylphenyl)-2-(=SH+)acetamide) | C10H12NOS+ | 194.06341 |
| Cyclic-Thiolated-H2-SH2 | (4,7-dimethyl-indolin-2-one, NH+) | C10H10NO+ | 160.07569 |
| Parent Iodoacetamide N-(2,5-dimethoxyphenyl)-2-iodoacetamide | (N-(2,5-dimethoxyphenyl)-2-iodoacetamide) | C10H12INO3 | N/A |
| Compound-modified immonium | (N-(2,5-dimethoxyphenyl)-2-(S-CH2-CH=NH2+)acetamide) | C12H17N2O3S+ | 269.09544 |

TABLE 4-continued

Reagents and Related Fragment Ions

| ION | PROPOSED STRUCTURE | FORMULA | ION m/z |
|---|---|---|---|
| Thiolated | | C10H14NO3S+ | 228.06889 |
| Thiolated-H2 | | C10H12NO3S+ | 226.05324 |
| Cyclic-Thiolated-H2-SH2 | | C10H10NO3+ | 192.06552 |
| Cyclic-Thiolated-H2-SH2-C3H2O | Structure to be determined | C7H8NO2+ | 138.05495 |
| Parent Iodoacetamide 2-iodo-N-phenylacetamide | | C8H8INO | N/A |
| Compound-modified immonium | | C10H13N2OS+ | 209.07431 |
| Thiolated | | C8H10NOS+ | 168.04776 |
| Thiolated-H2 | | C8H8NOS+ | 166.03211 |
| Cyclic-Thiolated-H2-SH2 | | C8H6NO+ | 132.04439 |
| Parent Iodoacetamide 2-iodo-N-(p-tolyl)acetamide | | C9H10INO | N/A |

TABLE 4-continued

Reagents and Related Fragment Ions

| ION | PROPOSED STRUCTURE | FORMULA | ION m/z |
|---|---|---|---|
| Compound-modified immonium | | C11H15N2OS+ | 223.08996 |
| Thiolated | | C9H12NOS+ | 182.06341 |
| Thiolated-H2 | | C9H10NOS+ | 180.04776 |
| Cyclic-Thiolated-H2-SH2 | | C9H8NO+ | 146.06004 |
| Parent Iodoacetamide 2-iodo-1-(4-methylpiperazin-1-yl)ethan-1-one 2,2,2-trifluoroacetate | | C9H14F3IN2O3 | N/A |
| Compound-modified immonium | | C9H18N3OS+ | 216.11651 |
| Thiolated | | C7H15N2OS+ | 175.08996 |
| Thiolated-H2 | | C7H13N2OS+ | 173.07431 |
| Thiolated-H2-SH2 | | C5H13N2+ | 101.10732 |

TABLE 4-continued

Reagents and Related Fragment Ions

| ION | PROPOSED STRUCTURE | FORMULA | ION m/z |
|---|---|---|---|
| Parent Iodoacetamide N-(furan-2-ylmethyl)-2-iodoacetamide | | C7H8INO2 | N/A |
| Compound-modified immonium | | C9H13N2O2S+ | 213.06922 |
| Parent Iodoacetamide 2-iodo-N-(1-methyl-1H-imidazol-4-yl)acetamide | | C6H8IN3O | N/A |
| Compound-modified immonium | | C8H13N4OS+ | 213.08046 |
| Compound-modified immonium-NH3 | | C8H10N3OS+ | 196.05391 |
| Thiolated | | C6H10N3OS+ | 172.05391 |
| Thiolated-H2 | | C6H8N3OS+ | 170.03826 |
| Thiolated-H2O | | C6H8N3S+ | 154.04334 |
| Thiolated-CH2S | | C5H8N3O+ | 126.06619 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An analytical method, comprising:
   i) contacting a broad thiol reactive compound with a polypeptide to form a broad thiol reactive compound-polypeptide conjugate;
   ii) analyzing the broad thiol reactive compound-polypeptide conjugate using a mass spectrometry assay;
   iii) detecting one or more thiolated ions of the broad thiol reactive compound, or derivative ions thereof, produced in the mass spectrometry assay; and
   iv) identifying that the broad thiol reactive compound forms an irreversible bond with the polypeptide based on the detection of the one or more thiolated ions, or derivative ions thereof, in the mass spectrometry assay;
   wherein the thiolated ions or derivatives thereof are fragment ions.

2. The method of claim 1, wherein the compound-polypeptide conjugate comprises one or more thioether bonds between the compound and the polypeptide.

3. The method of claim 1, wherein step i) comprises contacting the compound and the polypeptide in the presence of a first solvent component.

4. The method of claim 1, wherein step i) further comprises contacting the compound and the polypeptide in the presence of a buffer agent.

5. The method of claim 1, wherein step i) is performed using a molar excess of the compound compared to the polypeptide.

6. The method of claim 1, further comprising contacting the broad thiol reactive compound-polypeptide conjugate with an acid in the presence of a second solvent component prior to performing the mass spectrometry assay of step ii).

7. The method of claim 1, wherein the method further comprises digesting the broad thiol reactive compound-polypeptide conjugate prior to the performing the mass spectrometry assay of step ii).

8. The method of claim 7, wherein the digesting comprises reacting the broad thiol reactive compound-polypeptide conjugate with trypsin in the presence of a third solvent component.

9. The method of claim 1, wherein the polypeptide comprises one or more amino acids residues comprising at least one sulfur atom.

10. The method of claim 9, wherein the polypeptide comprises one or more cysteine residues.

11. The method of claim 10, wherein the broad thiol reactive compound is identified as irreversibly bonding to one or more cysteine residues of the polypeptide.

12. The method of claim 11, wherein the broad thiol reactive compound comprises one or more groups independently selected from the group consisting of acrylamide groups, dimethylamino acrylamide groups, iodoacetamide groups, chloroacetamide groups, maleimide groups, and C—X groups, wherein X is a halogen.

13. The method of claim 1, wherein the broad thiol reactive compound is selected from the group consisting of
   2-iodo-1-morpholinoethan-1-one;
   1-((2R,6R)-2,6-dimethylmorpholino)-2-iodoethan-1-one;
   1-((2R,6S)-2,6-dimethylmorpholino)-2-iodoethan-1-one;
   1-(2,2-dimethylmorpholino)-2-iodoethan-1-one;
   1-(3,5-dimethylmorpholino)-2-iodoethan-1-one;
   1-(hexahydrocyclopenta[b][1,4]oxazin-4(4aH)-yl)-2-iodoethan-1-one;
   1-(2,3-dihydro-4H-benzo[b][1,4]oxazin-4-yl)-2-iodoethan-1-one;
   N-(4-cyanophenyl)-2-iodoacetamide;
   N-(2,5-dimethylphenyl)-2-iodoacetamide;
   N-(2,5-dimethoxyphenyl)-2-iodoacetamide;
   2-iodo-N-phenylacetamide;
   2-iodo-N-(p-tolyl)acetamide;
   2-iodo-1-(4-methylpiperazin-1-yl)ethan-1-one 2,2,2-trifluoroacetate;
   N-(furan-2-ylmethyl)-2-iodoacetamide;
   2-iodo-N-(1-methyl-1H-imidazol-4-yl)acetamide; and
   N-ethylmaleimide.

14. The method of claim 1, wherein the polypeptide is a protein or a protein fragment.

15. The method of claim 1, wherein the polypeptide is a protein fragment comprising from about 10 to about 30 amino acid residues.

16. The method of claim 1, wherein the polypeptide is a kinase or a fragment thereof, or a deubiquitinase or a fragment thereof.

17. The method of claim 1, wherein the polypeptide is a kinase selected from the group consisting of JNK2, JAK3, CDK7, CDK12, ITK, USP-7, TAK1, and EGFR, or a fragment thereof.

18. The method of claim 1, wherein the polypeptide is a kinase fragment comprising from about 10 to about 30 amino acid residues.

19. The method of claim 1, wherein the polypeptide comprises an amino acid sequence having at least 90% sequence identity to a sequence selected from the group consisting of:

```
                              (SEQ ID NO: 1)
L-M-D-A-N-L-C-Q-V-I-Q-M-E;

(SEQ ID NO: 2)
L-V-M-E-Y-L-P-S-G-C-L-R;

(SEQ ID NO: 3)
M-A-P-P-D-L-P-H-W-Q-D-C-H-E-L-W-S-K;

(SEQ ID NO: 4)
H-G-C-L-S-D-Y-L-R-S-Q-R-G-L-F-A-A-E;

(SEQ ID NO: 5)
Y-F-S-N-R-P-G-P-T-P-G-C-Q-L-P-R-P-N-C-P-V-E-T-L-K;

(SEQ ID NO: 6)
G-C-L-L-D-Y-V-R;

(SEQ ID NO: 7)
F-G-L-C-S-G-P-A-D-T-G-R;

(SEQ ID NO: 8)
Y-M-A-N-G-C-L-sL-N-Y-L-R;

(SEQ ID NO: 9)
I-C-D-F-G-T-A-C-D-I-Q-T-H-M-T-N-N-K;
and
                              (SEQ ID NO: 10)
Y-F-S-N-R-P-G-P-T-P-G-C-Q-L-P-(13C6-15N4)R-P-N-C-
P-V-E-T-L-K.
```

\* \* \* \* \*

SEQUENCE LISTING

<160> NUMBER OF SEQ ID NOS: 12

<210> SEQ ID NO 1
<211> LENGTH: 13
<212> TYPE: PRT
<213> ORGANISM: Artificial Sequence
<220> FEATURE:

<223> OTHER INFORMATION: JNK1-derived peptide

<400> SEQUENCE: 1

Leu Met Asp Ala Asn Leu Cys Gln Val Ile Gln Met Glu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: JAK3-derived peptide

<400> SEQUENCE: 2

Leu Val Met Glu Tyr Leu Pro Ser Gly Cys Leu Arg
1               5                   10

<210> SEQ ID NO 3
<211> LENGTH: 18
<212> TYPE: PRT
<213> ORGANISM: Artificial Sequence
<220> FEATURE:
<223> OTHER INFORMATION: CDK12 derived peptide

<400> SEQUENCE: 3

Met Ala Pro Pro Asp Leu Pro His Trp Gln Asp Cys His Glu Leu Trp
1               5                   10                  15

Ser Lys

<210> SEQ ID NO 4
<211> LENGTH: 18
<212> TYPE: PRT
<213> ORGANISM: Artificial Sequence
<220> FEATURE:
<223> OTHER INFORMATION: ITK derived peptide

<400> SEQUENCE: 4

His Gly Cys Leu Ser Asp Tyr Leu Arg Ser Gln Arg Gly Leu Phe Ala
1               5                   10                  15

Ala Glu

<210> SEQ ID NO 5
<211> LENGTH: 25
<212> TYPE: PRT
<213> ORGANISM: Artificial Sequence
<220> FEATURE:
<223> OTHER INFORMATION: CDK7 derived peptide

<400> SEQUENCE: 5

Tyr Phe Ser Asn Arg Pro Gly Pro Thr Pro Gly Cys Gln Leu Pro Arg
1               5                   10                  15

Pro Asn Cys Pro Val Glu Thr Leu Lys
            20                  25

<210> SEQ ID NO 6
<211> LENGTH: 8
<212> TYPE: PRT
<213> ORGANISM: Artificial Sequence
<220> FEATURE:
<223> OTHER INFORMATION: EGFR derived peptide

<400> SEQUENCE: 6

Gly Cys Leu Leu Asp Tyr Val Arg
1               5

```
<210> SEQ ID NO 7
<211> LENGTH: 12
<212> TYPE: PRT
<213> ORGANISM: Artificial Sequence
<220> FEATURE:
<223> OTHER INFORMATION: synthetic cysteine-containing peptide

<400> SEQUENCE: 7

Phe Gly Leu Cys Ser Gly Pro Ala Asp Thr Gly Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic peptides
<220> FEATURE:
<221> NAME/KEY: MISC_FEATURE
<222> LOCATION: (8)..(8)
<223> OTHER INFORMATION: X=15N-1, 13C-6 leucine

<400> SEQUENCE: 8

Tyr Met Ala Asn Gly Cys Leu Xaa Asn Tyr Leu Arg
1               5                   10

<210> SEQ ID NO 9
<211> LENGTH: 18
<212> TYPE: PRT
<213> ORGANISM: Artificial Sequence
<220> FEATURE:
<223> OTHER INFORMATION: TAK1 derived peptide

<400> SEQUENCE: 9

Ile Cys Asp Phe Gly Thr Ala Cys Asp Ile Gln Thr His Met Thr Asn
1               5                   10                  15

Asn Lys

<210> SEQ ID NO 10
<211> LENGTH: 26
<212> TYPE: PRT
<213> ORGANISM: Artificial Sequence
<220> FEATURE:
<223> OTHER INFORMATION: CDK7 derived peptide
<220> FEATURE:
<221> NAME/KEY: MISC_FEATURE
<222> LOCATION: (16)..(16)
<223> OTHER INFORMATION: X=13C6 -15N4

<400> SEQUENCE: 10

Tyr Phe Ser Asn Arg Pro Gly Pro Thr Pro Gly Cys Gln Leu Pro Xaa
1               5                   10                  15

Arg Pro Asn Cys Pro Val Glu Thr Leu Lys
            20                  25

<210> SEQ ID NO 11
<211> LENGTH: 25
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: X=cysteine residue labeled with DMPIA

<400> SEQUENCE: 11
```

```
Tyr Phe Ser Asn Arg Pro Gly Pro Thr Pro Gly Xaa Gln Leu Pro Arg
1               5                   10                  15

Pro Asn Cys Pro Val Glu Thr Leu Lys
            20              25

<210> SEQ ID NO 12
<211> LENGTH: 22
<212> TYPE: PRT
<213> ORGANISM: Artificial Sequence
<220> FEATURE:
<223> OTHER INFORMATION: USP7 derived peptide

<400> SEQUENCE: 12

Asn Gln Gly Ala Thr Cys Tyr Met Asn Ser Leu Leu Gln Thr Leu Phe
1               5                   10                  15

Phe Thr Asn Gln Leu Arg
            20
```